US008263658B2

(12) United States Patent
Andersson et al.

(10) Patent No.: US 8,263,658 B2
(45) Date of Patent: Sep. 11, 2012

(54) ANTHRANILIC ACID DERIVATIVES

(75) Inventors: Helén Tuvesson Andersson, Lund (SE); Ulf Vellmar, Södra Sandby (SE); Ingrid Hallin, Lund (SE); Leif Svenson, Rydebäck (SE); Ingela Fritzson, Lund (SE)

(73) Assignee: Chelsea Therapeutics, Inc., Charlotte, NC (US)

( * ) Notice: Subject to any disclaimer, the term of this patent is extended or adjusted under 35 U.S.C. 154(b) by 380 days.

(21) Appl. No.: 12/535,358

(22) Filed: Aug. 4, 2009

(65) Prior Publication Data

US 2010/0029767 A1 Feb. 4, 2010

Related U.S. Application Data

(63) Continuation of application No. PCT/SE2008/050126, filed on Jan. 31, 2008.

(60) Provisional application No. 60/899,660, filed on Feb. 6, 2007.

(30) Foreign Application Priority Data

Feb. 6, 2007 (SE) ...................................... 0700281

(51) Int. Cl.
 *A61K 31/195* (2006.01)
 *C07C 229/56* (2006.01)
(52) U.S. Cl. .......................... 514/563; 562/450; 562/458
(58) Field of Classification Search .................. 514/563; 562/450, 458
 See application file for complete search history.

(56) References Cited

U.S. PATENT DOCUMENTS

| 4,307,113 A | 12/1981 | Anderson |
| 5,990,116 A | 11/1999 | Nussbaumer |
| 6,841,561 B1 | 1/2005 | Tan et al. |
| 7,074,831 B2 | 7/2006 | Jönsson et al. |
| 7,423,057 B2 | 9/2008 | Leban et al. |
| 2005/0187297 A1* | 8/2005 | Jonsson et al. ................ 514/563 |
| 2006/0089413 A1 | 4/2006 | Schmaus et al. |

FOREIGN PATENT DOCUMENTS

| DE | 2 064 305 | 7/1972 |
| EP | 0 034 292 | 8/1981 |
| EP | 0 181 568 | 5/1986 |
| EP | 0 497 740 | 8/1992 |
| WO | WO 96/28430 | 9/1996 |
| WO | WO 97/28118 | 8/1997 |
| WO | WO 03/006425 | 1/2003 |
| WO | WO 2005/075410 | 8/2005 |

OTHER PUBLICATIONS

Wakefield B, "Fluorinated pharmaceuticals", Innovations in Pharmaceutical Technology, Jan. 2000, 74 and 76-78.*

Albert et al., "Isoxazolythioamides As Potential Immunosuppressants A Combinatorial Chemistry Approach," Bioorganic & Medicinal Chemistry Letters, (1998) vol. 8, No. 16, pp. 2203-2208.
Batt, "Inhibitors of dihydroorotate dehydrogenase," Exp. Opin. Ther. Patents (1999) vol. 9, No. 1, pp. 41-54.
Breedveld, "New Insights in the Pathogenesis of Rheumatoid Arthritis," The Journal of Rheumatology (1998) vol. 25, supplement 53, pp. 3-7.
Bruneau et al. "Purification of human dihydrorotate dehydrogenase and its inhibition by A77 1726, the active metabolite of leflunomide," Biochem, J. (1998) vol. 336, pp. 299-303.
Chan et al. "New N- and—O-Ariations with Phenylboronic Acids and Cupric Acetate," Tetrahedron Letters (1998) vol. 39, pp. 2933-2936.
Cherwinski, "The Immunosuppressant Leflunomide Inhibits Lymphocyte Proliferation by Inhibiting Pyrimidine Biosynthesis," The Journal of Pharmacology and Experimental Therapeutics (1995) vol. 275, No. 2, pp. 1043-1049.
Gennari et al. "Anaerobic Degradation of Acifluorfen by Different Enrichment Cultures," J. Agric. Food Chem, (1994) vol. 42, pp. 1232-1236.
Hutchinson et al. "Non-Peptide Glycoprotein IIb/IIIa Antagonists. 11. Design and in Vivo Evaluation of 3, 4-Dihydro-1 (1H)-isoquinolinone-Based Antagonists and Ethyl Ester Prodrugs," J. Med. Chem. (1996) vol. 39, pp. 4583-4591.
Kubinyi, "QSAR: Hansch Analysis and Related Approaches" (1993) ISBN 1-56081-768-2 (VCH) "Chapter 3: Parameters" pp. 21-27.
Mathis et al., "Synthesis and Evaluation of $^{11}$C-Labeled 6-Substituted 2-Arylbenzothiazoles as Amyloid Imaging Agents," J. Med. Chem. (2003) vol. 46, pp. 2740-2754.
Novartis Forschungsinstitut GmbH, "Synthetic Analogues of the Partial Structure of the Natural Product Lavendustin A (Novartis Forschungsinstitu GmbH, A-I 230 Vienna, Austria)", Research Disclosure, May 10, 1998, pp. 1-3, Research Disclosure Journal No. 409053.
Ohnmacht et al. "N-Aryl-3,3,3-trifluoro-2-hydroxy-2-methylpropanamides: $K_{ATP}$ Potassium Channel Openers. Modifications on the Western Region," J. Med. Chem. (1996) vol. 39, No. 23, pp. 4592-4601.
Pandey et al. "Synthesis and antiviral activity of quinazolyl thiatriazoles," Acta Pharm. (2002) vol. 52, No. 2, pp. 129-136, compound 1, p. 133.
Patil et al. "Folate Analogues. 32. Synthesis and Biological Evaluation of 2-Desamino-2-methyl-N$^{10}$-propargyl-5,8-dideazafolic Acid and Related Compounds," J. Med. Chem. (1989) vol. 32, No. 6, pp. 1284-1289.

(Continued)

*Primary Examiner* — Paul Zarek
(74) *Attorney, Agent, or Firm* — Womble Carlyle Sandridge & Rice, LLP

(57) ABSTRACT

Compounds of formula (I) are provided, wherein X is CH=CH, CH$_2$O wherein the oxygen atom is bound to ring B, or OCH$_2$ wherein the oxygen atom is bound to ring A; Y is hydrogen, straight or branched C1-C6 alkyl or a pharmaceutically acceptable inorganic cation; R1 is ethyl or cyclopropyl; and R2 and R3 are the same or different and are selected from F, Cl, Br, CF$_3$ and OCF$_3$. The compounds are useful for the treatment of autoimmune diseases, inflammatory diseases, organ transplant rejection, and malignant neoplasia. Pharmaceutical compositions comprising the compounds, methods of using the compounds, and methods for preparing the compounds are also provided.

80 Claims, No Drawings

OTHER PUBLICATIONS

Remington's Pharmaceutical Sciences. Ed. 17, Alfonso R. Gennaro, editor, Easton: Mack Pub. Co., 1985, Chapter 76, pp. 1409-1423.

Roos et al. "Approach to the Synthesis of (+)-ifforestine. Model Studies Directed at the Tetracyclic Framework", Heterocycles, (2003) vol. 60, No. 9, pp. 2023-2044.

Sevbo et al., Derivatives of 2-Amino-3-phenothiazinone III. Methyl 2-amino-3-phenothiazinone-1-carboxylate, *Journal of Organic Chemistry of the USSR*, 1976, pp. 1783-1787, vol. 12, No. 8.

Staiger et al., "Isatoic Anhydride. IV. Reactions with Various Nucleophiles," *The Journal of Organic Chemistry*, 1959, 24 (9), pp. 1214-1219.

Sutton et al., "The Synthesis of Potentially Selective Inhibitors of Dihydroorotate Dehydrogenase. The Utilization of Chemoselective Suzuki Cross-coupling Reactions in a Parallel Synthesis", Tetrahedron Letters (2001) vol. 42, No. 4, pp. 547-551.

* cited by examiner

ANTHRANILIC ACID DERIVATIVES

CROSS REFERENCE TO RELATED APPLICATIONS

This application is a continuation of PCT Application No. PCT/SE2008/050126, filed Jan. 31, 2008, and also claims the benefit of U.S. Provisional Application Ser. No. 60/899,660, filed Feb. 6, 2007, and Swedish Application No. 0700281-9, filed Feb. 6, 2007, all of which are incorporated herein by reference in their entirety and for all purposes.

FIELD OF THE INVENTION

The present invention relates to novel anthranilic acid derivatives, which are stable towards oxidation by human cytochrome P450 and are potent inhibitors of dihydroorotate dehydrogenase (DHODH), to be used for clinical treatment of autoimmune diseases, inflammatory diseases, organ transplant rejection and malignant neoplasia. These compounds and pharmaceutical compositions of this invention are particularly useful for preventing and treating acute and chronic inflammation, rheumatoid arthritis, multiple sclerosis, type-1 diabetes, inflammatory bowel disease, psoriasis, transplant rejection and malignant neoplastic disease. More particularly, the present invention relates to novel derivatives suitable for the treatment of rheumatoid arthritis and transplant rejection.

BACKGROUND OF THE INVENTION

Rheumatoid Arthritis (RA) is a chronic inflammatory disease of unknown cause that leads to pain, stiffness, swelling and limitation in the motion and function of multiple joints. If left untreated, RA can produce serious destruction of joints that frequently leads to permanent disability. RA currently has a worldwide distribution with an estimated prevalence of 0.5 to 1%.

The main symptom of RA is the persistent inflammation of the joints, usually in a symmetric distribution. This inflammation leads to the destruction of cartilage, bone erosion and structural changes in the joint, which may range from minimal joint damage to debilitating disease. Some patients also experience the effects of RA in places other than the joints.

RA is a chronic disorder for which no cure currently exists. The major goals of treatment are to reduce pain and discomfort, prevent deformities, and minimize loss of joint function to maintain a productive and active life. For treatment to be considered successful, inflammation must be suppressed. Many pathways involved in the generation of the disease have been recognized and some of these have been unequivocally identified as important by therapeutic proof of principle studies. Major pharmacological treatments for RA include, but are not limited to, analgesics, non-steroidal anti-inflammatory drugs (NSAIDs), corticosteroids, and disease modifying anti-rheumatic drugs (DMARDs), including biologicals.

NSAIDs are typically given at the onset of symptoms and serve to reduce inflammation and pain thereby improving function. NSAIDs relieve symptoms but do not slow disease progression, so patients will eventually need additional or replacement therapies. Thus, DMARDs are typically added to the treatment regimen soon after diagnosis. The goal of DMARD use is to slow down the progression of disease. Methotrexate (MTX) (Merck Index 12th Ed., #6065) is currently the most commonly prescribed first-line DMARD. However, the administration of MTX has been associated with serious side effects such as skin reactions, pulmonary pneumonitis, gastrointestinal disturbances, hepatotoxicity and renal toxicity. The second leading oral DMARD is leflunomide (ARAVA®). However, as with MTX, leflunomide has been shown to have serious side effects including hepato- and haematological toxicity as well as pulmonary pneumonitis.

A number of biologicals have recently been approved for clinical treatment of RA. These drugs (proteins, e.g., monoclonal antibodies) prevent in general pro-inflammatory cytokines, in particular TNF-α and IL-1, from interacting with their receptors. Biologicals are often added to the treatment regimen once DMARD therapy is no longer adequate, or side effects have become unmanageable. The most commonly prescribed biologicals, e.g., infliximab (REMICADE®), block tissue necrosis factor-alpha (TNF-α), which is a pro-inflammatory cytokine produced by macrophages and lymphocytes. The pro-inflammatory effects of TNF-α suggest that inhibition of TNF-α would be clinically useful in RA. Indeed, clinical trial data has confirmed the efficacy of these TNF inhibitors in relieving the signs and symptoms of RA. However, these biologicals have potentially severe side effects including severe infections, sepsis, tuberculosis and fatal liver toxicity.

Dihydroorotate dehydrogenase (DHODH) catalyzes the conversion of dihydroorotate to orotate concurrent with the reduction of ubiquinone. DHODH controls the rate limiting step in the de novo pyrimidine biosynthesis. DHODH inhibition results in decreased cellular levels of ribonucleotide uridine monophosphate (rUMP), thus arresting proliferating cells in the G1 phase of the cell cycle. The inhibition of de novo pyrimidine nucleotide synthesis is of great interest in view of the observations that lymphocytes seem not to be able to undergo clonal expansion when this pathway is blocked.

Two major compound classes of mammalian DHODH inhibitors have been described in the literature. These are represented by brequinar (Merck Index 12th Ed., #1394), of formula

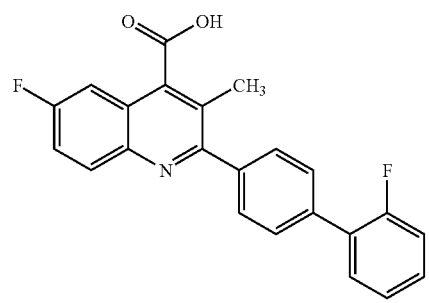

and the active metabolite A771726 of leflunomide, of formula

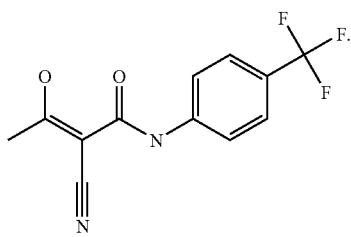

Proof of concept for DHODH inhibition has been established for brequinar. Indeed, biochemical and x-ray crystallographic studies have demonstrated that brequinar is a competitive inhibitor versus the co-factor ubiquinone.

WO 2005/075410 discloses anthranilic acid derivatives of general formula (A)

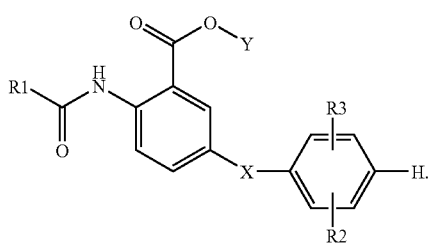

(A)

This PCT application concerns compounds which inhibit DHODH, useful for preventing and treating acute and chronic inflammation, rheumatoid arthritis, multiple sclerosis, type-1 diabetes, inflammatory bowel disease, psoriasis, transplant rejection and malignant neoplastic disease. The type and position of the R2/R3 substitution are stated to be crucial for a strong DHODH inhibition. Compounds wherein R2/R3 are lipophilic substituents with high 1-values in the range of 0.5 to 2 (Kubinyi, 1993) are said to display maximal inhibition. Moreover, monosubstitution, i.e., R3 is hydrogen, is indicated to be superior to di-substitution, the position of the monosubstitution being important for the effect. Thus, in monosubstituted compounds, the ortho-substitution is stated to be superior to meta-substitution, and far superior to substitution in the para-position. In a preferred embodiment of WO 2005/075410, X is CH2, 0, S, CH═CH, OCH2, CH2O or CH2S, and R2 and R3 are the same or different and represent hydrogen or substituents in the 2-, 3- or 5-positions. In a more preferred embodiment of WO 2005/075410, X is $OCH_2$, Y is hydrogen, R2 is a substituent in the ortho-position and is trifluoromethyl, and R3 is hydrogen. In a further preferred embodiment of said application, X is O, Y is hydrogen, and R2 and R3 are substituents in the meta- and meta'-positions, and are trifluoromethyl.

EP0497740 discloses benzyloxyphenyl derivatives of general formula (B)

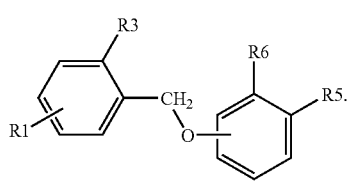

(B)

This patent concerns compounds possessing antihyperproliferative/anti-inflammatory and anticancer activity. In a preferred group of compounds, R1 and R3 are methoxy, and the benzyloxy moiety is in meta-position in respect to R6. R6 is carboxy or an ester group, R5 is hydroxy or acetylamino, especially hydroxy.

EP0815087 discloses trisubstituted phenyl derivatives of general formula (C)

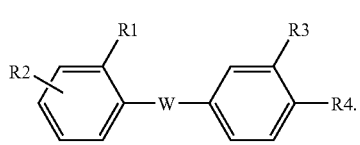

(C)

This patent concerns compounds for the treatment of inflammatory and proliferative skin diseases and cancer. The compounds are to be administered topically or in divided doses up to four times a day. In the most preferred compounds, R1 and R2 are methoxy, W is $CH_2CH_2$, and R3 and R4 together with the phenyl ring form a condensed ring system.

Research Disclosure, 1998, 409(May), P561-P562 (No. 40953) discloses synthetic analogues of the natural product lavendustin A, of general formula (D)

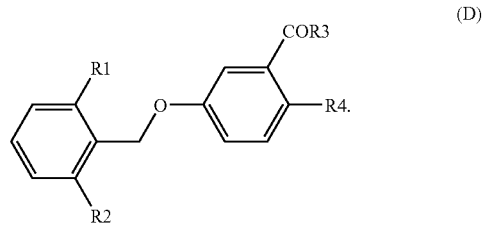

(D)

Compounds are disclosed wherein R1 and R2 are the same or different and represent alkoxy, alkyl or alkenyloxy, R3 is i.a. alkoxy and R4 is i.a. acylamino.

Gennari et al., (1994) reported an anaerobic degradation in soil of 2-nitrophenoxy acids used as herbicides, e.g., acifluorfen, (Merck Index 12th Ed., #111) that gives compound E

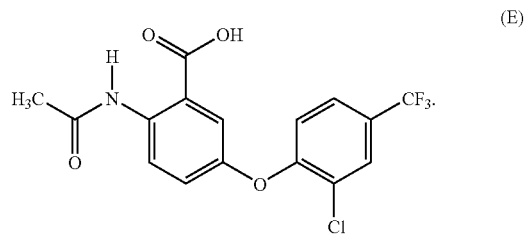

(E)

There is no teaching in the literature disclosing the use of compound E as a pharmaceutical agent.

SUMMARY OF THE INVENTION

A primary objective of the present invention is to provide structurally novel anthranilic acid derivatives, which by virtue of their pharmacological profile, with high potency in experimental models and low level of side effects, are considered to be of value in the treatment of autoimmune diseases, inflammatory diseases, organ transplant rejection and malignant neoplasia. In particular, according to one aspect, the invention aims to provide compounds that show a substantial stability towards oxidation by human cytochrome P450 and that inhibit DHODH.

Furthermore, the invention aims to provide a pharmaceutical composition containing a therapeutically effective amount of a compound according to the invention, as well as the use of a compound of the invention for the treatment and prevention of diseases, in particular diseases where there is an advantage in inhibiting DHODH.

According to an important aspect of the invention, compounds are provided that may be used for preventing and treating, but not restricted to, acute and chronic inflammation, rheumatoid arthritis, multiple sclerosis, type-1 diabetes, inflammatory bowel disease, psoriasis, transplant rejection and malignant neoplastic disease. In one embodiment, the present invention provides compounds suitable for the treatment of rheumatoid arthritis and transplant rejection.

Thus, according to one aspect the present invention provides compounds of formula (I)

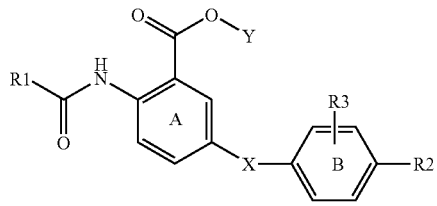

wherein
X is CH=CH, CH$_2$O wherein the oxygen is bound to ring B, or OCH$_2$ wherein the oxygen is bound to ring A;
Y is hydrogen, straight or branched C1-C6 alkyl or a pharmaceutically acceptable inorganic cation;
R1 is ethyl or cyclopropyl; and
R2 and R3 are the same or different and are selected from F, Cl, Br, CF$_3$ and OCF$_3$.

In one particular embodiment of the invention, X is CH$_2$O wherein the oxygen is bound to ring B. In another particular embodiment of the invention, X is OCH$_2$ wherein the oxygen is bound to ring A. In still a further embodiment of the invention, X is CH=CH.

In one embodiment of the invention, R2 is CF$_3$ or OCF$_3$. In one embodiment of the invention, Y is a pharmaceutically acceptable cation selected from e.g., Li$^+$, Na$^+$, K$^+$, Mg$^{2+}$, Ca$^{2+}$ and Zn$^{2+}$. In one embodiment of the invention, in which Y is a divalent cation, the salt contains two anthranilic acid derivative moieties for each cation Y. In another embodiment, in which Y is a divalent cation, the salt comprises one negative monovalent counterion, e.g., a halogen or a bicarbonate (HCO$_3^-$) anion, e.g., Cl$^-$ or Br$^-$, and one anthranilic acid derivative moiety for each cation Y.

In one embodiment of the invention, Y is a straight or branched C1-C6 alkyl group, e.g., a straight or branched C1-C4 alkyl group, or a straight or branched C1-C3 alkyl group.

In one preferred embodiment of the invention, X is CH$_2$O wherein the oxygen is bound to ring B; Y is hydrogen, straight or branched C1-C6 alkyl or a pharmaceutically acceptable inorganic cation; R1 is ethyl or cyclopropyl; and R2 and R3 are the same or different and are selected from F, Cl, Br, CF$_3$ and OCF$_3$.

In one preferred embodiment of the invention, X is CH$_2$O wherein the oxygen is bound to ring B; Y is hydrogen or a pharmaceutically acceptable inorganic cation; R1 is ethyl or cyclopropyl; and R2 and R3 are the same or different and are selected from F, Cl, Br, CF$_3$ and OCF$_3$.

In another preferred embodiment of the invention, X is CH$_2$O wherein the oxygen is bound to ring B; Y is hydrogen, straight or branched CT-C6 alkyl or a pharmaceutically acceptable inorganic cation; R1 is ethyl or cyclopropyl; R2 is CF$_3$ or OCF$_3$; and R3 is F, Cl, Br, CF$_3$ or OCF$_3$.

In still another preferred embodiment of the invention, X is CH2O wherein the oxygen is bound to ring B; Y is hydrogen or a pharmaceutically acceptable inorganic cation; R1 is ethyl or cyclopropyl; R2 is CF$_3$ or OCF$_3$; and R3 is F, Cl, Br, CF$_3$ or OCF$_3$.

Some of the most preferred compounds of formula (I) are:
5-(2-Chloro-4-fluoro-phenoxymethyl)-2-propionylamino-benzoic acid;
5-(2-Chloro-4-trifluoromethoxy-phenoxymethyl)-2-propionylamino-benzoic acid;
5-(2-Bromo-4-chloro-phenoxymethyl)-2-propionylamino-benzoic acid;
5-[(E)-2-(2,4-Bis-trifluoromethyl-phenyl)-vinyl]-2-propionylamino-benzoic acid;
5-[(E)-2-(2-Chloro-4-fluoro-phenyl)-vinyl]-2-propionylamino-benzoic acid;
5-[(E)-2-(2,4-Dichloro-phenyl)-vinyl]-2-propionylamino-benzoic acid; and
5-[(E)-2-(4-Chloro-2-trifluoromethyl-phenyl)-vinyl]-2-(cyclopropanecarbonyl-amino)-benzoic acid.

Further aspects and embodiments of the invention will present themselves to the skilled person in light of the following detailed description and are as defined in the claims.

DETAILED DESCRIPTION OF THE INVENTION

The compounds of formula (I) unexpectedly displayed extraordinary resistance towards oxidation by the human cytochrome P450 enzymes in conjunction with potent inhibition of the DHODH enzyme. In contrast to this, compounds of formula (A) according to the above-mentioned WO 2005/075410, wherein R3 is hydrogen and R2 is ortho or meta, have been found to be extensively metabolized by human cytochrome P450 enzymes, primarily the CYP2C9 isoform. There is no rat or mouse orthologue of the human CYP2C9 enzyme. These in vivo findings are reflected in in vitro liver microsome preparations where T½ is >200 minutes for rat, 150 minutes for mouse and 3 minutes for human. The P450 enzymes exhibit broad substrate specificity and the same oxidation are in general catalyzed to by alternative enzymes in preclinical species. However, for the compounds of this invention, a pronounced across species variation in oxidation activity is seen in vitro in microsomes from various species including human and consequently preclinical in vivo models fail to predict the metabolic and pharmacokinetic behavior of these compounds in human. Therefore, human liver microsomes comprising the important cytochrome P450 enzymes have been used for predicting pharmacokinetic properties of these compounds in human.

Table 1 illustrates the impact of substitution pattern on the metabolic stability and the DHODH inhibitory potency.

TABLE 1

| Compound | Type | X | ortho | meta | para | meta' | R1 | Jurkat IC50 (μM) | $t_{1/2}$ (min) |
|---|---|---|---|---|---|---|---|---|---|
| PA 1 | prior art | OCH2 | CF3 | | | | C-propyl | 0.62 | 3 |
| PA 2 | prior art | CH2O | CF3 | | | | Et | 0.49 | 4 |
| PA 3 | prior art | CH=CH | CF3 | | | | Et | 0.12 | 13 |
| PA 4 | prior art | CH2O | | CF3 | | | Et | 0.43 | 22 |
| PA 5 | prior art | OCH2 | | CF3 | | CF3 | Et | 5.4 | n.d. |
| PA 6 | prior art | CH2O | | CF3 | | CF3 | Et | 1.13 | n.d. |
| INV 1 | Invention | CH2O | CF3 | | CF3 | | Et | 0.6 | stable |
| INV 2 | Invention | CH2O | CF3 | | F | | Et | 0.58 | 236 |

TABLE 1-continued

| Compound | Type | X | ortho | meta | para | meta' | R1 | Jurkat IC50 (µM) | $t_{1/2}$ (min) |
|---|---|---|---|---|---|---|---|---|---|
| INV 3 | Invention | CH2O | CF3 | | Br | | Et | 0.47 | 234 |
| INV 4 | Invention | CH2O | Cl | | CF3 | | Et | 0.42 | stable |
| INV 5 | Invention | CH2O | Cl | | F | | Et | 0.19 | 323 |
| INV 6 | Invention | CH2O | Cl | | Cl | | Et | 0.35 | 199 |
| INV 7 | Invention | CH2O | Br | | CF3 | | Et | 0.49 | 408 |
| INV 8 | Invention | CH2O | Br | | F | | Et | 0.36 | 320 |
| INV 9 | Invention | CH2O | Br | | Cl | | Et | 0.24 | 168 |
| INV 10 | Invention | CH2O | Cl | | OCF3 | | Et | 0.24 | stable |
| INV 11 | Invention | CH═CH | CF3 | | CF3 | | Et | 0.09 | 489 |
| INV 12 | Invention | CH═CH | CF3 | | F | | Et | 0.16 | 159 |
| INV 13 | Invention | CH═CH | CF3 | | Cl | | Et | 0.05 | 105 |
| INV 14 | Invention | CH═CH | F | | F | | Et | 0.24 | 213 |
| INV 15 | Invention | CH═CH | Cl | | F | | Et | 0.035 | 137 |
| INV 16 | Invention | CH═CH | Cl | | Cl | | Et | 0.02 | 110 |
| INV 17 | Invention | CH2O | | CF3 | F | | Et | 0.53 | 104 |
| INV 18 | Invention | CH2O | | CF3 | Cl | | Et | 0.84 | 464 |
| INV 19 | Invention | CH2O | | Cl | F | | Et | 0.42 | 71 |
| INV 20 | Invention | CH2O | | Cl | Br | | Et | 0.73 | 72 |
| INV 21 | Invention | CH2O | | Cl | OCF3 | | Et | 0.89 | 168 |
| INV 22 | Invention | CH2O | | Br | OCF3 | | Et | 0.71 | 198 |
| INV 23 | Invention | CH═CH | | CF3 | F | | Et | 0.75 | 147 |
| INV 24 | Invention | CH═CH | | CF3 | Cl | | Et | 0.57 | 345 |
| INV 25 | Invention | CH═CH | | F | CF3 | | Et | 0.74 | stable |
| INV 26 | Invention | CH═CH | | Cl | F | | Et | 0.75 | 73 |
| INV 27 | Invention | CH═CH | | Cl | Cl | | Et | 0.48 | 115 |
| INV 28 | Invention | CH═CH | | Cl | OCF3 | | Et | 0.6 | n.d. |
| INV 29 | Invention | OCH2 | CF3 | | Cl | | Et | 0.57 | 110 |
| INV 30 | Invention | OCH2 | Br | | CF3 | | Et | 0.59 | 191 |
| INV 31 | Invention | OCH2 | CF3 | | Br | | C-propyl | 0.42 | 232 |
| REF 1 | Reference | CH2O | Cl | | CH3 | | Et | 0.07 | 1 |
| REF 2 | Reference | CH2O | Cl | | OCH3 | | Et | 0.18 | 4 |
| REF 3 | Reference | CH2O | CH3 | | Cl | | Et | 0.39 | 16 |
| REF 4 | Reference | CH2O | OCH3 | | Cl | | Et | 0.99 | 34 |
| REF 5 | Reference | CH2O | CH3 | | CH3 | | Et | 0.51 | 3 |
| REF 6 | Reference | CH2O | | CH3 | Cl | | Et | 0.31 | 16 |
| REF 7 | Reference | OCH2 | OCH3 | | | OCH3 | Et | 3.24 | 4 |
| REF 8 | Reference | 2-acetylamino-5-(2,5-dimethoxy-benzyloxy)-benzoic acid | | | | | | 6.2 | |
| REF 9 | Reference | 2-acetylamino-5-[2-(2,5-dimethoxy-phenyl)-ethyl]-benzoic acid | | | | | | 12 | |
| REF 10 | Reference | 2-Propionylamino-5-(2-trifluoromethyl-benzyloxy)-benzoic acid methyl ester | | | | | | 12.3 | |

Notes:
$t_{1/2}$ equal to "stable" indicates that that no degradation could be confirmed in the assay
n.d. = not determined
Et = ethyl
C-propyl = cyclopropyl In those of the compounds shown in Table 1 that are according to the invention (INV 1-31), "ortho" and "meta" correspond to R3, while "para" corresponds to R2.

As pointed out herein above, one important object of the invention is to provide compounds that show a substantial stability towards oxidation by human cytochrome P450 and that inhibit DHODH.

In order to obtain continuous plasma drug exposure after once-daily administration to human, compounds demonstrating a substantial in vitro metabolic stability towards oxidation by cytochrome P450, e.g., a half-life ($t_{1/2}$) longer than 70 min in the human in vitro system used are preferred. A metabolic stability half-life of longer than 70 minutes corresponds to a predicted hepatic extraction ratio of less than 0.3, which is considered as low according to Rowland et al. (Rowland M and Tozer T. N., (1995), in Clinical Pharmacokinetics Concepts and Applications, third edition, Williams & Wilkins, USA, p. 163).

Thus, by a compound having a "substantial stability towards oxidation by human cytochrome P450" is meant that the compound has a stability towards oxidation by human cytochrome P450 that preferably allows treatment of a mammal subject, such as a human subject, by administration of a therapeutically effective dose only once or twice a day, more preferably by a once-daily administration.

In one embodiment of the invention, compounds according to formula (I) as herein defined are provided having a substantial in vitro metabolic stability towards oxidation by cytochrome P450, e.g., a half-life ($t_{1/2}$) longer than about 70 minutes, or longer than about 100 minutes, longer than about 200 minutes or even longer than about 300 minutes, e.g., a half-life within the range of from 70 to 500 minutes, or 100 to 400 minutes, or even longer, when tested in the human in vitro system as described in the present application.

In another embodiment of the invention, a pharmaceutical composition is provided comprising a therapeutically effective amount of a compound according to formula (I) as herein defined, which compound has a substantial in vitro metabolic stability towards oxidation by cytochrome P450, e.g., a half-life ($t_{1/2}$) longer than about 70 minutes, or longer than about 100 minutes, longer than about 200 minutes or even longer than about 300 minutes, e.g., a half-life within the range of from 70 to 500 minutes, e.g. 100 to 400 minutes, or even longer, when tested in the human in vitro system as described in the present application.

For the purpose of the present invention, "a therapeutically effective amount" should be construed in the conventional sense, i.e., as an amount sufficient to provide a health benefit to the subject being treated. Such a health benefit may be e.g., a curing of the disorder, a slowing down of its progression, or a relief of any symptom of the disorder.

According to one aspect of the invention, there is provided the use of the compounds of the invention for preparing a medicament suitable for the treatment of disorders that are beneficially influenced by inhibiting DHODH.

In one embodiment, the medicament is for the treatment of disorders selected from autoimmune diseases, inflammatory diseases, organ transplant rejection and malignant neoplasia.

In another embodiment, the disorders are selected from acute and chronic inflammation, rheumatoid arthritis, multiple sclerosis, type-1 diabetes, inflammatory bowel disease, psoriasis, transplant rejection and malignant neoplastic disease, in particular rheumatoid arthritis and transplant rejection.

In one embodiment, the invention provides the use of the compounds of the invention for preparing a medicament suitable for the treatment of disorders as mentioned herein above, by daily or bi-daily administration of a therapeutically effective amount of the compounds to a mammal in need of such treatment, more preferably by daily administration.

Synthetic Methods

The compounds of general formula (I) may be prepared e.g., by the following methods:

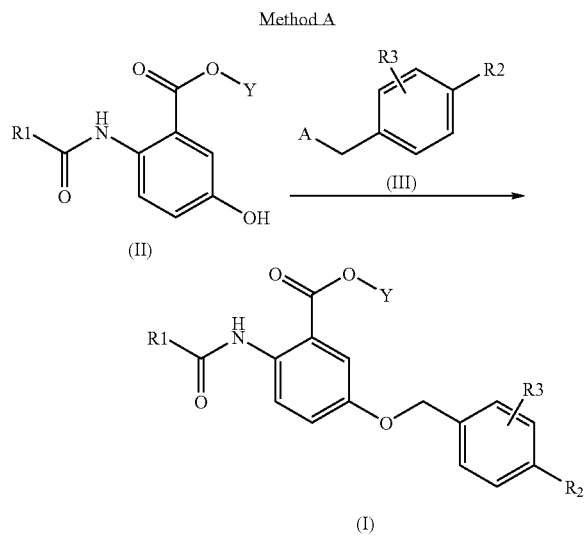

In method A, the compounds of formula I wherein X is $OCH_2$ wherein the oxygen is bound to ring A are prepared by reacting a compound of formula II, with a benzylic reagent wherein A is a leaving group, e.g., bromide, chloride, mesyloxy or tosyloxy.

The reaction may be carried out in a suitable solvent such as a polar aprotic solvent, e.g., acetone, acetonitrile or DMF, in the presence of an alkali metal carbonate, e.g., potassium carbonate. If Y is a C1-C6 alkyl group, the acid function may be obtained by simple alkaline hydrolysis of the ester functionality. The acid function may be converted into the corresponding salt by reaction with a suitable base.

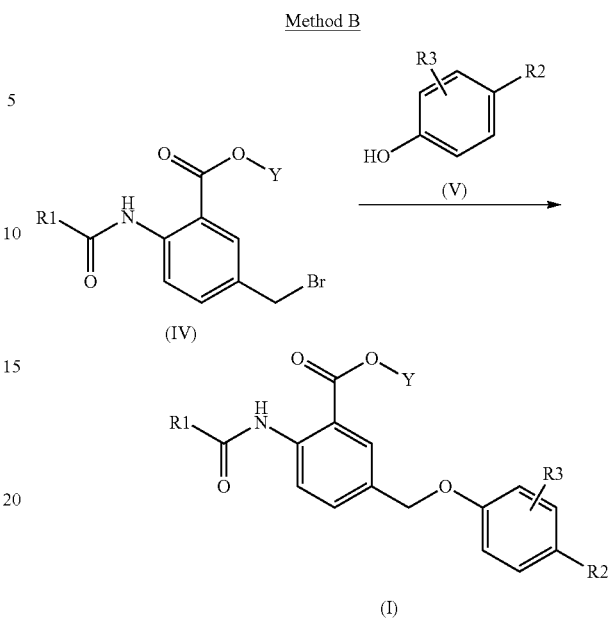

In method B, the compounds of formula I wherein X is $CH_2O$ wherein the oxygen is bound to ring B are prepared by reacting a compound of formula IV with a phenol V in a suitable solvent such as a polar aprotic solvent, e.g., acetone, acetonitrile or DMF, in the presence of an alkali metal carbonate, e.g., potassium carbonate. If Y is a C1-C6 alkyl group, the acid function may be obtained by simple alkaline hydrolysis of the ester functionality. The acid function may be converted into the corresponding salt by reaction with a suitable base.

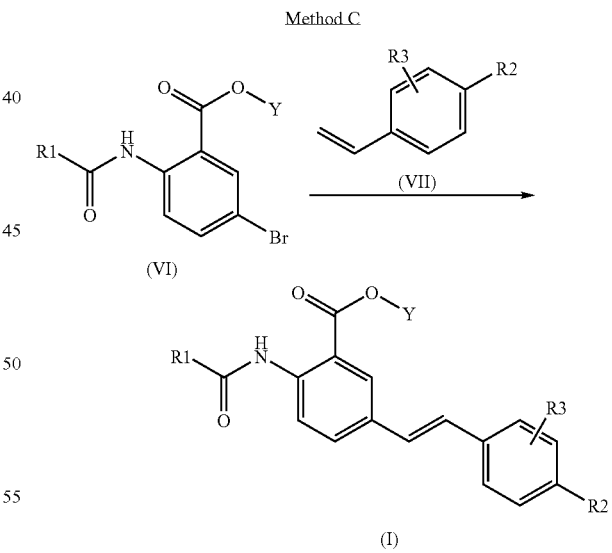

In method C, compounds of formula I wherein X is CH═CH are prepared by reacting a compound of formula VI with a styrene VII (Heck-reaction) with palladium catalysis in a suitable solvent such as a polar aprotic solvent, e.g., DMF, in the presence of an alkali metal carbonate, e.g., potassium carbonate. If Y is a C1-C6 alkyl group, the acid function may be obtained by simple alkaline hydrolysis of the ester functionality. The acid function may be converted into the corresponding salt by reaction with a suitable base.

Method D

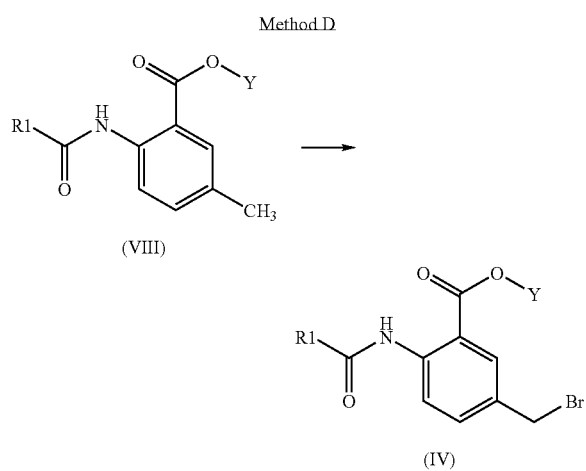

In method D, compounds of formula VIII are transformed to the corresponding 5-benzyl bromide IV by reaction with 1,3-dibromo-5,5-dimethyl hydantoin (CAS No.: 77-48-5) (Patil, S D, Jones C, Nair M G, Galivan J, Maley F, Kisliuk R L, Gaumont Y, Duch D, Ferone R, *J. Med. Chem.*, 1989, 32, 1284-89).

Method E

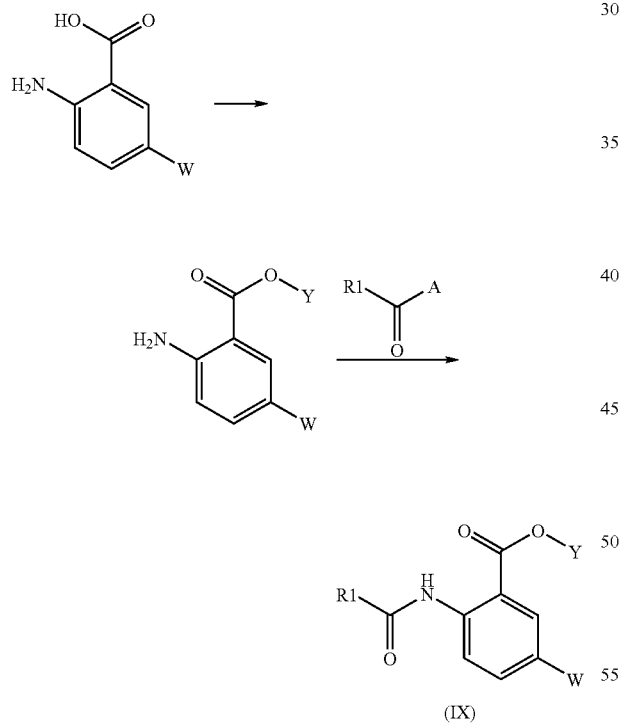

In method E, compounds of the general formula IX (e.g., II (W=OH), VI (W=Br) and VIII (W=CH3)) are prepared from commercially available 5-substituted anthranilic acids. Reaction of such an acid with an anhydrous alcohol in the presence of thionyl chloride (SOCl$_2$, CAS No.: 7719-09-7) provides the anthranilic ester. Suitable acylating reagents to transform the anthranilic ester to the amide (IX) are, for example, acid anhydrides and acyl chlorides (A is a leaving group).

Method F

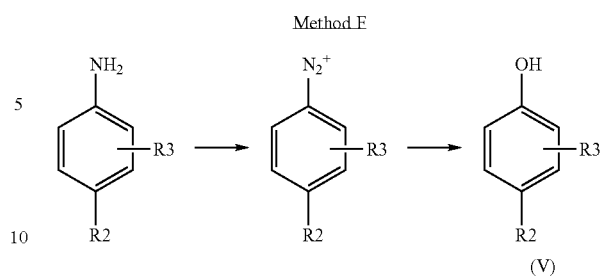

In method F, phenols of the general formula V, e.g., non-commercially available phenols, are prepared from commercially available anilines by diazotation followed by boiling in 33% sulfuric acid.

Synthetic Procedures

In general, nuclear magnetic resonances were recorded at 400 MHz using Bruker ARX 400 spectrometer. The spectra were obtained in CDCl$_3$, CDCl$_3$+TFA or D6-DMSO and the shift scale was referenced to the shift of TMS, defined as 0.00 ppm. Abbreviations used in the description of NMR spectra are: s=singlet, d=doublet, t=triplet, q=quartet, dd=double doublet, dt=double triplet, m=multiplet and b=broad signal. In the Examples below AutoNom Standard was used to generate the compound names.

Example 1

2,4-(Bis-trifluoromethyl)-phenol

Method F

To an ice-cold solution of 2,4-bis(trifluoromethyl)-aniline (1.26 g, 5.50 mmol) in sulphuric acid (33%, 40 ml) was added a solution of sodium nitrite (0.46 g, 6.67 mmol) in water (2 ml). After 3 h at 0° C. urea (0.10 g, 1.67 mmol) was added and the reaction mixture was stirred at 0° C. for an additional ten minutes. The reaction mixture was then added to boiling sulphuric acid (33%, 100 ml) and refluxed for 1 h. The reaction mixture was allowed to reach room temperature and was then extracted with ethyl acetate. The organic phase was washed first with water and then with brine, dried over sodium sulphate, filtered and evaporated to dryness. The crude product was chromatographed on silica gel using heptane/ethyl acetate (4/1) as eluent to give 0.29 g (23%) of the title compound. $^1$H NMR (CDCl$_3$) δ 7.08 (d, 1H), 7.17 (bs, 1H), 7.67 (dd, 1H), 7.80 (d, 1H).

Example 2

5-(2,4-Dichloro-benzyloxy)-2-propionylamino-benzoic acid

Method A

A mixture of 5-hydroxy-2-propionyl-carbonyl-amino-benzoic acid methyl ester (200 mg, 0.90 mmol), 2,4-dichloro-benzyl bromide (235 mg, 0.99 mmol) and potassium carbonate (411 mg, 2.97 mmol) in acetone (5 ml) was heated to reflux. After 4 hours, the reaction mixture was allowed to reach room temperature, was acidified with 1 M HCl and the resulting precipitate collected by filtration, washed with water and dried under vacuum to give pure 5-(2,4-dichloro-benzyloxy)-2-propionylamino-benzoic acid methyl ester (254 mg, 66%). This was hydrolyzed in ethanol (3 mL) and 1.0 M NaOH (3 mL) overnight and then acidified with 1.0 M HCl. The resulting precipitate was collected by filtration, washed with water and dried under vacuum (223 mg, 91%).
1H-NMR (DMSO-d6) δ 1.12 (t, 3H), 2.38 (q, 2H), 5.17 (s, 2H), 7.31 (dd, 1H), 7.49 (dd, 1H), 7.54 (dd, 1H), 7.64 (d, 2H), 7.70 (d, 1H), 8.38 (d, 1H), 10.80 (s, 1H), 13.66 (bs, 1H).

In essentially the same manner the following compounds were obtained from the corresponding starting materials:

5-(4-Bromo-2-trifluoromethyl-benzyloxy)-2-(cyclopropanecarbonyl-amino)-benzoic acid
1H-NMR (DMSO-d6) δ 0.81 (d, 4H), 1.66 (m, 1H), 5.22 (s, 2H), 7.26 (dd, 1H), 7.49 (d, 1H), 7.71 (d, 1H), 7.95 (d, 1H), 8.29 (d, 1H), 10.96 (s, 1H), 13.64 (bs, 1H)

5-(4-Fluoro-2-trifluoromethyl-benzyloxy)-2-propionylamino-benzoic acid
1H-NMR (CDCl3+TFA) δ: 1.35 (t, 3H), 2.62 (q, 2H), 5.27 (s, 2H), 7.31 (dd, 1H), 7.46 (dd, 1H), 7.70-7.74 (m, 2H), 8.58 (d, 1H), 10.77 (s, 1H)

5-(2,4-Bis-trifluoromethyl-benzyloxy)-2-propionylamino-benzoic acid
1H-NMR (DMSO-d6) δ 1.12 (t, 3H), 2.38 (q, 2H), 5.37 (s, 2H), 7.32 (dd, 1H), 7.54 (d, 1H), 8.04 (d, 1H), 8.11 (s, 1H), 8.15 (d, 1H), 8.39 (d, 1H), 10.80 (s, 1H), 13.60 (bs, 1H)

5-(4-Chloro-2-trifluoromethyl-benzyloxy)-2-propionylamino-benzoic acid
1H-NMR (DMSO-d6) δ 1.12 (t, 3H), 2.38 (q, 2H), 5.24 (s, 2H), 7.29 (dd, 1H), 7.51 (d, 1H), 7.78-7.84 (m, 2H), 7.87 (s, 1H), 8.39 (d, 1H), 10.80 (s, 1H), 13.60 (bs, 1H)

5-(2-Chloro-4-fluoro-benzyloxy)-2-propionylamino-benzoic acid
1H-NMR (DMSO-d6) δ 1.12 (t, 3H), 2.38 (q, 2H), 5.14 (s, 2H), 7.26-7.32 (m, 2H), 7.52-7.55 (m, 2H), 7.67 (dd, 1H), 8.39 (d, 1H), 10.80 (s, 1H), 13.60 (bs, 1H)

2-(Cyclopropanecarbonyl-amino)-5-(4-fluoro-2-trifluoromethyl-benzyloxy)-benzoic acid
1H-NMR (DMSO-d6) δ 0.84 (d, 4H), 1.70 (m, 1H), 5.22 (s, 2H), 7.27 (dd, 1H), 7.51 (d, 1H), 7.61 (dt, 1H), 7.71 (dd, 1H), 7.84 (dd, 1H), 8.31 (d, 1H), 11.00 (s, 1H), 13.72 (bs, 1H)

5-(2-Bromo-4-fluoro-benzyloxy)-2-propionylamino-benzoic acid
1H-NMR (DMSO-d6) δ 1.12 (t, 3H), 2.38 (q, 2H), 5.13 (s, 2H), 7.29-7.35 (m, 2H), 7.54 (d, 1H), 7.64-7.70 (m, 2H), 8.38 (d, 1H), 10.80 (s, 1H), 13.68 (bs, 1H)

5-(2-Fluoro-4-trifluoromethyl-benzyloxy)-2-propionylamino-benzoic acid
1H-NMR (DMSO-d6) δ 1.12 (t, 3H), 2.38 (q, 2H), 5.28 (s, 2H), 7.33 (dd, 1H), 7.56 (d, 1H), 7.66 (d, 1H), 7.76 (d, 1H), 7.81 (t, 1H), 8.39 (d, 1H), 10.80 (s, 1H), 13.69 (bs, 1H)

5-(2-Bromo-4-trifluoromethyl-benzyloxy)-2-propionylamino-benzoic acid
1H-NMR (DMSO-d6) δ 1.12 (t, 3H), 2.38 (q, 2H), 5.24 (s, 2H), 7.33 (dd, 1H), 7.56 (d, 1H), 7.80-7.86 (m, 2H), 8.09 (s, 1H), 8.39 (d, 1H), 10.81 (s, 1H), 13.70 (bs, 1H)

5-(4-Chloro-3-trifluoromethyl-benzyloxy)-2-propionylamino-benzoic acid
1H-NMR (DMSO-d6) δ 1.12 (t, 3H), 2.38 (q, 2H), 5.22 (s, 2H), 7.31 (dd, 1H), 7.55 (d, 1H), 7.75-7.79 (m, 2H), 7.96 (s, 1H), 8.39 (d, 1H), 10.80 (s, 1H), 13.69 (bs, 1H)

5-(3,4-Dibromo-benzyloxy)-2-propionylamino-benzoic acid
1H-NMR (DMSO-d6) δ 1.12 (t, 3H), 2.37 (q, 2H), 5.12 (s, 2H), 7.28 (dd, 1H), 7.41 (dd, 1H), 7.53 (d, 1H), 7.79 (d, 1H), 7.86 (d, 1H), 8.39 (d, 1H), 10.85 (s, 1H), 13.68 (bs, 1H)

5-(4-Bromo-3-chloro-benzyloxy)-2-propionylamino-benzoic acid
1H-NMR (DMSO-d6) δ 1.12 (t, 3H), 2.37 (q, 2H), 5.13 (s, 2H), 7.29 (dd, 1H), 7.37 (dd, 1H), 7.53 (d, 1H), 7.73 (d, 1H), 7.80 (d, 1H), 8.39 (d, 1H), 10.84 (s, 1H), 13.69 (bs, 1H)

5-(4-Bromo-2-trifluoromethyl-benzyloxy)-2-propionylamino-benzoic acid
1H-NMR (DMSO-d6) δ 1.11 (t, 3H), 2.37 (q, 2H), 5.22 (s, 2H), 7.27 (dd, 1H), 7.50 (d, 1H), 7.72 (d, 1H), 7.95 (d, 1H), 7.97 (s, 1H), 8.37 (d, 1H), 10.82 (s, 1H), 13.69 (bs, 1H)

5-(2,4-Difluoro-benzyloxy)-2-propionylamino-benzoic acid
1H-NMR (DMSO-d6) δ 1.11 (t, 3H), 2.37 (q, 2H), 5.12 (s, 2H), 7.13 (dt, 1H), 7.27-7.34 (m, 2H), 7.53 (d, 1H), 7.62 (q, 1H), 8.37 (d, 1H), 10.83 (s, 1H), 13.68 (bs, 1H)

5-(4-Chloro-2-fluoro-benzyloxy)-2-propionylamino-benzoic acid
1H-NMR (DMSO-d6) δ 1.11 (t, 3H), 2.37 (q, 2H), 5.14 (s, 2H), 7.29 (dd, 1H), 7.34 (dd, 1H), 7.50 (dd, 1H), 7.53 (d, 1H), 7.59 (t, 1H), 8.37 (d, 1H), 10.82 (s, 1H), 13.68 (bs, 1H)

5-(4-Bromo-2-fluoro-benzyloxy)-2-propionylamino-benzoic acid
1H-NMR (DMSO-d6) δ 1.11 (t, 3H), 2.37 (q, 2H), 5.13 (s, 2H), 7.29 (dd, 1H), 7.46 (dd, 1H), 7.50-7.54 (m, 2H), 7.62 (dd, 1H), 8.37 (d, 1H), 10.81 (s, 1H), 13.66 (bs, 1H)

5-(2-Chloro-4-trifluoromethyl-benzyloxy)-2-propionylamino-benzoic acid 5-(4-Bromo-2-chloro-benzyloxy)-2-propionylamino-benzoic acid 5-(2-Bromo-4-chloro-benzyloxy)-2-propionylamino-benzoic acid 5-(2,4-Dibromo-benzyloxy)-2-propionylamino-benzoic acid 5-(3,4-Bis-trifluoromethyl-benzyloxy)-2-propionylamino-benzoic acid 5-(4-Fluoro-3-trifluoromethyl-benzyloxy)-2-propionylamino-benzoic acid
1H-NMR (DMSO-d6) δ 1.12 (t, 3H), 2.38 (q, 2H), 5.20 (s, 2H), 7.30 (dd, 1H), 7.54 (d, 1H), 7.57 (d, 1H), 7.84-7.87 (m, 1H), 7.89 (d, 1H), 8.39 (d, 1H), 10.81 (s, 1H), 13.66 (bs, 1H)

5-(4-Bromo-3-trifluoromethyl-benzyloxy)-2-propionylamino-benzoic acid 5-(3-Fluoro-4-trifluoromethyl-benzyloxy)-2-propionylamino-benzoic acid
1H-NMR (DMSO-d6) δ 1.12 (t, 3H), 2.38 (q, 2H), 5.24 (s, 2H), 7.31 (dd, 1H), 7.56 (dd, 1H), 7.64-7.68 (m, 2H), 7.71 (s, 1H), 8.40 (d, 1H), 10.81 (s, 1H), 13.67 (bs, 1H)

5-(3,4-Difluoro-benzyloxy)-2-propionylamino-benzoic acid 5-(4-Chloro-3-fluoro-benzyloxy)-2-propionylamino-benzoic acid 5-(4-Bromo-3-fluoro-benzyloxy)-2-propionylamino-benzoic acid 5-(3-Chloro-4-trifluoromethyl-benzyloxy)-2-propionylamino-benzoic acid 5-(3-Chloro-4-fluoro-benzyloxy)-2-propionylamino-benzoic acid
1H-NMR (DMSO-d6) δ 1.12 (t, 3H), 2.37 (q, 2H), 5.11 (s, 2H), 7.28 (dd, 1H), 7.44 (t, 1H), 7.46-7.49 (m, 1H), 7.53 (d, 1H), 7.69 (dd, 1H), 8.38 (d, 1H), 10.80 (s, 1H), 13.66 (bs, 1H)

5-(3,4-Dichloro-benzyloxy)-2-propionylamino-benzoic acid
1H-NMR (DMSO-d6) δ 1.12 (t, 3H), 2.37 (q, 2H), 5.15 (s, 2H), 7.29 (dd, 1H), 7.46 (dd, 1H), 7.53 (d, 1H), 7.67 (d, 1H), 7.74 (dd, 1H), 8.38 (d, 1H), 10.79 (s, 1H), 13.65 (bs, 1H)

5-(3-Bromo-4-trifluoromethyl-benzyloxy)-2-propionylamino-benzoic acid 5-(3-Bromo-4-fluoro-benzyloxy)-2-propionylamino-benzoic acid 5-(3-Bromo-4-chloro-benzyloxy)-2-propionylamino-benzoic acid
1H-NMR (DMSO-d6) δ 1.12 (t, 3H), 2.38 (q, 2H), 5.14 (s, 2H), 7.29 (dd, 1H), 7.50 (dd, 1H), 7.53 (d, 1H), 7.66 (d, 1H), 7.87 (d, 1H), 8.38 (d, 1H), 10.79 (s, 1H), 13.68 (bs, 1H)

5-(3-Chloro-4-trifluoromethoxy-benzyloxy)-2-propionylamino-benzoic acid

1H-NMR (DMSO-d6) δ 1.12 (t, 3H), 2.38 (q, 2H), 5.18 (s, 2H), 7.31 (dd, 1H), 7.55 (d, 1H), 7.58 (dd, 1H), 7.62 (dd, 1H), 7.80 (d, 1H), 8.38 (d, 1H), 10.80 (s, 1H), 13.68 (bs, 1H)

5-(2,4-Bis-trifluoromethyl-benzyloxy)-2-(cyclopropanecarbonyl-amino)-benzoic acid 1H-NMR (DMSO-d6) δ 0.82 (d, 4H), 1.70 (m, 1H), 5.36 (s, 2H), 7.28 (dd, 1H), 7.52 (d, 1H), 8.03 (d, 1H), 8.10 (s, 1H), 8.14 (d, 1H), 8.31 (d, 1H), 11.04 (s, 1H), 13.70 (bs, 1H)

5-(4-Chloro-2-trifluoromethyl-benzyloxy)-2-(cyclopropanecarbonyl-amino)-benzoic acid 1H-NMR (DMSO-d6) δ 0.83 (d, 4H), 1.70 (m, 1H), 5.23 (s, 2H), 7.26 (dd, 1H), 7.50 (d, 1H), 7.78-7.83 (m, 2H), 7.87 (d, 1H), 8.30 (d, 1H), 11.02 (s, 1H), 13.66 (bs, 1H)

2-(Cyclopropanecarbonyl-amino)-5-(2-fluoro-4-trifluoromethyl-benzyloxy)-benzoic acid 1H-NMR (DMSO-d6) δ 0.83 (d, 4H), 1.70 (m, 1H), 5.26 (s, 2H), 7.30 (dd, 1H), 7.55 (d, 1H), 7.64 (d, 1H), 7.74 (d, 1H), 7.80 (t, 1H), 8.31 (d, 1H), 11.02 (s, 1H), 13.69 (bs, 1H)

2-(Cyclopropanecarbonyl-amino)-5-(2,4-difluoro-benzyloxy)-benzoic acid

1H-NMR (DMSO-d6) δ 0.83 (d, 4H), 1.70 (m, 1H), 5.12 (s, 2H), 7.13 (dt, 1H), 7.27 (dd, 1H), 7.31 (dt, 1H), 7.53 (d, 1H), 7.62 (q, 1H), 8.30 (d, 1H), 11.02 (s, 1H), 13.66 (bs, 1H)

5-(4-Chloro-2-fluoro-benzyloxy)-2-(cyclopropanecarbonyl-amino)-benzoic acid

1H-NMR (DMSO-d6) δ 0.82 (d, 4H), 1.70 (m, 1H), 5.14 (s, 2H), 7.27 (dd, 1H), 7.33 (dd, 1H), 7.50 (dd, 1H), 7.52 (d, 1H), 7.59 (t, 1H), 8.30 (d, 1H), 11.02 (s, 1H), 13.67 (bs, 1H)

5-(4-Bromo-2-fluoro-benzyloxy)-2-(cyclopropanecarbonyl-amino)-benzoic acid

1H-NMR (DMSO-d6) δ 0.84 (d, 4H), 1H), 1.70 (m, 1H), 5.13 (s, 2H), 7.27 (dd, 1H), 7.46 (dd, 7.50-7.54 (m, 2H), 7.61 (dd, 1H), 8.30 (d, 1H), 11.02 (s, 1H), 13.68 (bs, 1H)

5-(2-Chloro-4-trifluoromethyl-benzyloxy)-2-(cyclopropanecarbonyl-amino)-benzoic acid 5-(2-Chloro-4-fluoro-benzyloxy)-2-(cyclopropanecarbonyl-amino)-benzoic acid 1H-NMR (DMSO-d6) δ 0.84 (d, 4H), 1.69 (m, 1H), 5.13 (s, 2H), 7.25-7.30 (m, 2H), 7.51-7.54 (m, 2H), 7.66 (dd, 1H), 8.30 (d, 1H), 11.02 (s, 1H), 13.68 (bs, 1H)

2-(Cyclopropanecarbonyl-amino)-5-(2,4-dichloro-benzyloxy)-benzoic acid

1H-NMR (DMSO-d6) δ 0.84 (d, 4H), 1.70 (m, 1H), 5.15 (s, 2H), 7.28 (dd, 1H), 7.48 (dd, 1H), 7.52 (d, 1H), 7.62 (d, 1H), 7.69 (d, 1H), 8.31 (d, 1H), 11.03 (s, 1H), 13.69 (bs, 1H)

5-(4-Bromo-2-chloro-benzyloxy)-2-(cyclopropanecarbonyl-amino)-benzoic acid 5-(2-Bromo-4-trifluoromethyl-benzyloxy)-2-(cyclopropanecarbonyl-amino)-benzoic acid 1H-NMR (DMSO-d6) δ 0.84 (d, 4H), 1.70 (m, 1H), 5.22 (s, 2H), 7.30 (dd, 1H), 7.54 (d, 1H), 7.79-7.84 (m, 2H), 8.07 (s, 1H), 8.32 (d, 1H), 11.03 (s, 1H), 13.70 (bs, 1H)

5-(2-Bromo-4-fluoro-benzyloxy)-2-(cyclopropanecarbonyl-amino)-benzoic acid

1H-NMR (DMSO-d6) δ 0.84 (d, 4H), 1.70 (m, 1H), 5.11 (s, 2H), 7.27 (dd, 1H), 7.32 (dt, 1H), 7.52 (d, 1H), 7.63-7.68 (m, 2H), 8.30 (d, 1H), 11.06 (s, 1H), 13.70 (bs, 1H)

5-(2-Bromo-4-chloro-benzyloxy)-2-(cyclopropanecarbonyl-amino)-benzoic acid 2-(Cyclopropanecarbonyl-amino)-5-(2,4-dibromo-benzyloxy)-benzoic acid 5-(3,4-Bis-trifluoromethyl-benzyloxy)-2-(cyclopropanecarbonyl-amino)-benzoic acid 2-(Cyclopropanecarbonyl-amino)-5-(4-fluoro-3-trifluoromethyl-benzyloxy)-benzoic acid 5-(4-Chloro-3-trifluoromethyl-benzyloxy)-2-(cyclopropanecarbonyl-amino)-benzoic acid 5-(4-Bromo-3-trifluoromethyl-benzyloxy)-2-(cyclopropanecarbonyl-amino)-benzoic acid 2-(Cyclopropanecarbonyl-amino)-5-(3-fluoro-4-trifluoromethyl-benzyloxy)-benzoic acid 2-(Cyclopropanecarbonyl-amino)-5-(3,4-difluoro-benzyloxy)-benzoic acid 5-(4-Chloro-3-fluoro-benzyloxy)-2-(cyclopropanecarbonyl-amino)-benzoic acid 5-(4-Bromo-3-fluoro-benzyloxy)-2-(cyclopropanecarbonyl-amino)-benzoic acid 5-(3-Chloro-4-trifluoromethyl-benzyloxy)-2-(cyclopropanecarbonyl-amino)-benzoic acid 5-(3-Chloro-4-fluoro-benzyloxy)-2-(cyclopropanecarbonyl-amino)-benzoic acid 2-(Cyclopropanecarbonyl-amino)-5-(3,4-dichloro-benzyloxy)-benzoic acid 5-(4-Bromo-3-chloro-benzyloxy)-2-(cyclopropanecarbonyl-amino)-benzoic acid 5-(3-Bromo-4-trifluoromethyl-benzyloxy)-2-(cyclopropanecarbonyl-amino)-benzoic acid 5-(3-Bromo-4-fluoro-benzyloxy)-2-(cyclopropanecarbonyl-amino)-benzoic acid 5-(3-Bromo-4-chloro-benzyloxy)-2-(cyclopropanecarbonyl-amino)-benzoic acid 2-(Cyclopropanecarbonyl-amino)-5-(3,4-dibromo-benzyloxy)-benzoic acid Example 3

5-(2,4-Dichloro-phenoxymethyl)-2-propionylamino-benzoic acid

Method B

A mixture of 5-bromomethyl-2-propionylamino-benzoic acid methyl ester (200 mg, 0.67 mmol), 2,4-dichloro-phenol (119 mg, 0.73 mmol) and potassium carbonate (278 mg, 2.01 mmol) in acetone (5 ml) was heated to reflux. After 4 hours, the reaction mixture was allowed to reach room temperature, was acidified with 1 M HCl and the resulting precipitate collected by filtration, washed with water and dried under vacuum to give pure 5-(2,4-dichloro-phenoxymethyl)-2-propionylamino-benzoic acid methyl ester (184 mg, 72%). This was hydrolyzed in ethanol (3 mL) and 1.0 M NaOH (3 mL) overnight and then acidified with 1.0 M HCl. The resulting precipitate was collected by filtration, washed with water and dried under vacuum (165 mg, 93%). 1H-NMR (DMSO-d6) δ 1.12 (t, 3H), 2.42 (q, 2H), 5.21 (s, 2H), 7.27 (d, 1H), 7.39 (dd, 1H), 7.60 (d, 1H), 7.66 (dd, 1H), 8.09 (d, 1H), 8.53 (d, 1H), 11.18 (s, 1H), 13.71 (bs, 1H).

In essentially the same manner the following compounds were obtained from the corresponding starting materials:

5-(2-Chloro-4-fluoro-phenoxymethyl)-2-propionylamino-benzoic acid

1H-NMR (DMSO-d6) δ 1.12 (t, 3H), 2.41 (q, 2H), 5.17 (s, 2H), 7.19 (dt, 1H), 7.25 (dd, 1H), 7.45 (dd, 1H), 7.66 (dd, 1H), 8.08 (d, 1H), 8.52 (d, 1H), 11.15 (s, 1H), 13.72 (bs, 1H)

5-(2-Chloro-4-trifluoromethyl-phenoxymethyl)-2-propionylamino-benzoic acid

1H-NMR (DMSO-d6) δ 1.12 (t, 3H), 2.42 (q, 2H), 5.30 (s, 2H), 7.43 (d, 1H), 7.70 (m, 2H), 7.86 (d, 1H), 8.11 (d, 1H), 8.54 (d, 1H), 11.16 (s, 1H), 13.75 (bs, 1H)

5-(2-Chloro-4-trifluoromethoxy-phenoxymethyl)-2-propionylamino-benzoic acid

1H-NMR (DMSO-d6) δ 1.12 (t, 3H), 2.42 (q, 2H), 5.22 (s, 2H), 7.32-7.39 (m, 2H), 7.59 (d, 1H), 7.67 (dd, 1H), 8.09 (d, 1H), 8.53 (d, 1H), 11.15 (s, 1H), 13.73 (bs, 1H)

5-(2-Bromo-4-fluoro-phenoxymethyl)-2-propionylamino-benzoic acid

1H-NMR (DMSO-d6) δ 1.13 (t, 3H), 2.43 (q, 2H), 5.18 (s, 2H), 7.24 (d, 1H), 7.58 (d, 1H), 7.68 (dd, 1H), 8.09 (d, 1H), 8.53 (d, 1H), 11.14 (s, 1H), 13.74 (bs, 1H)

5-(2-Bromo-4-chloro-phenoxymethyl)-2-propionylamino-benzoic acid

1H-NMR (DMSO-d6) δ 1.13 (t, 3H), 2.43 (q, 2H), 5.21 (s, 2H), 7.23 (d, 1H), 7.44 (d, 1H), 7.68 (dd, 1H), 7.73 (s, 1H), 8.10 (d, 1H), 8.53 (d, 1H), 11.13 (s, 1H), 13.74 (bs, 1H)

5-(2-Bromo-4-trifluoromethyl-phenoxymethyl)-2-propionylamino-benzoic acid

1H-NMR (DMSO-d6) δ 1.13 (t, 3H), 2.43 (q, 2H), 5.31 (s, 2H), 7.40 (d, 1H), 7.70 (dd, 1H), 7.76 (d, 1H), 7.99 (s, 1H), 8.12 (d, 1H), 8.54 (d, 1H), 11.15 (s, 1H), 13.77 (bs, 1H)

5-(4-Bromo-2-trifluoromethyl-phenoxymethyl)-2-propionylamino-benzoic acid

1H-NMR (DMSO-d6) δ 1.13 (t, 3H), 2.42 (q, 2H), 5.28 (s, 2H), 7.34 (d, 1H), 7.63 (dd, 1H), 7.79 (s, 1H), 7.84 (d, 1H), 8.09 (d, 1H), 8.52 (d, 1H), 11.12 (s, 1H), 13.70 (bs, 1H)

5-(2,4-Bis-trifluoromethyl-phenoxymethyl)-2-propionylamino-benzoic acid

1H-NMR (DMSO-d6) δ 1.13 (t, 3H), 2.42 (q, 2H), 5.39 (s, 2H), 7.57 (d, 1H), 7.65 (dd, 1H), 7.93 (d, 1H), 8.06 (dd, 1H), 8.12 (d, 1H), 8.54 (d, 1H), 11.13 (s, 1H), 13.78 (bs, 1H)

5-(4-Fluoro-2-trifluoromethyl-phenoxymethyl)-2-propionylamino-benzoic acid

1H-NMR (DMSO-d6) δ 1.13 (t, 3H), 2.42 (q, 2H), 5.26 (s, 2H), 7.39 (dd, 1H), 7.51-7.57 (m, 2H), 7.63 (dd, 1H), 8.10 (d, 1H), 8.53 (d, 1H), 11.16 (s, 1H), 13.70 (bs, 1H)

2-(Cyclopropanecarbonyl-amino)-5-(4-fluoro-2-trifluoromethyl-phenoxymethyl)-benzoic acid 1H-NMR (DMSO-d6) δ 0.87 (d, 4H), 1.73 (m, 1H), 5.25 (s, 2H), 7.39 (dd, 1H), 7.40-7.57 (m, 2H), 7.61 (dd, 1H), 8.09 (d, 1H), 8.46 (d, 1H), 11.44 (s, 1H), 13.71 (bs, 1H)

5-(2-Chloro-4-fluoro-phenoxymethyl)-2-(cyclopropanecarbonyl-amino)-benzoic acid

1H-NMR (DMSO-d6) δ 0.87 (d, 4H), 1.73 (m, 1H), 5.18 (s, 2H), 7.20 (dt, 1H), 7.27 (t, 1H), 7.46 dd, 1H), 7.64 (dd, 1H), 8.09 (d, 1H), 8.46 (d, 1H), 11.41 (s, 1H), 13.74 (bs, 1H)

5-(2-Chloro-4-trifluoromethyl-phenoxymethyl)-2-(cyclopropanecarbonyl-amino)-benzoic acid 1H-NMR (DMSO-d6) δ 0.87 (d, 4H), 1.73 (m, 1H), 5.31 (s, 2H), 7.44 (d, 1H), 7.67 (dd, 1H), 7.72 (dd, 1H), 7.87 (d, 1H), 8.12 (d, 1H), 8.47 (d, 1H), 11.43 (s, 1H), 13.75 (bs, 1H)

5-(2-Chloro-4-trifluoromethoxy-phenoxymethyl)-2-(cyclopropanecarbonyl-amino)-benzoic acid 1H-NMR (DMSO-d6) δ 0.88 (d, 4H), 1.74 (m, 1H), 5.23 (s, 2H), 7.33-7.40 (m, 2H), 7.61 (d, 1H), 7.66 (dd, 1H), 8.10 (d, 1H), 8.47 (d, 1H), 11.41 (s, 1H), 13.76 (bs, 1H)

2-(Cyclopropanecarbonyl-amino)-5-(2,4-dichloro-phenoxymethyl)-benzoic acid

1H-NMR (DMSO-d6) δ 0.87 (d, 4H), 1.73 (m, 1H), 5.21 (s, 2H), 7.27 (d, 1H), 7.39 (dd, 1H), 7.60 (d, 1H), 7.65 (dd, 1H), 8.09 (d, 1H), 8.47 (d, 1H), 11.37 (s, 1H), 13.74 (bs, 1H)

5-(4-Fluoro-3-trifluoromethyl-phenoxymethyl)-2-propionylamino-benzoic acid

1H-NMR (DMSO-d6) δ 1.14 (t, 3H), 2.42 (q, 2H), 5.16 (s, 2H), 7.35-7.39 (m, 2H), 7.45 (t, 1H), 7.67 (dd, 1H), 8.07 (d, 1H), 8.53 (d, 1H), 11.18 (s, 1H), 13.73 (bs, 1H)

5-(4-Chloro-3-trifluoromethyl-phenoxymethyl)-2-propionylamino-benzoic acid

1H-NMR (DMSO-d6) δ 1.12 (t, 3H), 2.41 (q, 2H), 5.19 (s, 2H), 7.34 (dd, 1H), 7.44 (d, 1H), 7.65 (d, 1H), 7.67 (dd, 1H), 8.07 (d, 1H), 8.53 (d, 1H), 11.17 (s, 1H), 13.76 (bs, 1H)

5-(3-Chloro-4-fluoro-phenoxymethyl)-2-propionylamino-benzoic acid

1H-NMR (DMSO-d6) δ 1.12 (t, 3H), 2.42 (q, 2H), 5.09 (s, 2H), 7.01 (dt, 1H), 7.26 (dd, 1H), 7.34 (t, 1H), 7.65 (dd, 1H), 8.04 (d, 1H), 8.53 (d, 1H), 11.14 (s, 1H), 13.73 (bs, 1H)

5-(3-Bromo-4-trifluoromethoxy-phenoxymethyl)-2-propionylamino-benzoic acid

1H-NMR (DMSO-d6) δ 1.13 (t, 3H), 2.42 (q, 2H), 5.15 (s, 2H), 7.14 (d, 1H), 7.46-7.49 (m, 2H), 7.67 (dd, 1H), 8.07 (d, 1H), 8.54 (d, 1H), 11.16 (s, 1H), 13.74 (bs, 1H)

5-(4-Bromo-3-chloro-phenoxymethyl)-2-propionylamino-benzoic acid

1H-NMR (DMSO-d6) δ 1.13 (t, 3H), 2.42 (q, 2H), 5.13 (s, 2H), 6.98 (d, 1H), 7.35 (s, 1H), 7.66 (d, 2H), 8.05 (d, 1H), 8.53 (d, 1H), 11.17 (s, 1H), 13.76 (bs, 1H)

5-(3-Chloro-4-trifluoromethoxy-phenoxymethyl)-2-propionylamino-benzoic acid

1H-NMR (DMSO-d6) δ 1.13 (t, 3H), 2.42 (q, 2H), 5.16 (s, 2H), 7.11 (d, 1H), 7.38 (s, 1H), 7.51 (d, 1H), 7.68 (dd, 1H), 8.07 (d, 1H), 8.54 (d, 1H), 11.14 (s, 1H), 13.75 (bs, 1H)

5-(3-Chloro-4-fluoro-phenoxymethyl)-2-(cyclopropanecarbonyl-amino)-benzoic acid

1H-NMR (DMSO-d6) δ 0.87 (d, 4H), 1.73 (m, 1H), 5.10 (s, 2H), 7.03 (dt, 1H), 7.28 (dd, 1H), 7.35 (t, 1H), 7.64 (dd, 1H), 8.05 (d, 1H), 8.48 (d, 1H), 11.38 (s, 1H), 13.74 (bs, 1H)

2-(Cyclopropanecarbonyl-amino)-5-(4-fluoro-3-trifluoromethyl-phenoxymethyl)-benzoic acid 1H-NMR (DMSO-d6) δ 0.87 (d, 4H), 1.73 (m, 1H), 5.17 (s, 2H), 7.37-7.40 (m, 2H), 7.46 (t, 1H), 8.08 (d, 1H), 8.47 (d, 1H), 11.41 (s, 1H), 13.75 (bs, 1H)

5-(4-Chloro-2-trifluoromethyl-phenoxymethyl)-2-propionylamino-benzoic acid 5-(2-Fluoro-4-trifluoromethyl-phenoxymethyl)-2-propionylamino-benzoic acid 5-(2,4-Difluoro-phenoxymethyl)-2-propionylamino-benzoic acid 1H-NMR (DMSO-d6) δ 1.13 (t, 3H), 2.42 (q, 2H), 5.15 (s, 2H), 7.03 (tt, 1H), 7.25-7.33 (m, 2H), 7.65 (dd, 1H), 8.06 (d, 1H), 8.53 (d, 1H), 11.27 (s, 1H), 13.72 (bs, 1H)

5-(4-Chloro-2-fluoro-phenoxymethyl)-2-propionylamino-benzoic acid

1H-NMR (DMSO-d6) δ 1.13 (t, 3H), 2.42 (q, 2H), 5.18 (s, 2H), 7.23 (ddd, 1H), 7.29 (t, 1H), 7.46 (dd, 1H), 7.65 (dd, 1H), 8.07 (d, 1H), 8.53 (d, 1H), 11.24 (s, 1H), 13.77 (bs, 1H)

5-(4-Bromo-2-fluoro-phenoxymethyl)-2-propionylamino-benzoic acid

1H-NMR (DMSO-d6) δ 1.13 (t, 3H), 2.42 (q, 2H), 5.17 (s, 2H), 7.24 (t, 1H), 7.35 (ddd, 1H), 7.56 (dd, 1H), 7.65 (dd, 1H), 8.07 (d, 1H), 8.53 (d, 1H), 11.23 (s, 1H), 13.74 (bs, 1H)

5-(4-Bromo-2-chloro-phenoxymethyl)-2-propionylamino-benzoic acid

1H-NMR (DMSO-d6) δ 1.13 (t, 3H), 2.42 (q, 2H), 5.21 (s, 2H), 7.21 (d, 1H), 7.50 (dd, 1H), 7.66 (dd, 1H), 7.69 (d, 1H), 8.09 (d, 1H), 8.53 (d, 1H), 11.16 (s, 1H), 13.77 (bs, 1H)

5-(2,4-Dibromo-phenoxymethyl)-2-propionylamino-benzoic acid

1H-NMR (DMSO-d6) δ 1.13 (t, 3H), 2.42 (q, 2H), 5.21 (s, 2H), 7.18 (d, 1H), 7.54 (dd, 1H), 7.67 (dd, 1H), 7.82 (d, 1H), 8.09 (d, 1H), 8.53 (d, 1H), 11.18 (s, 1H), 13.73 (bs, 1H)

5-(3,4-Bis-trifluoromethyl-phenoxymethyl)-2-propionylamino-benzoic acid 5-(4-Bromo-3-trifluoromethyl-phenoxymethyl)-2-propionylamino-benzoic acid 5-(3-Fluoro-4-trifluoromethyl-phenoxymethyl)-2-propionylamino-benzoic acid 5-(3,4-Difluoro-phenoxymethyl)-2-propionylamino-benzoic acid 5-(4-Chloro-3-fluoro-phenoxymethyl)-2-propionylamino-benzoic acid 5-(4-Bromo-3-fluoro-phenoxymethyl)-2-propionylamino-benzoic acid 5-(3-Chloro-4-trifluoromethyl-phenoxymethyl)-2-propionylamino-benzoic acid 5-(3,4-Dichloro-phenoxymethyl)-2-propionylamino-benzoic acid 5-(3-Bromo-4-trifluoromethyl-phenoxymethyl)-2-propionylamino-benzoic acid 5-(3-Bromo-4-fluoro-phenoxymethyl)-2-propionylamino-benzoic acid 5-(3-Bromo-4-chloro-phenoxymethyl)-2-propionylamino-benzoic acid 5-(3,4-Dibromo-phenoxymethyl)-2-propionylamino-benzoic acid 5-(2,4-Bis-trifluoromethyl-phenoxymethyl)-2-(cyclopropanecarbonyl-amino)-benzoic acid 1H-NMR (DMSO-d6) δ 0.87 (d, 4H), 1.73 (m, 1H), 5.39 (s, 2H), 7.57 (d, 1H), 7.63 (dd, 1H), 7.94 (d, 1H), 8.06 (dd, 1H), 8.12 (d, 1H), 8.48 (d, 1H), 11.41 (s, 1H), 13.72 (bs, 1H)

5-(4-Chloro-2-trifluoromethyl-phenoxymethyl)-2-(cyclopropanecarbonyl-amino)-benzoic acid 5-(4-Bromo-2-trifluoromethyl-phenoxymethyl)-2-(cyclopropanecarbonyl-amino)-benzoic acid 1H-NMR (DMSO-d6) δ 0.87 (d, 4H), 1.73 (m, 1H), 5.28 (s, 2H), 7.34 (d, 1H), 7.61 (dd, 1H), 7.78 (d, 1H), 7.84 (dd, 1H), 8.09 (d, 1H), 8.46 (d, 1H), 11.40 (s, 1H), 13.70 (bs, 1H)

2-(Cyclopropanecarbonyl-amino)-5-(2-fluoro-4-trifluoromethyl-phenoxymethyl)-benzoic acid 2-(Cyclopropanecarbonyl-amino)-5-(2,4-difluoro-phenoxymethyl)-benzoic acid 1H-NMR (DMSO-d6) δ 0.87 (d, 4H), 1.73 (m, 1H), 5.15 (s, 2H), 7.02 (tt, 1H), 7.25-7.33 (m, 2H), 7.64 (dd, 1H), 8.06 (dd, 1H), 8.47 (d, 1H), 11.39 (s, 1H), 13.76 (bs, 1H)

5-(4-Chloro-2-fluoro-phenoxymethyl)-2-(cyclopropanecarbonyl-amino)-benzoic acid

1H-NMR (DMSO-d6) δ 0.87 (d, 4H), 1.73 (m, 1H), 5.18 (s, 2H), 7.23 (d, 1H), 7.29 (t, 1H), 7.46 (dd, 1H), 7.64 (dd, 1H), 8.07 (d, 1H), 8.47 (d, 1H), 11.43 (s, 1H), 13.73 (bs, 1H)

5-(4-Bromo-2-fluoro-phenoxymethyl)-2-(cyclopropanecarbonyl-amino)-benzoic acid

1H-NMR (DMSO-d6) δ 0.87 (d, 4H), 1.73 (m, 1H), 5.17 (s, 2H), 7.24 (t, 1H), 7.35 (dt, 1H), 7.56 (dd, 1H), 7.64 (dd, 1H), 8.07 (d, 1H), 8.47 (d, 1H), 11.44 (s, 1H), 13.75 (bs, 1H)

5-(4-Bromo-2-chloro-phenoxymethyl)-2-(cyclopropanecarbonyl-amino)-benzoic acid

1H-NMR (DMSO-d6) δ 0.87 (d, 4H), 1.73 (m, 1H), 5.21 (s, 2H), 7.22 (d, 1H), 7.50 (dd, 1H), 7.65 (dd, 1H), 7.69 (d, 1H), 8.09 (d, 1H), 8.47 (d, 1H), 11.39 (s, 1H), 13.74 (bs, 1H)

5-(2-Bromo-4-trifluoromethyl-phenoxymethyl)-2-(cyclopropanecarbonyl-amino)-benzoic acid 1H-NMR (DMSO-d6) δ 0.87 (d, 4H), 1.73 (m, 1H), 5.31 (s, 2H), 7.39 (d, 1H), 7.67 (dd, 1H), 7.75 (dd, 1H), 7.98 (d, 1H), 8.12 (d, 1H), 8.48 (d, 1H), 11.42 (s, 1H), 13.73 (bs, 1H)

5-(2-Bromo-4-fluoro-phenoxymethyl)-2-(cyclopropanecarbonyl-amino)-benzoic acid

1H-NMR (DMSO-d6) δ 0.87 (d, 4H), 1.73 (m, 1H), 5.18 (s, 2H), 7.23-7.27 (m, 2H), 7.58 (dd, 1H), 7.66 (dd, 1H), 8.10 (d, 1H), 8.47 (d, 1H), 11.39 (s, 1H), 13.73 (bs, 1H)

5-(2-Bromo-4-chloro-phenoxymethyl)-2-(cyclopropanecarbonyl-amino)-benzoic acid

1H-NMR (DMSO-d6) δ 0.87 (d, 4H), 1.73 (m, 1H), 5.21 (s, 2H), 7.24 (d, 1H), 7.43 (dd, 1H), 7.65 (dd, 1H), 7.72 (d, 1H), 8.10 (d, 1H), 8.47 (d, 1H), 11.38 (s, 1H), 13.75 (bs, 1H)

2-(Cyclopropanecarbonyl-amino)-5-(2,4-dibromo-phenoxymethyl)-benzoic acid

1H-NMR (DMSO-d6) δ 0.87 (d, 4H), 1.73 (m, 1H), 5.20 (s, 2H), 7.18 (d, 1H), 7.54 (dd, 1H), 7.65 (dd, 1H), 7.81 (d, 1H), 8.09 (d, 1H), 8.47 (d, 1H), 11.37 (s, 1H), 13.74 (bs, 1H)

5-(2-Chloro-4-trifluoromethoxy-phenoxymethyl)-2-(cyclopropanecarbonyl-amino)-benzoic acid 5-(3,4-Bis-trifluoromethyl-phenoxymethyl)-2-(cyclopropanecarbonyl-amino)-benzoic acid 5-(4-Chloro-3-trifluoromethyl-phenoxymethyl)-2-(cyclopropanecarbonyl-amino)-benzoic acid 5-(4-Bromo-3-trifluoromethyl-phenoxymethyl)-2-(cyclopropanecarbonyl-amino)-benzoic acid 2-(Cyclopropanecarbonyl-amino)-5-(3-fluoro-4-trifluoromethyl-phenoxymethyl)-benzoic acid 2-(Cyclopropanecarbonyl-amino)-5-(3,4-difluoro-phenoxymethyl)-benzoic acid 5-(4-Chloro-3-fluoro-phenoxymethyl)-2-(cyclopropanecarbonyl-amino)-benzoic acid 5-(4-Bromo-3-fluoro-phenoxymethyl)-2-(cyclopropanecarbonyl-amino)-benzoic acid 5-(3-Chloro-4-trifluoromethyl-phenoxymethyl)-2-(cyclopropanecarbonyl-amino)-benzoic acid 2-(Cyclopropanecarbonyl-amino)-5-(3,4-dichloro-phenoxymethyl)-benzoic acid 5-(4-Bromo-3-chloro-phenoxymethyl)-2-(cyclopropanecarbonyl-amino)-benzoic acid 5-(3-Bromo-4-trifluoromethyl-phenoxymethyl)-2-(cyclopropanecarbonyl-amino)-benzoic acid 5-(3-Bromo-4-fluoro-phenoxymethyl)-2-(cyclopropanecarbonyl-amino)-benzoic acid 5-(3-Bromo-4-chloro-phenoxymethyl)-2-(cyclopropanecarbonyl-amino)-benzoic acid 2-(Cyclopropanecarbonyl-amino)-5-(3,4-dibromo-phenoxymethyl)-benzoic acid Example 4

5-[(E)-2-(2,4-Dichloro-phenyl)-vinyl]-2-propionylamino-benzoic acid

Method C

A mixture of 5-bromomethyl-2-propionylamino-benzoic acid methyl ester (172 mg, 0.60 mmol), 2,4-dichloro-1-vinyl-benzene (125 mg, 0.72 mmol), potassium carbonate (100 mg, 0.66 mmol), tri-butyl amine (160 μl, 0.66 mmol) and bis(tri-phenyl-phosphino)palladium (II) di-chloride in DMF (3 ml) was heated to 130° C. After 30 minutes, the reaction mixture was allowed to reach room temperature, acidified with 2 M HCl and the resulting precipitate collected by filtration, washed with water and dried under vacuum to give crude 5-[(E)-2-(2,4-dichloro-phenyl)-vinyl]-2-propionylamino-benzoic acid methyl ester. This was hydrolyzed in ethanol (3 mL) and 1.0 M NaOH (3 mL) overnight and then acidified with 1.0 M HCl. The resulting precipitate was collected by filtration, washed with water and dried under vacuum (136 mg, 62% total yield). 1H-NMR (DMSO-d6) δ 1.14 (t, 3H), 2.43 (q, 2H), 7.32 (d, 1H), 7.37 (d, 1H), 7.44 (dd, 1H), 7.63 (d, 1H), 7.87-7.91 (m, 1H), 8.17 (d, 1H), 8.57 (d, 1H), 11.19 (s, 1H), 13.80 (bs, 1H)

In essentially the same manner the following compounds were obtained from the corresponding starting materials:

5-[(E)-2-(4-Fluoro-2-trifluoromethyl-phenyl)-vinyl]-2-propionylamino-benzoic acid
    1H-NMR (DMSO-d6) δ 1.14 (t, 3H), 2.44 (q, 2H), 7.25 (dd, 1H), 7.36 (d, 1H), 7.62 (dt, 1H), 7.65 (dd, 1H), 7.85 (dd, 1H), 8.06 (dd, 1H), 8.16 (d, 1H), 8.57 (d, 1H), 11.20 (s, 1H), 13.79 (bs, 1H)

5-[(E)-2-(2,4-Bis-trifluoromethyl-phenyl)-vinyl]-2-propionylamino-benzoic acid
    1H-NMR (DMSO-d6) δ 1.14 (t, 3H), 2.45 (q, 2H), 7.33 (dd, 1H), 7.59 (d, 1H), 7.93 (dd, 1H), 8.03 (s, 1H), 8.09 (d, 1H), 8.21 (d, 1H), 8.26 (d, 1H), 8.60 (d, 1H), 11.22 (s, 1H), 13.83 (bs, 1H)

5-[(E)-2-(2-Chloro-4-fluoro-phenyl)-vinyl]-2-propionylamino-benzoic acid
    1H-NMR (DMSO-d6) δ 1.14 (t, 3H), 2.44 (q, 2H), 7.26-7.34 (m, 3H), 7.49 (dd, 1H), 7.90 (dd, 1H), 7.94 (dd, 1H), 8.16 (d, 1H), 8.57 (d, 1H), 11.17 (s, 1H), 13.75 (bs, 1H)

5-[(E)-2-(2,4-Difluoro-phenyl)-vinyl]-2-propionylamino-benzoic acid
    1H-NMR (DMSO-d6) δ 1.14 (t, 3H), 2.44 (q, 2H), 7.14 (dt, 1H), 7.20 (d, 1H), 7.27-7.34 (m, 2H), 7.86 (q, 1H), 7.90 (dd, 1H), 8.15 (d, 1H), 8.56 (d, 1H), 11.16 (s, 1H), 13.79 (bs, 1H)

5-[(E)-2-(4-Chloro-2-trifluoromethyl-phenyl)-vinyl]-2-propionylamino-benzoic acid
    1H-NMR (DMSO-d6) δ 1.14 (t, 3H), 2.44 (q, 2H), 7.24 (dd, 1H), 7.43 (d, 1H), 7.77-7.80 (m, 2H), 7.86 (dd, 1H), 8.04 (d, 1H), 8.16 (d, 1H), 8.58 (d, 1H), 11.19 (s, 1H), 13.81 (bs, 1H)

5-[(E)-2-(2-Fluoro-4-trifluoromethyl-phenyl)-vinyl]-2-propionylamino-benzoic acid
    1H-NMR (DMSO-d6) δ 1.14 (t, 3H), 2.44 (q, 2H), 7.30 (d, 1H), 7.53 (d, 1H), 7.61 (d, 1H), 7.71 (d, 1H), 7.97 (dd, 1H), 8.04 (t, 1H), 8.21 (d, 1H), 8.58 (d, 1H), 11.20 (s, 1H), 13.81 (bs, 1H)

2-(Cyclopropanecarbonyl-amino)-5-[(E)-2-(4-fluoro-2-trifluoromethyl-phenyl)-vinyl]-benzoic acid
    1H-NMR (DMSO-d6) δ 0.89 (d, 4H), 1.75 (m, 1H), 7.27 (dd, 1H), 7.37 (d, 1H), 7.61 (dt, 1H), 7.65 (dd, 1H), 7.85 (d, 1H), 8.07 (dd, 1H), 8.16 (d, 1H), 8.51 (d, 1H), 11.40 (s, 1H), 13.82 (bs, 1H)

5-[(E)-2-(4-Chloro-2-trifluoromethyl-phenyl)-vinyl]-2-(cyclopropanecarbonyl-amino)-benzoic acid
    1H-NMR (DMSO-d6) δ 0.89 (d, 4H), 1.75 (m, 1H), 7.24 (dd, 1H), 7.44 (d, 1H), 7.78-7.81 (m, 2H), 7.85 (dd, 1H), 8.04 (d, 1H), 8.17 (d, 1H), 8.51 (d, 1H), 11.41 (s, 1H), 13.86 (bs, 1H)

5-[(E)-2-(4-Chloro-3-trifluoromethyl-phenyl)-vinyl]-2-propionylamino-benzoic acid
    1H-NMR (DMSO-d6) δ 1.14 (t, 3H), 2.44 (q, 2H), 7.35 (d, 1H), 7.51 (d, 1H), 7.73 (d, 1H), 7.89 (dd, 1H), 7.94 (dd, 1H), 8.09 (d, 1H), 8.23 (d, 1H), 8.57 (d, 1H), 11.18 (s, 1H), 13.78 (bs, 1H)

5-[(E)-2-(4-Fluoro-3-trifluoromethyl-phenyl)-vinyl]-2-propionylamino-benzoic acid
    1H-NMR (DMSO-d6) δ 1.14 (t, 3H), 2.44 (q, 2H), 7.33 (d, 1H), 7.43 (d, 1H), 7.53 (dd, 1H), 7.86 (dd, 1H), 7.98 (m, 1H), 8.02 (d, 1H), 8.21 (d, 1H), 8.56 (d, 1H), 11.17 (s, 1H), 13.76 (bs, 1H)

5-[(E)-2-(3-Chloro-4-fluoro-phenyl)-vinyl]-2-propionylamino-benzoic acid
    1H-NMR (DMSO-d6) δ 1.14 (t, 3H), 2.44 (q, 2H), 7.22 (d, 1H), 7.34 (d, 1H), 7.43 (t, 1H), 7.62 (m, 1H), 7.84 (dd, 1H), 7.88 (dd, 1H), 8.17 (d, 1H), 8.55 (d, 1H), 11.16 (s, 1H), 13.78 (bs, 1H)

5-[(E)-2-(3-Fluoro-4-trifluoromethyl-phenyl)-vinyl]-2-propionylamino-benzoic acid
    1H-NMR (DMSO-d6) δ 1.14 (t, 3H), 2.44 (q, 2H), 7.32 (d, 1H), 7.55 (d, 1H), 7.62 (d, 1H), 7.74-7.80 (m, 2H), 7.90 (dd, 1H), 8.22 (d, 1H), 8.58 (d, 1H), 11.20 (s, 1H), 13.81 (bs, 1H)

5-[(E)-2-(3-Chloro-4-trifluoromethoxy-phenyl)-vinyl]-2-propionylamino-benzoic acid
    1H-NMR (DMSO-d6) δ 1.14 (t, 3H), 2.44 (q, 2H), 7.24 (d, 1H), 7.42 (d, 1H), 7.56 (d, 1H), 7.68 (dd, 1H), 7.86 (dd, 1H), 7.96 (d, 1H), 8.19 (d, 1H), 8.56 (d, 1H), 11.18 (s, 1H), 13.77 (bs, 1H)

5-[(E)-2-(3,4-Dichloro-phenyl)-vinyl]-2-propionylamino-benzoic acid
    1H-NMR (DMSO-d6) δ 1.14 (t, 3H), 2.44 (q, 2H), 7.22 (d, 1H), 7.42 (d, 1H), 7.59-7.64 (m, 2H), 7.86 (dd, 1H), 7.91 (d, 1H), 8.19 (d, 1H), 8.56 (d, 1H), 11.18 (s, 1H), 13.77 (bs, 1H)

5-[(E)-2-(4-Chloro-2-fluoro-phenyl)-vinyl]-2-propionylamino-benzoic acid
    1H-NMR (DMSO-d6) δ 1.14 (t, 3H), 2.43 (q, 2H), 7.21 (d, 1H), 7.33 (dd, 1H), 7.39 (d, 1H), 7.48 (dd, 1H), 7.84 (t, 1H), 7.91 (dd, 1H), 8.17 (d, 1H), 8.56 (d, 1H), 11.28 (s, 1H), 13.77 (bs, 1H)

5-[(E)-2-(2-Chloro-4-trifluoromethyl-phenyl)-vinyl]-2-propionylamino-benzoic acid 5-[(E)-2-(3,4-Bis-trifluoromethyl-phenyl)-vinyl]-2-propionylamino-benzoic acid 5-[(E)-2-(3,4-Difluoro-phenyl)-vinyl]-2-propionylamino-benzoic acid 5-[(L)-2-(4-Chloro-3-fluoro-phenyl)-vinyl]-2-propionylamino-benzoic acid 5-[(E)-2-(2,4-Bis-trifluoromethyl-phenyl)-vinyl]-2-(cyclopropanecarbonyl-amino)-benzoic acid
    1H-NMR (DMSO-d6) δ 0.89 (d, 4H), 1.75 (m, 1H), 7.32 (dd, 1H), 7.58 (d, 1H), 7.90 (dd, 1H), 8.02 (s, 1H), 8.09 (d, 1H), 8.21 (d, 1H), 8.26 (d, 1H), 8.54 (d, 1H), 11.52 (s, 1H), 13.79 (bs, 1H)

2-(Cyclopropanecarbonyl-amino)-5-[(E)-2-(2-fluoro-4-trifluoromethyl-phenyl)-vinyl]-benzoic acid
    1H-NMR (DMSO-d6) δ 0.89 (d, 4H), 1.75 (m, 1H), 7.30 (dd, 1H), 7.54 (d, 1H), 7.61 (d, 1H), 7.71 (d, 1H), 7.95 (dd, 1H), 8.04 (t, 1H), 8.21 (d, 1H), 8.52 (d, 1H), 11.48 (s, 1H), 13.77 (bs, 1H)

2-(Cyclopropanecarbonyl-amino)-5-[(E)-2-(2,4-difluoro-phenyl)-vinyl]-benzoic acid
    1H-NMR (DMSO-d6) δ 0.88 (d, 4H), 1.74 (m, 1H), 7.15 (dt, 1H), 7.20 (d, 1H), 7.27-7.35 (m, 2H), 7.83-7.90 (m, 2H), 8.15 (d, 1H), 8.49 (d, 1H), 11.43 (s, 1H), 13.80 (bs, 1H)

5-[(E)-2-(4-Chloro-2-fluoro-phenyl)-vinyl]-2-(cyclopropanecarbonyl-amino)-benzoic acid
    1H-NMR (DMSO-d6) δ 0.88 (d, 4H), 1.74 (m, 1H), 7.21 (d, 1H), 7.33 (dd, 1H), 7.39 (d, 1H), 7.48 (dd, 1H), 7.85 (t, 1H), 7.90 (dd, 1H), 8.16 (d, 1H), 8.50 (d, 1H), 11.46 (s, 1H), 13.82 (bs, 1H)

5-[(E)-2-(2-Chloro-4-trifluoromethyl-phenyl)-vinyl]-2-(cyclopropanecarbonyl-amino)-benzoic acid 5-[(E)-2-(2-Chloro-4-fluoro-phenyl)-vinyl]-2-(cyclopropanecarbonyl-amino)-benzoic acid 2-(Cyclopropanecarbonyl-amino)-5-[(E)-2-(2,4-dichlorophenyl)-vinyl]-benzoic acid
    1H-NMR (DMSO-d6) δ 0.89 (d, 4H), 1.75 (m, 1H), 7.34 (d, 1H), 7.40 (d, 1H), 7.47 (dd, 1H), 7.66 (d, 1H), 7.89 (dd, 1H), 7.92 (d, 1H), 8.18 (d, 1H), 8.51 (d, 1H), 11.48 (s, 1H), 13.82 (bs, 1H)

5-[(E)-2-(3,4-Bis-trifluoromethyl-phenyl)-vinyl]-2-(cyclopropanecarbonyl-amino)-benzoic acid
2-(Cyclopropanecarbonyl-amino)-5-[(E)-2-(4-fluoro-3-trifluoromethyl-phenyl)-vinyl]-benzoic acid
5-[(E)-2-(4-Chloro-3-trifluoromethyl-phenyl)-vinyl]-2-(cyclopropanecarbonyl-amino)-benzoic acid
2-(Cyclopropanecarbonyl-amino)-5-[(E)-2-(3-fluoro-4-trifluoromethyl-phenyl)-vinyl]-benzoic acid
2-(Cyclopropanecarbonyl-amino)-5-[(E)-2-(3,4-difluoro-phenyl)-vinyl]-benzoic acid
5-[(E)-2-(4-Chloro-3-fluoro-phenyl)-vinyl]-2-(cyclopropanecarbonyl-amino)-benzoic acid
5-[(E)-2-(3-Chloro-4-trifluoromethyl-phenyl)-vinyl]-2-(cyclopropanecarbonyl-amino)-benzoic acid
5-[(E)-2-(3-Chloro-4-fluoro-phenyl)-vinyl]-2-(cyclopropanecarbonyl-amino)-benzoic acid
2-(Cyclopropanecarbonyl-amino)-5-[(E)-2-(3,4-dichloro-phenyl)-vinyl]-benzoic acid Pharmacological and Pharmacokinetic Methods
Inhibition of T-Cell Proliferation Inhibition of T cell proliferation was studied in a functional assay. A human T lymphoblast cell line (Jurkat) was cultured in the presence and absence, respectively, of DHODH inhibiting compounds. Jurkat cells were seeded in microtiterplates at a concentration of $5 \times 10^5$/mL in RPMI 1640 growth media supplemented with ultraglutamin, 10% fetal calf serum, 1 mM sodium pyruvat, 10 mM HEPES and 0.1 mg/mL gentamycin. A dilution series of ten different concentrations of inhibitor was added to the wells and the plates were kept in a cell incubator for 3 days. At the beginning of the last 4 hours period, the cultures were pulsed with 10 µl/well 0.1 Ci/mmol 3H-TdR and then harvested on filter papers and counted with a β-counter. The IC50 values for each compound were calculated from the obtained dose response curves. Adding uridine to a concentration of about 50 µM in the wells monitored the specificity for the mechanism i.e., the inhibition of cell proliferation is due to DHODH inhibition and not to a general cell toxicity of the compounds. This addition of uridine reverses the anti-proliferative effect by bypassing the DHODH enzyme using an external source of pyrimidine. Results in respect of a number of compounds of the invention are reported as Jurkat IC50 (in µM) in Table 1.

Metabolic Stability in Human Liver Microsomes

The metabolic stability of the test compounds was determined using human liver microsomes. Incubations were performed with a compound concentration of 0.5 µM and a protein concentration of 1 mg/mL in 50 mM sodium phosphate buffer at physiological pH (7.4) and temperature (37° C.). The incubation mixture was preincubated at 37° C. prior to addition of NADPH (1 mM, final concentration). At several time points during 60 minutes, aliquots were removed and added to a 96 well plate placed on dry ice and deep-frozen. Samples were analyzed with LC-MS for concentration of parent compound. From the slope of the log [parent compound] vs. incubation time regression line, the in vitro half-life (t½) was determined. The intrinsic clearance (CLint) can be calculated using a modified Michaelis-Menten relationship, i.e., CLint=ln 2/t½. The CLint can then be converted to CL by using the well-stirred model of hepatic extraction. A value of 1.24 L/h/kg of the hepatic blood flow in man can be used. Results with respect to a number of compounds of the invention are reported as t½ (in minutes) in Table 1.

WO 2005/075410 discloses anthranilic acid derivatives that are stated to inhibit DHODH. However, when tested in in vitro systems based on human cells, compounds of WO 2005/075410 were found to have very short oxidation half-life and/or low T-cell anti-proliferative effect (cf. Table 1). On the other hand, the present inventors now have found a number of ortho, para- or meta, para-disubstituted anthranilic acid derivatives having a substantially enhanced stability towards oxidation by human P450 cytochrome in combination with a high T-cell anti-proliferative effect. This finding is very surprising and could not have been foreseen by the skilled person on the basis of teachings of WO 2005/075410 which, as pointed out herein above, while teaching the importance of the substitution pattern, stresses that di-substitution should imperatively be in the ortho,meta-, ortho,meta'-, or meta, meta'-positions.

EP0497740 discloses compounds that are stated to be useful as antihyperproliferative/anti-inflammatory and anticancer agents. The compound disclosed as most preferred is 5-(2,5-dimethoxy-benzyloxy)-2-hydroxy-benzoic acid methyl ester. The present inventors found 5-(2,5-dimethoxy-benzyloxy)-2-hydroxy-benzoic acid to be inactive as DHODH inhibitor. EP0497740 also discloses the compound 2-acetylamino-5-(2,5-dimethoxy-benzyloxy)-benzoic acid methyl ester, which inhibits cell proliferation. This anti-proliferative effect, however, is unrelated to DHODH inhibition. The compound 2-acetylamino-5-(2,5-dimethoxy-benzyloxy)-benzoic acid (termed compound REF-8) has been tested and found to display only a weak inhibitory effect on T-cell proliferation, and a short half-life in human beings, cf. Table 1.

EP0815087 discloses compounds structurally related to compounds of formula (I) that are stated to be useful for the treatment of proliferative and/or inflammatory disorders and cancer, e.g., 2-acetylamino-5-[2-(2,5-dimethoxy-phenyl)-ethyl]-benzoic acid methyl ester. 2-Acetylamino-5-[2-(2,5-dimethoxy-phenyl)-ethyl]-benzoic acid (termed compound REF-9) has been tested and found to display a very weak inhibitory effect on T-cell proliferation, cf. Table 1.

The inhibition of T cell proliferation was studied in a human T lymphoblast cell line (Jurkat). The IC50 value for each compound was calculated from the dose response curve. The IC50 values of representative compounds are shown in Table 1. Adding uridine was used to monitor the specificity of the DHODH mechanism. The metabolic stability was studied in human liver microsomes. The metabolic stability expressed as t½ (minutes) is shown in Table 1. Table 1 exemplifies the invention, without limiting the scope thereof.

Pharmaceutically acceptable salts of the compounds of formula (I) can be prepared by reacting the free acid with a base in water or in an organic solvent. Lists of suitable salts found in Remington: The Science and Practice of Pharmacy. 21st Edition. Philadelphia, Pa. Lippincott Williams & Wilkins. 2005. Effective quantities of the compounds of this invention are preferably administered to a patient in need of such treatment according to usual routes of administration and formulated in usual pharmaceutical compositions comprising an effective amount of the active ingredient and a suitable pharmaceutically acceptable carrier. Such compositions may take a variety of forms, e.g., solutions, suspensions, emulsions, tablets, capsules, and powders prepared for oral administration, sterile solutions for parental administration, and suppositories for rectal administration or suitable topical formulations. Conventional procedures for the selection and preparation of suitable pharmaceutical formulations are described, for example, in Pharmaceutics, The Science of Dosage Form Design (2001) Edited by Aulton, Michael E. (ISBN: 0443055173).

A suitable daily dose for use in the treatment of a disease selected from autoimmune diseases, inflammatory diseases, organ transplant rejection and malignant neoplasia is contemplated to vary between 0.005 mg/kg to about 10 mg/kg body weight, in particular between 0.025 mg/kg to 2 mg/kg body weight, depending upon the specific condition to be treated, the age and weight of the specific patient, and the specific patient's response to the medication. The exact individual dosage, as well as the daily dosage, will be determined according to standard medical principles under the direction of a physician.

The invention claimed is:
1. A compound of formula (I)

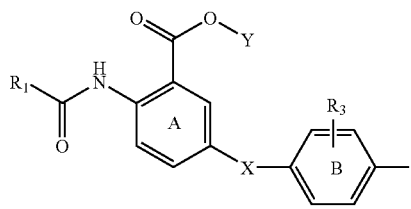

wherein
X is CH=CH, CH$_2$O wherein the oxygen is bound to ring B, or OCH$_2$ wherein the oxygen is bound to ring A;
Y is hydrogen, straight or branched C1-C6 alkyl, or a pharmaceutically acceptable inorganic cation;
R$_1$ is ethyl or cyclopropyl; and
R$_2$ and R$_3$ are the same or different and are selected from F, Cl, Br, CF$_3$ and OCF$_3$.
2. The compound according to claim 1, wherein X is CH$_2$O wherein the oxygen is bound to ring B.
3. The compound according to claim 2, wherein Y is hydrogen or a pharmaceutically acceptable inorganic cation.
4. The compound according to claim 2, wherein R$_2$ is CF$_3$ or OCF$_3$.
5. The compound according to claim 2, wherein R$_2$ is CF$_3$ or OCF$_3$ and Y is hydrogen or a pharmaceutically acceptable inorganic cation.
6. The compound according to claim 5, wherein Y is selected from the group consisting of Li$^+$, Na$^+$, K$^+$, Mg$^{2+}$, Ca$^{2+}$ and Zn$^{2+}$.
7. The compound according to claim 1, wherein R$_2$ is CF$_3$ or OCF$_3$.
8. The compound according to claim 1, wherein X is OCH$_2$ wherein the oxygen is bound to ring A.
9. The compound according to claim 1, wherein X is CH=CH.
10. The compound according to claim 1, wherein Y is a pharmaceutically acceptable inorganic cation.
11. The compound according to claim 10, wherein Y is a divalent cation.
12. The compound according to claim 11, further comprising a negative monovalent counterion.
13. The compound according to claim 12, wherein the negative monovalent counterion is a halogen ion or a bicarbonate ion.
14. The compound according to claim 10, wherein Y is selected from the group consisting of Li$^+$, Na$^+$, K$^+$, Mg$^{2+}$, Ca$^{2+}$ and Zn$^{2+}$.
15. The compound according to claim 10, wherein R$_2$ is CF$_3$ or OCF$_3$.
16. The compound according to claim 1, wherein the compound exhibits an in vitro metabolic stability towards oxidation by cytochrome P450 characterized by a half-life ($t_{1/2}$) of longer than about 70 minutes.

17. The compound according to claim 16, wherein the compound is characterized by a half-life ($t_{1/2}$) of longer than about 100 minutes.
18. The compound according to claim 17, wherein the compound is characterized by a half-life ($t_{1/2}$) of longer than about 200 minutes.
19. The compound according to claim 1, selected from the group consisting of
5-(2,4-Dichloro-benzyloxy)-2-propionylamino-benzoic acid,
5-(4-Bromo-2-trifluoromethyl-benzyloxy)-2-(cyclopropanecarbonyl-amino)-benzoic acid,
5-(4-Fluoro-2-trifluoromethyl-benzyloxy)-2-propionylamino-benzoic acid,
5-(2,4-Bis-trifluoromethyl-benzyloxy)-2-propionylamino-benzoic acid,
5-(4-Chloro-2-trifluoromethyl-benzyloxy)-2-propionylamino-benzoic acid,
5-(2-Chloro-4-fluoro-benzyloxy)-2-propionylamino-benzoic acid,
2-(Cyclopropanecarbonyl-amino)-5-(4-fluoro-2-trifluoromethyl-benzyloxy)-benzoic acid,
5-(2-Bromo-4-fluoro-benzyloxy)-2-propionylamino-benzoic acid,
5-(2-Fluoro-4-trifluoromethyl-benzyloxy)-2-propionylamino-benzoic acid,
5-(2-Bromo-4-trifluoromethyl-benzyloxy)-2-propionylamino-benzoic acid,
5-(4-Chloro-3-trifluoromethyl-benzyloxy)-2-propionylamino-benzoic acid,
5-(3,4-Dibromo-benzyloxy)-2-propionylamino-benzoic acid,
5-(4-Bromo-3-chloro-benzyloxy)-2-propionylamino-benzoic acid,
5-(4-Bromo-2-trifluoromethyl-benzyloxy)-2-propionylamino-benzoic acid,
5-(2,4-Difluoro-benzyloxy)-2-propionylamino-benzoic acid,
5-(4-Chloro-2-fluoro-benzyloxy)-2-propionylamino-benzoic acid,
5-(4-Bromo-2-fluoro-benzyloxy)-2-propionylamino-benzoic acid,
5-(2-Chloro-4-trifluoromethyl-benzyloxy)-2-propionylamino-benzoic acid,
5-(4-Bromo-2-chloro-benzyloxy)-2-propionylamino-benzoic acid,
5-(2-Bromo-4-chloro-benzyloxy)-2-propionylamino-benzoic acid,
5-(2,4-Dibromo-benzyloxy)-2-propionylamino-benzoic acid,
5-(3,4-Bis-trifluoromethyl-benzyloxy)-2-propionylamino-benzoic acid,
5-(4-Fluoro-3-trifluoromethyl-benzyloxy)-2-propionylamino-benzoic acid,
5-(4-Bromo-3-trifluoromethyl-benzyloxy)-2-propionylamino-benzoic acid,
5-(3-Fluoro-4-trifluoromethyl-benzyloxy)-2-propionylamino-benzoic acid,
5-(3,4-Difluoro-benzyloxy)-2-propionylamino-benzoic acid,
5-(4-Chloro-3-fluoro-benzyloxy)-2-propionylamino-benzoic acid,
5-(4-Bromo-3-fluoro-benzyloxy)-2-propionylamino-benzoic acid,
5-(3-Chloro-4-trifluoromethyl-benzyloxy)-2-propionylamino-benzoic acid, 5-(3-Chloro-4-fluoro-benzyloxy)-2-propionylamino-benzoic acid,
5-(3,4-Dichloro-benzyloxy)-2-propionylamino-benzoic acid,
5-(3-Bromo-4-trifluoromethyl-benzyloxy)-2-propionylamino-benzoic acid,
5-(3-Bromo-4-fluoro-benzyloxy)-2-propionylamino-benzoic acid,
5-(3-Bromo-4-chloro-benzyloxy)-2-propionylamino-benzoic acid,
5-(3-Chloro-4-trifluoromethoxy-benzyloxy)-2-propionylamino-benzoic acid,
5-(2,4-Bis-trifluoromethyl-benzyloxy)-2-(cyclopropanecarbonyl-amino)-benzoic acid,
5-(4-Chloro-2-trifluoromethyl-benzyloxy)-2-(cyclopropanecarbonyl-amino)-benzoic acid,
2-(Cyclopropanecarbonyl-amino)-5-(2-fluoro-4-trifluoromethyl-benzyloxy)-benzoic acid,
2-(Cyclopropanecarbonyl-amino)-5-(2,4-difluoro-benzyloxy)-benzoic acid,
5-(4-Chloro-2-fluoro-benzyloxy)-2-(cyclopropanecarbonyl-amino)-benzoic acid,
5-(4-Bromo-2-fluoro-benzyloxy)-2-(cyclopropanecarbonyl-amino)-benzoic acid,
5-(2-Chloro-4-trifluoromethyl-benzyloxy)-2-(cyclopropanecarbonyl-amino)-benzoic acid,
5-(2-Chloro-4-fluoro-benzyloxy)-2-(cyclopropanecarbonyl-amino)-benzoic acid,
2-(Cyclopropanecarbonyl-amino)-5-(2,4-dichloro-benzyloxy)-benzoic acid,
5-(4-Bromo-2-chloro-benzyloxy)-2-(cyclopropanecarbonyl-amino)-benzoic acid,
5-(2-Bromo-4-trifluoromethyl-benzyloxy)-2-(cyclopropanecarbonyl-amino)-benzoic acid,
5-(2-Bromo-4-fluoro-benzyloxy)-2-(cyclopropanecarbonyl-amino)-benzoic acid,
5-(2-Bromo-4-chloro-benzyloxy)-2-(cyclopropanecarbonyl-amino)-benzoic acid,
2-(Cyclopropanecarbonyl-amino)-5-(2,4-dibromo-benzyloxy)-benzoic acid,
5-(3,4-Bis-trifluoromethyl-benzyloxy)-2-(cyclopropanecarbonyl-amino)-benzoic acid,
2-(Cyclopropanecarbonyl-amino)-5-(4-fluoro-3-trifluoromethyl-benzyloxy)-benzoic acid,
5-(4-Chloro-3-trifluoromethyl-benzyloxy)-2-(cyclopropanecarbonyl-amino)-benzoic acid,
5-(4-Bromo-3-trifluoromethyl-benzyloxy)-2-(cyclopropanecarbonyl-amino)-benzoic acid,
2-(Cyclopropanecarbonyl-amino)-5-(3-fluoro-4-trifluoromethyl-benzyloxy)-benzoic acid,
2-(Cyclopropanecarbonyl-amino)-5-(3,4-difluoro-benzyloxy)-benzoic acid,
5-(4-Chloro-3-fluoro-benzyloxy)-2-(cyclopropanecarbonyl-amino)-benzoic acid,
5-(4-Bromo-3-fluoro-benzyloxy)-2-(cyclopropanecarbonyl-amino)-benzoic acid,
5-(3-Chloro-4-trifluoromethyl-benzyloxy)-2-(cyclopropanecarbonyl-amino)-benzoic acid,
5-(3-Chloro-4-fluoro-benzyloxy)-2-(cyclopropanecarbonyl-amino)-benzoic acid,
2-(Cyclopropanecarbonyl-amino)-5-(3,4-dichloro-benzyloxy)-benzoic acid,
5-(4-Bromo-3-chloro-benzyloxy)-2-(cyclopropanecarbonyl-amino)-benzoic acid,
5-(3-Bromo-4-trifluoromethyl-benzyloxy)-2-(cyclopropanecarbonyl-amino)-benzoic acid,
5-(3-Bromo-4-fluoro-benzyloxy)-2-(cyclopropanecarbonyl-amino)-benzoic acid,
5-(3-Bromo-4-chloro-benzyloxy)-2-(cyclopropanecarbonyl-amino)-benzoic acid,
2-(Cyclopropanecarbonyl-amino)-5-(3,4-dibromo-benzyloxy)-benzoic acid,
5-(2,4-Dichloro-phenoxymethyl)-2-propionylamino-benzoic acid,
5-(2-Chloro-4-fluoro-phenoxymethyl)-2-propionylamino-benzoic acid,
5-(2-Chloro-4-trifluoromethyl-phenoxymethyl)-2-propionylamino-benzoic acid,
5-(2-Chloro-4-trifluoromethoxy-phenoxymethyl)-2-propionylamino-benzoic acid,
5-(2-Bromo-4-fluoro-phenoxymethyl)-2-propionylamino-benzoic acid,
5-(2-Bromo-4-chloro-phenoxymethyl)-2-propionylamino-benzoic acid,
5-(2-Bromo-4-trifluoromethyl-phenoxymethyl)-2-propionylamino-benzoic acid,
5-(4-Bromo-2-trifluoromethyl-phenoxymethyl)-2-propionylamino-benzoic acid,
5-(2,4-Bis-trifluoromethyl-phenoxymethyl)-2-propionylamino-benzoic acid,
5-(4-Fluoro-2-trifluoromethyl-phenoxymethyl)-2-propionylamino-benzoic acid,
2-(Cyclopropanecarbonyl-amino)-5-(4-fluoro-2-trifluoromethyl-phenoxymethyl)-benzoic acid,
5-(2-Chloro-4-fluoro-phenoxymethyl)-2-(cyclopropanecarbonyl-amino)-benzoic acid,
5-(2-Chloro-4-trifluoromethyl-phenoxymethyl)-2-(cyclopropanecarbonyl-amino)-benzoic acid,
5-(2-Chloro-4-trifluoromethoxy-phenoxymethyl)-2-(cyclopropanecarbonyl-amino)-benzoic acid,
2-(Cyclopropanecarbonyl-amino)-5-(2,4-dichloro-phenoxymethyl)-benzoic acid,
5-(4-Fluoro-3-trifluoromethyl-phenoxymethyl)-2-propionylamino-benzoic acid,
5-(4-Chloro-3-trifluoromethyl-phenoxymethyl)-2-propionylamino-benzoic acid,
5-(3-Chloro-4-fluoro-phenoxymethyl)-2-propionylamino-benzoic acid,
5-(3-Bromo-4-trifluoromethoxy-phenoxymethyl)-2-propionylamino-benzoic acid,
5-(4-Bromo-3-chloro-phenoxymethyl)-2-propionylamino-benzoic acid,
5-(3-Chloro-4-trifluoromethoxy-phenoxymethyl)-2-propionylamino-benzoic acid,
5-(3-Chloro-4-fluoro-phenoxymethyl)-2-(cyclopropanecarbonyl-amino)-benzoic acid,
2-(Cyclopropanecarbonyl-amino)-5-(4-fluoro-3-trifluoromethyl-phenoxymethyl)-benzoic acid,
5-(4-Chloro-2-trifluoromethyl-phenoxymethyl)-2-propionylamino-benzoic acid,
5-(2-Fluoro-4-trifluoromethyl-phenoxymethyl)-2-propionylamino-benzoic acid,
5-(2,4-Difluoro-phenoxymethyl)-2-propionylamino-benzoic acid,
5-(4-Chloro-2-fluoro-phenoxymethyl)-2-propionylamino-benzoic acid,
5-(4-Bromo-2-fluoro-phenoxymethyl)-2-propionylamino-benzoic acid,
5-(4-Bromo-2-chloro-phenoxymethyl)-2-propionylamino-benzoic acid,
5-(2,4-Dibromo-phenoxymethyl)-2-propionylamino-benzoic acid, 5-(3,4-Bis-trifluoromethyl-phenoxymethyl)-2-propionylamino-benzoic acid,
5-(4-Bromo-3-trifluoromethyl-phenoxymethyl)-2-propionylamino-benzoic acid,
5-(3-Fluoro-4-trifluoromethyl-phenoxymethyl)-2-propionylamino-benzoic acid,
5-(3,4-Difluoro-phenoxymethyl)-2-propionylamino-benzoic acid,
5-(4-Chloro-3-fluoro-phenoxymethyl)-2-propionylamino-benzoic acid,
5-(4-Bromo-3-fluoro-phenoxymethyl)-2-propionylamino-benzoic acid,
5-(3-Chloro-4-trifluoromethyl-phenoxymethyl)-2-propionylamino-benzoic acid,
5-(3,4-Dichloro-phenoxymethyl)-2-propionylamino-benzoic acid,
5-(3-Bromo-4-trifluoromethyl-phenoxymethyl)-2-propionylamino-benzoic acid,
5-(3-Bromo-4-fluoro-phenoxymethyl)-2-propionylamino-benzoic acid,
5-(3-Bromo-4-chloro-phenoxymethyl)-2-propionylamino-benzoic acid,
5-(3,4-Dibromo-phenoxymethyl)-2-propionylamino-benzoic acid,
5-(2,4-Bis-trifluoromethyl-phenoxymethyl)-2-(cyclopropanecarbonyl-amino)-benzoic acid,
5-(4-Chloro-2-trifluoromethyl-phenoxymethyl)-2-(cyclopropanecarbonyl-amino)-benzoic acid,
5-(4-Bromo-2-trifluoromethyl-phenoxymethyl)-2-(cyclopropanecarbonyl-amino)-benzoic acid,
2-(Cyclopropanecarbonyl-amino)-5-(2-fluoro-4-trifluoromethyl-phenoxymethyl)-benzoic acid,
2-(Cyclopropanecarbonyl-amino)-5-(2,4-difluoro-phenoxymethyl)-benzoic acid,
5-(4-Chloro-2-fluoro-phenoxymethyl)-2-(cyclopropanecarbonyl-amino)-benzoic acid,
5-(4-Bromo-2-fluoro-phenoxymethyl)-2-(cyclopropanecarbonyl-amino)-benzoic acid,
5-(4-Bromo-2-chloro-phenoxymethyl)-2-(cyclopropanecarbonyl-amino)-benzoic acid,
5-(2-Bromo-4-trifluoromethyl-phenoxymethyl)-2-(cyclopropanecarbonyl-amino)-benzoic acid,
5-(2-Bromo-4-fluoro-phenoxymethyl)-2-(cyclopropanecarbonyl-amino)-benzoic acid,
5-(2-Bromo-4-chloro-phenoxymethyl)-2-(cyclopropanecarbonyl-amino)-benzoic acid,
2-(Cyclopropanecarbonyl-amino)-5-(2,4-dibromo-phenoxymethyl)-benzoic acid,
5-(2-Chloro-4-trifluoromethoxy-phenoxymethyl)-2-(cyclopropanecarbonyl-amino)-benzoic acid,
5-(3,4-Bis-trifluoromethyl-phenoxymethyl)-2-(cyclopropanecarbonyl-amino)-benzoic acid,
5-(4-Chloro-3-trifluoromethyl-phenoxymethyl)-2-(cyclopropanecarbonyl-amino)-benzoic acid,
5-(4-Bromo-3-trifluoromethyl-phenoxymethyl)-2-(cyclopropanecarbonyl-amino)-benzoic acid,
2-(Cyclopropanecarbonyl-amino)-5-(3-fluoro-4-trifluoromethyl-phenoxymethyl)-benzoic acid,
2-(Cyclopropanecarbonyl-amino)-5-(3,4-difluoro-phenoxymethyl)-benzoic acid,
5-(4-Chloro-3-fluoro-phenoxymethyl)-2-(cyclopropanecarbonyl-amino)-benzoic acid,
5-(4-Bromo-3-fluoro-phenoxymethyl)-2-(cyclopropanecarbonyl-amino)-benzoic acid,
5-(3-Chloro-4-trifluoromethyl-phenoxymethyl)-2-(cyclopropanecarbonyl-amino)-benzoic acid,
2-(Cyclopropanecarbonyl-amino)-5-(3,4-dichloro-phenoxymethyl)-benzoic acid,
5-(4-Bromo-3-chloro-phenoxymethyl)-2-(cyclopropanecarbonyl-amino)-benzoic acid,
5-(3-Bromo-4-trifluoromethyl-phenoxymethyl)-2-(cyclopropanecarbonyl-amino)-benzoic acid,
5-(3-Bromo-4-fluoro-phenoxymethyl)-2-(cyclopropanecarbonyl-amino)-benzoic acid,
5-(3-Bromo-4-chloro-phenoxymethyl)-2-(cyclopropanecarbonyl-amino)-benzoic acid,
2-(Cyclopropanecarbonyl-amino)-5-(3,4-dibromo-phenoxymethyl)-benzoic acid,
5-[(E)-2-(2,4-Dichloro-phenyl)-vinyl]-2-propionylamino-benzoic acid,
5-[(E)-2-(4-Fluoro-2-trifluoromethyl-phenyl)-vinyl]-2-propionylamino-benzoic acid,
5-[(E)-2-(2,4-Bis-trifluoromethyl-phenyl)-vinyl]-2-propionylamino-benzoic acid,
5-[(E)-2-(2-Chloro-4-fluoro-phenyl)-vinyl]-2-propionylamino-benzoic acid,
5-[(E)-2-(2,4-Difluoro-phenyl)-vinyl]-2-propionylamino-benzoic acid,
5-[(E)-2-(4-Chloro-2-trifluoromethyl-phenyl)-vinyl]-2-propionylamino-benzoic acid,
5-[(E)-2-(2-Fluoro-4-trifluoromethyl-phenyl)-vinyl]-2-propionylamino-benzoic acid,
2-(Cyclopropanecarbonyl-amino)-5-[(E)-2-(4-fluoro-2-trifluoromethyl-phenyl)-vinyl]-benzoic acid,
5-[(E)-2-(4-Chloro-2-trifluoromethyl-phenyl)-vinyl]-2-(cyclopropanecarbonyl-amino)-benzoic acid,
5-[(E)-2-(4-Chloro-3-trifluoromethyl-phenyl)-vinyl]-2-propionylamino-benzoic acid,
5-[(E)-2-(4-Fluoro-3-trifluoromethyl-phenyl)-vinyl]-2-propionylamino-benzoic acid,
5-[(E)-2-(3-Chloro-4-fluoro-phenyl)-vinyl]-2-propionylamino-benzoic acid,
5-[(E)-2-(3-Fluoro-4-trifluoromethyl-phenyl)-vinyl]-2-propionylamino-benzoic acid,
5-[(E)-2-(3-Chloro-4-trifluoromethoxy-phenyl)-vinyl]-2-propionylamino-benzoic acid,
5-[(E)-2-(3,4-Dichloro-phenyl)-vinyl]-2-propionylamino-benzoic acid,
5-[(E)-2-(4-Chloro-2-fluoro-phenyl)-vinyl]-2-propionylamino-benzoic acid,
5-[(E)-2-(2-Chloro-4-trifluoromethyl-phenyl)-vinyl]-2-propionylamino-benzoic acid,
5-[(E)-2-(3,4-Bis-trifluoromethyl-phenyl)-vinyl]-2-propionylamino-benzoic acid,
5-[(E)-2-(3,4-Difluoro-phenyl)-vinyl]-2-propionylamino-benzoic acid,
5-[(E)-2-(4-Chloro-3-fluoro-phenyl)-vinyl]-2-propionylamino-benzoic acid,
5-[(E)-2-(2,4-Bis-trifluoromethyl-phenyl)-vinyl]-2-(cyclopropanecarbonyl-amino)-benzoic acid,
2-(Cyclopropanecarbonyl-amino)-5-[(E)-2-(2-fluoro-4-trifluoromethyl-phenyl)-vinyl]-benzoic acid,
2-(Cyclopropanecarbonyl-amino)-5-[(E)-2-(2,4-difluoro-phenyl)-vinyl]-benzoic acid,
5-[(E)-2-(4-Chloro-2-fluoro-phenyl)-vinyl]-2-(cyclopropanecarbonyl-amino)-benzoic acid,
5-[(E)-2-(2-Chloro-4-trifluoromethyl-phenyl)-vinyl]-2-(cyclopropanecarbonyl-amino)-benzoic acid,
5-[(E)-2-(2-Chloro-4-fluoro-phenyl)-vinyl]-2-(cyclopropanecarbonyl-amino)-benzoic acid,
2-(Cyclopropanecarbonyl-amino)-5-[(E)-2-(2,4-dichloro-phenyl)-vinyl]-benzoic acid, 5-[(E)-2-(3,4-Bis-trifluoromethyl-phenyl)-vinyl]-2-(cyclopropanecarbonyl-amino)-benzoic acid,
2-(Cyclopropanecarbonyl-amino)-5-[(E)-2-(4-fluoro-3-trifluoromethyl-phenyl)-vinyl]-benzoic acid,
5-[(E)-2-(4-Chloro-3-trifluoromethyl-phenyl)-vinyl]-2-(cyclopropanecarbonyl-amino)-benzoic acid,
2-(Cyclopropanecarbonyl-amino)-5-[(E)-2-(3-fluoro-4-trifluoromethyl-phenyl)-vinyl]-benzoic acid,
2-(Cyclopropanecarbonyl-amino)-5-[(E)-2-(3,4-difluoro-phenyl)-vinyl]-benzoic acid,
5-[(E)-2-(4-Chloro-3-fluoro-phenyl)-vinyl]-2-(cyclopropanecarbonyl-amino)-benzoic acid,
5-[(E)-2-(3-Chloro-4-trifluoromethyl-phenyl)-vinyl]-2-(cyclopropanecarbonyl-amino)-benzoic acid,
5-[(E)-2-(3-Chloro-4-fluoro-phenyl)-vinyl]-2-(cyclopropanecarbonyl-amino)-benzoic acid,
2-(Cyclopropanecarbonyl-amino)-5-[(E)-2-(3,4-dichloro-phenyl)-vinyl]-benzoic acid,
and pharmaceutically acceptable salts thereof.

20. The compound according to claim 1, selected from the group consisting of
5-(2,4-Dichloro-benzyloxy)-2-propionylamino-benzoic acid,
5-(4-Bromo-2-trifluoromethyl-benzyloxy)-2-(cyclopropanecarbonyl-amino)-benzoic acid,
5-(4-Fluoro-2-trifluoromethyl-benzyloxy)-2-propionylamino-benzoic acid,
5-(2,4-Bis-trifluoromethyl-benzyloxy)-2-propionylamino-benzoic acid,
5-(4-Chloro-2-trifluoromethyl-benzyloxy)-2-propionylamino-benzoic acid,
5-(2-Chloro-4-fluoro-benzyloxy)-2-propionylamino-benzoic acid,
2-(Cyclopropanecarbonyl-amino)-5-(4-fluoro-2-trifluoromethyl-benzyloxy)-benzoic acid,
5-(2-Bromo-4-fluoro-benzyloxy)-2-propionylamino-benzoic acid,
5-(2-Fluoro-4-trifluoromethyl-benzyloxy)-2-propionylamino-benzoic acid,
5-(2-Bromo-4-trifluoromethyl-benzyloxy)-2-propionylamino-benzoic acid,
5-(4-Chloro-3-trifluoromethyl-benzyloxy)-2-propionylamino-benzoic acid,
5-(3,4-Dibromo-benzyloxy)-2-propionylamino-benzoic acid,
5-(4-Bromo-3-chloro-benzyloxy)-2-propionylamino-benzoic acid,
5-(4-Bromo-2-trifluoromethyl-benzyloxy)-2-propionylamino-benzoic acid,
5-(2,4-Difluoro-benzyloxy)-2-propionylamino-benzoic acid,
5-(4-Chloro-2-fluoro-benzyloxy)-2-propionylamino-benzoic acid,
5-(4-Bromo-2-fluoro-benzyloxy)-2-propionylamino-benzoic acid,
5-(4-Fluoro-3-trifluoromethyl-benzyloxy)-2-propionylamino-benzoic acid,
5-(3-Fluoro-4-trifluoromethyl-benzyloxy)-2-propionylamino-benzoic acid,
5-(3-Chloro-4-fluoro-benzyloxy)-2-propionylamino-benzoic acid,
5-(3,4-Dichloro-benzyloxy)-2-propionylamino-benzoic acid,
5-(3-Bromo-4-chloro-benzyloxy)-2-propionylamino-benzoic acid,
5-(3-Chloro-4-trifluoromethoxy-benzyloxy)-2-propionylamino-benzoic acid,
5-(2,4-Bis-trifluoromethyl-benzyloxy)-2-(cyclopropanecarbonyl-amino)-benzoic acid,
5-(4-Chloro-2-trifluoromethyl-benzyloxy)-2-(cyclopropanecarbonyl-amino)-benzoic acid,
2-(Cyclopropanecarbonyl-amino)-5-(2-fluoro-4-trifluoromethyl-benzyloxy)-benzoic acid,
2-(Cyclopropanecarbonyl-amino)-5-(2,4-difluoro-benzyloxy)-benzoic acid,
5-(4-Chloro-2-fluoro-benzyloxy)-2-(cyclopropanecarbonyl-amino)-benzoic acid,
5-(4-Bromo-2-fluoro-benzyloxy)-2-(cyclopropanecarbonyl-amino)-benzoic acid,
5-(2-Chloro-4-fluoro-benzyloxy)-2-(cyclopropanecarbonyl-amino)-benzoic acid,
2-(Cyclopropanecarbonyl-amino)-5-(2,4-dichloro-benzyloxy)-benzoic acid,
5-(2-Bromo-4-trifluoromethyl-benzyloxy)-2-(cyclopropanecarbonyl-amino)-benzoic acid,
5-(2-Bromo-4-fluoro-benzyloxy)-2-(cyclopropanecarbonyl-amino)-benzoic acid,
5-(2,4-Dichloro-phenoxymethyl)-2-propionylamino-benzoic acid,
5-(2-Chloro-4-fluoro-phenoxymethyl)-2-propionylamino-benzoic acid,
5-(2-Chloro-4-trifluoromethyl-phenoxymethyl)-2-propionylamino-benzoic acid,
5-(2-Chloro-4-trifluoromethoxy-phenoxymethyl)-2-propionylamino-benzoic acid,
5-(2-Bromo-4-fluoro-phenoxymethyl)-2-propionylamino-benzoic acid,
5-(2-Bromo-4-chloro-phenoxymethyl)-2-propionylamino-benzoic acid,
5-(2-Bromo-4-trifluoromethyl-phenoxymethyl)-2-propionylamino-benzoic acid,
5-(4-Bromo-2-trifluoromethyl-phenoxymethyl)-2-propionylamino-benzoic acid,
5-(2,4-Bis-trifluoromethyl-phenoxymethyl)-2-propionylamino-benzoic acid,
5-(4-Fluoro-2-trifluoromethyl-phenoxymethyl)-2-propionylamino-benzoic acid,
2-(Cyclopropanecarbonyl-amino)-5-(4-fluoro-2-trifluoromethyl-phenoxymethyl)-benzoic acid,
5-(2-Chloro-4-fluoro-phenoxymethyl)-2-(cyclopropanecarbonyl-amino)-benzoic acid,
5-(2-Chloro-4-trifluoromethyl-phenoxymethyl)-2-(cyclopropanecarbonyl-amino)-benzoic acid,
5-(2-Chloro-4-trifluoromethoxy-phenoxymethyl)-2-(cyclopropanecarbonyl-amino)-benzoic acid,
2-(Cyclopropanecarbonyl-amino)-5-(2,4-dichloro-phenoxymethyl)-benzoic acid,
5-(4-Fluoro-3-trifluoromethyl-phenoxymethyl)-2-propionylamino-benzoic acid,
5-(4-Chloro-3-trifluoromethyl-phenoxymethyl)-2-propionylamino-benzoic acid,
5-(3-Chloro-4-fluoro-phenoxymethyl)-2-propionylamino-benzoic acid,
5-(3-Bromo-4-trifluoromethoxy-phenoxymethyl)-2-propionylamino-benzoic acid,
5-(4-Bromo-3-chloro-phenoxymethyl)-2-propionylamino-benzoic acid,
5-(3-Chloro-4-trifluoromethoxy-phenoxymethyl)-2-propionylamino-benzoic acid,
5-(3-Chloro-4-fluoro-phenoxymethyl)-2-(cyclopropanecarbonyl-amino)-benzoic acid,
2-(Cyclopropanecarbonyl-amino)-5-(4-fluoro-3-trifluoromethyl-phenoxymethyl)-benzoic acid, 5-(2,4-Difluoro-phenoxymethyl)-2-propionylamino-benzoic acid,
5-(4-Chloro-2-fluoro-phenoxymethyl)-2-propionylamino-benzoic acid,
5-(4-Bromo-2-fluoro-phenoxymethyl)-2-propionylamino-benzoic acid,
5-(4-Bromo-2-chloro-phenoxymethyl)-2-propionylamino-benzoic acid,
5-(2,4-Dibromo-phenoxymethyl)-2-propionylamino-benzoic acid,
5-(2,4-Bis-trifluoromethyl-phenoxymethyl)-2-(cyclopropanecarbonyl-amino)-benzoic acid,
5-(4-Bromo-2-trifluoromethyl-phenoxymethyl)-2-(cyclopropanecarbonyl-amino)-benzoic acid,
2-(Cyclopropanecarbonyl-amino)-5-(2,4-difluoro-phenoxymethyl)-benzoic acid,
5-(4-Chloro-2-fluoro-phenoxymethyl)-2-(cyclopropanecarbonyl-amino)-benzoic acid,
5-(4-Bromo-2-fluoro-phenoxymethyl)-2-(cyclopropanecarbonyl-amino)-benzoic acid,
5-(4-Bromo-2-chloro-phenoxymethyl)-2-(cyclopropanecarbonyl-amino)-benzoic acid,
5-(2-Bromo-4-trifluoromethyl-phenoxymethyl)-2-(cyclopropanecarbonyl-amino)-benzoic acid,
5-(2-Bromo-4-fluoro-phenoxymethyl)-2-(cyclopropanecarbonyl-amino)-benzoic acid,
5-(2-Bromo-4-chloro-phenoxymethyl)-2-(cyclopropanecarbonyl-amino)-benzoic acid,
2-(Cyclopropanecarbonyl-amino)-5-(2,4-dibromo-phenoxymethyl)-benzoic acid,
5-[(E)-2-(2,4-Dichloro-phenyl)-vinyl]-2-propionylamino-benzoic acid,
5-[(E)-2-(4-Fluoro-2-trifluoromethyl-phenyl)-vinyl]-2-propionylamino-benzoic acid,
5-[(E)-2-(2,4-Bis-trifluoromethyl-phenyl)-vinyl]-2-propionylamino-benzoic acid,
5-[(E)-2-(2-Chloro-4-fluoro-phenyl)-vinyl]-2-propionylamino-benzoic acid,
5-[(E)-2-(2,4-Difluoro-phenyl)-vinyl]-2-propionylamino-benzoic acid,
5-[(E)-2-(4-Chloro-2-trifluoromethyl-phenyl)-vinyl]-2-propionylamino-benzoic acid,
5-[(E)-2-(2-Fluoro-4-trifluoromethyl-phenyl)-vinyl]-2-propionylamino-benzoic acid,
2-(Cyclopropanecarbonyl-amino)-5-[(E)-2-(4-fluoro-2-trifluoromethyl-phenyl)-vinyl]-benzoic acid,
5-[(E)-2-(4-Chloro-2-trifluoromethyl-phenyl)-vinyl]-2-(cyclopropanecarbonyl-amino)-benzoic acid,
5-[(E)-2-(4-Chloro-3-trifluoromethyl-phenyl)-vinyl]-2-propionylamino-benzoic acid,
5-[(E)-2-(4-Fluoro-3-trifluoromethyl-phenyl)-vinyl]-2-propionylamino-benzoic acid,
5-[(E)-2-(3-Chloro-4-fluoro-phenyl)-vinyl]-2-propionylamino-benzoic acid,
5-[(E)-2-(3-Fluoro-4-trifluoromethyl-phenyl)-vinyl]-2-propionylamino-benzoic acid,
5-[(E)-2-(3-Chloro-4-trifluoromethoxy-phenyl)-vinyl]-2-propionylamino-benzoic acid,
5-[(E)-2-(3,4-Dichloro-phenyl)-vinyl]-2-propionylamino-benzoic acid,
5-[(E)-2-(4-Chloro-2-fluoro-phenyl)-vinyl]-2-propionylamino-benzoic acid,
5-[(E)-2-(2,4-Bis-trifluoromethyl-phenyl-vinyl]-2-(cyclopropanecarbonyl-amino)-benzoic acid,
2-(Cyclopropanecarbonyl-amino)-5-[(E)-2-(2-fluoro-4-trifluoromethyl-phenyl)-vinyl]-benzoic acid,
2-(Cyclopropanecarbonyl-amino)-5-[(E)-2-(2,4-difluoro-phenyl)-vinyl]-benzoic acid,
5-[(E)-2-(4-Chloro-2-fluoro-phenyl)-vinyl]-2-(cyclopropanecarbonyl-amino)-benzoic acid,
5-[(E)-2-(2-Chloro-4-trifluoromethyl-phenyl)-vinyl]-2-(cyclopropanecarbonyl-amino)-benzoic acid,
5-[(E)-2-(2-Chloro-4-fluoro-phenyl)-vinyl]-2-(cyclopropanecarbonyl-amino)-benzoic acid,
2-(Cyclopropanecarbonyl-amino)-5-[(E)-2-(2,4-dichloro-phenyl)-vinyl]-benzoic acid, and pharmaceutically acceptable salts thereof.

21. The compound according to claim 1, selected from the group consisting of
5-(4-Bromo-2-trifluoromethyl-benzyloxy)-2-(cyclopropanecarbonyl-amino)-benzoic acid,
5-(4-Chloro-2-trifluoromethyl-benzyloxy)-2-propionylamino-benzoic acid,
5-(2-Bromo-4-trifluoromethyl-benzyloxy)-2-propionylamino-benzoic acid,
5-(2,4-Dichloro-phenoxymethyl)-2-propionylamino-benzoic acid,
5-(2-Chloro-4-fluoro-phenoxymethyl)-2-propionylamino-benzoic acid,
5-(2-Chloro-4-trifluoromethyl-phenoxymethyl)-2-propionylamino-benzoic acid,
5-(2-Chloro-4-trifluoromethoxy-phenoxymethyl)-2-propionylamino-benzoic acid,
5-(2-Bromo-4-fluoro-phenoxymethyl)-2-propionylamino-benzoic acid,
5-(2-Bromo-4-chloro-phenoxymethyl)-2-propionylamino-benzoic acid,
5-(2-Bromo-4-trifluoromethyl-phenoxymethyl)-2-propionylamino-benzoic acid,
5-(4-Bromo-2-trifluoromethyl-phenoxymethyl)-2-propionylamino-benzoic acid,
5-(2,4-Bis-trifluoromethyl-phenoxymethyl)-2-propionylamino-benzoic acid,
5-(4-Fluoro-2-trifluoromethyl-phenoxymethyl)-2-propionylamino-benzoic acid,
5-(4-Fluoro-3-trifluoromethyl-phenoxymethyl)-2-propionylamino-benzoic acid,
5-(4-Chloro-3-trifluoromethyl-phenoxymethyl)-2-propionylamino-benzoic acid,
5-(3-Chloro-4-fluoro-phenoxymethyl)-2-propionylamino-benzoic acid,
5-(3-Bromo-4-trifluoromethoxy-phenoxymethyl)-2-propionylamino-benzoic acid,
5-(4-Bromo-3-chloro-phenoxymethyl)-2-propionylamino-benzoic acid,
5-(3-Chloro-4-trifluoromethoxy-phenoxymethyl)-2-propionylamino-benzoic acid,
5-[(E)-2-(2,4-Dichloro-phenyl)-vinyl]-2-propionylamino-benzoic acid,
5-[(E)-2-(4-Fluoro-2-trifluoromethyl-phenyl)-vinyl]-2-propionylamino-benzoic acid,
5-[(E)-2-(2,4-Bis-trifluoromethyl-phenyl)-vinyl]-2-propionylamino-benzoic acid,
5-[(E)-2-(2-Chloro-4-fluoro-phenyl)-vinyl]-2-propionylamino-benzoic acid,
5-[(E)-2-(2,4-Difluoro-phenyl)-vinyl]-2-propionylamino-benzoic acid,
5-[(E)-2-(4-Chloro-2-trifluoromethyl-phenyl)-vinyl]-2-propionylamino-benzoic acid,
5-[(E)-2-(4-Chloro-3-trifluoromethyl-phenyl)-vinyl]-2-propionylamino-benzoic acid,
5-[(E)-2-(4-Fluoro-3-trifluoromethyl-phenyl)-vinyl]-2-propionylamino-benzoic acid, 5-[(E)-2-(3-Chloro-4-fluoro-phenyl)-vinyl]-2-propionylamino-benzoic acid,
5-[(E)-2-(3-Fluoro-4-trifluoromethyl-phenyl)-vinyl]-2-propionylamino-benzoic acid,
5-[(E)-2-(3-Chloro-4-trifluoromethoxy-phenyl)-vinyl]-2-propionylamino-benzoic acid,
5-[(E)-2-(3,4-Dichloro-phenyl)-vinyl]-2-propionylamino-benzoic acid, and pharmaceutically acceptable salts thereof.

22. The compound according to claim 1, selected from the group consisting of
5-(2-Chloro-4-fluoro-phenoxymethyl)-2-propionylamino-benzoic acid,
5-(2-Chloro-4-trifluoromethoxy-phenoxymethyl)-2-propionylamino-benzoic acid,
5-(2-Bromo-4-chloro-phenoxymethyl)-2-propionylamino-benzoic acid,
5-[(E)-2-(2,4-Bis-trifluoromethyl-phenyl)-vinyl]-2-propionylamino-benzoic acid,
5-[(E)-2-(2-Chloro-4-fluoro-phenyl)-vinyl]-2-propionylamino-benzoic acid,
5-[(E)-2-(2,4-Dichloro-phenyl)-vinyl]-2-propionylamino-benzoic acid,
5-[(E)-2-(4-Chloro-2-trifluoromethyl-phenyl)-vinyl]-2-(cyclopropanecarbonyl-amino)-benzoic acid, and pharmaceutically acceptable salts thereof.

23. A pharmaceutical composition comprising a compound according to claim 1 as an active ingredient and a pharmaceutically acceptable excipient.

24. The pharmaceutical composition according to claim 23, wherein X is $CH_2O$ wherein the oxygen is bound to ring B.

25. The pharmaceutical composition according to claim 24, wherein Y is hydrogen or a pharmaceutically acceptable inorganic cation.

26. The pharmaceutical composition according to claim 24, wherein $R_2$ is $CF_3$ or $OCF_3$.

27. The pharmaceutical composition according to claim 24, wherein $R_2$ is $CF_3$ or $OCF_3$ and Y is hydrogen or a pharmaceutically acceptable inorganic cation.

28. The pharmaceutical composition according to claim 27, wherein Y is selected from the group consisting of $Li^+$, $Na^+$, $K^+$, $Mg^{2+}$, $C^{2+}$ and $Zn^{2+}$.

29. The pharmaceutical composition according to claim 23, wherein $R_2$ is $CF_3$ or $OCF_3$.

30. The pharmaceutical composition according to claim 23, wherein X is $OCH_2$ wherein the oxygen is bound to ring A.

31. The pharmaceutical composition according to claim 23, wherein X is CH=CH.

32. The pharmaceutical composition according to claim 23, wherein Y is a pharmaceutically acceptable inorganic cation.

33. The pharmaceutical composition according to claim 32, wherein Y is a divalent cation.

34. The pharmaceutical composition according to claim 33, further comprising a negative monovalent counterion.

35. The pharmaceutical composition according to claim 34, wherein the negative monovalent counterion is a halogen ion or a bicarbonate ion.

36. The pharmaceutical composition according to claim 32, wherein Y is selected from the group consisting of $Li^+$, $Na^+$, $K^+$, $Mg^{2+}$, $Ca^{2+}$ and $Zn^{2+}$.

37. The pharmaceutical composition according to claim 32, wherein $R_2$ is $CF_3$ or $OCF_3$.

38. The pharmaceutical composition according to claim 23, wherein the compound exhibits an in vitro metabolic stability towards oxidation by cytochrome P450 characterized by a half-life ($t_{1/2}$) of longer than about 70 minutes.

39. The pharmaceutical composition according to claim 38, wherein the compound is characterized by a half-life ($t_{1/2}$) of longer than about 100 minutes.

40. The pharmaceutical composition according to claim 39, wherein the compound is characterized by a half-life ($t_{1/2}$) of longer than about 200 minutes.

41. The pharmaceutical composition according to claim 23, wherein the compound is selected from the group consisting of
5-(2,4-Dichloro-benzyloxy)-2-propionylamino-benzoic acid,
5-(4-Bromo-2-trifluoromethyl-benzyloxy)-2-(cyclopropanecarbonyl-amino)-benzoic acid,
5-(4-Fluoro-2-trifluoromethyl-benzyloxy)-2-propionylamino-benzoic acid,
5-(2,4-Bis-trifluoromethyl-benzyloxy)-2-propionylamino-benzoic acid,
5-(4-Chloro-2-trifluoromethyl-benzyloxy)-2-propionylamino-benzoic acid,
5-(2-Chloro-4-fluoro-benzyloxy)-2-propionylamino-benzoic acid,
2-(Cyclopropanecarbonyl-amino)-5-(4-fluoro-2-trifluoromethyl-benzyloxy)-benzoic acid,
5-(2-Bromo-4-fluoro-benzyloxy)-2-propionylamino-benzoic acid,
5-(2-Fluoro-4-trifluoromethyl-benzyloxy)-2-propionylamino-benzoic acid,
5-(2-Bromo-4-trifluoromethyl-benzyloxy)-2-propionylamino-benzoic acid,
5-(4-Chloro-3-trifluoromethyl-benzyloxy)-2-propionylamino-benzoic acid,
5-(3,4-Dibromo-benzyloxy)-2-propionylamino-benzoic acid,
5-(4-Bromo-3-chloro-benzyloxy)-2-propionylamino-benzoic acid,
5-(4-Bromo-2-trifluoromethyl-benzyloxy)-2-propionylamino-benzoic acid,
5-(2,4-Difluoro-benzyloxy)-2-propionylamino-benzoic acid,
5-(4-Chloro-2-fluoro-benzyloxy)-2-propionylamino-benzoic acid,
5-(4-Bromo-2-fluoro-benzyloxy)-2-propionylamino-benzoic acid,
5-(2-Chloro-4-trifluoromethyl-benzyloxy)-2-propionylamino-benzoic acid,
5-(4-Bromo-2-chloro-benzyloxy)-2-propionylamino-benzoic acid,
5-(2-Bromo-4-chloro-benzyloxy)-2-propionylamino-benzoic acid,
5-(2,4-Dibromo-benzyloxy)-2-propionylamino-benzoic acid,
5-(3,4-Bis-trifluoromethyl-benzyloxy)-2-propionylamino-benzoic acid,
5-(4-Fluoro-3-trifluoromethyl-benzyloxy)-2-propionylamino-benzoic acid,
5-(4-Bromo-3-trifluoromethyl-benzyloxy)-2-propionylamino-benzoic acid,
5-(3-Fluoro-4-trifluoromethyl-benzyloxy)-2-propionylamino-benzoic acid,
5-(3,4-Difluoro-benzyloxy)-2-propionylamino-benzoic acid,
5-(4-Chloro-3-fluoro-benzyloxy)-2-propionylamino-benzoic acid,
5-(4-Bromo-3-fluoro-benzyloxy)-2-propionylamino-benzoic acid, 5-(3-Chloro-4-trifluoromethyl-benzyloxy)-2-propionylamino-benzoic acid,
5-(3-Chloro-4-fluoro-benzyloxy)-2-propionylamino-benzoic acid,
5-(3,4-Dichloro-benzyloxy)-2-propionylamino-benzoic acid,
5-(3-Bromo-4-trifluoromethyl-benzyloxy)-2-propionylamino-benzoic acid,
5-(3-Bromo-4-fluoro-benzyloxy)-2-propionylamino-benzoic acid,
5-(3-Bromo-4-chloro-benzyloxy)-2-propionylamino-benzoic acid,
5-(3-Chloro-4-trifluoromethoxy-benzyloxy)-2-propionylamino-benzoic acid,
5-(2,4-Bis-trifluoromethyl-benzyloxy)-2-(cyclopropanecarbonyl-amino)-benzoic acid,
5-(4-Chloro-2-trifluoromethyl-benzyloxy)-2-(cyclopropanecarbonyl-amino)-benzoic acid,
2-(Cyclopropanecarbonyl-amino)-5-(2-fluoro-4-trifluoromethyl-benzyloxy)-benzoic acid,
2-(Cyclopropanecarbonyl-amino)-5-(2,4-difluoro-benzyloxy)-benzoic acid,
5-(4-Chloro-2-fluoro-benzyloxy)-2-(cyclopropanecarbonyl-amino)-benzoic acid,
5-(4-Bromo-2-fluoro-benzyloxy)-2-(cyclopropanecarbonyl-amino)-benzoic acid,
5-(2-Chloro-4-trifluoromethyl-benzyloxy)-2-(cyclopropanecarbonyl-amino)-benzoic acid,
5-(2-Chloro-4-fluoro-benzyloxy)-2-(cyclopropanecarbonyl-amino)-benzoic acid,
2-(Cyclopropanecarbonyl-amino)-5-(2,4-dichloro-benzyloxy)-benzoic acid,
5-(4-Bromo-2-chloro-benzyloxy)-2-(cyclopropanecarbonyl-amino)-benzoic acid,
5-(2-Bromo-4-trifluoromethyl-benzyloxy)-2-(cyclopropanecarbonyl-amino)-benzoic acid,
5-(2-Bromo-4-fluoro-benzyloxy)-2-(cyclopropanecarbonyl-amino)-benzoic acid,
5-(2-Bromo-4-chloro-benzyloxy)-2-(cyclopropanecarbonyl-amino)-benzoic acid,
2-(Cyclopropanecarbonyl-amino)-5-(2,4-dibromo-benzyloxy)-benzoic acid,
5-(3,4-Bis-trifluoromethyl-benzyloxy)-2-(cyclopropanecarbonyl-amino)-benzoic acid,
2-(Cyclopropanecarbonyl-amino)-5-(4-fluoro-3-trifluoromethyl-benzyloxy)-benzoic acid,
5-(4-Chloro-3-trifluoromethyl-benzyloxy)-2-(cyclopropanecarbonyl-amino)-benzoic acid,
5-(4-Bromo-3-trifluoromethyl-benzyloxy)-2-(cyclopropanecarbonyl-amino)-benzoic acid,
2-(Cyclopropanecarbonyl-amino)-5-(3-fluoro-4-trifluoromethyl-benzyloxy)-benzoic acid,
2-(Cyclopropanecarbonyl-amino)-5-(3,4-difluoro-benzyloxy)-benzoic acid,
5-(4-Chloro-3-fluoro-benzyloxy)-2-(cyclopropanecarbonyl-amino)-benzoic acid,
5-(4-Bromo-3-fluoro-benzyloxy)-2-(cyclopropanecarbonyl-amino)-benzoic acid,
5-(3-Chloro-4-trifluoromethyl-benzyloxy)-2-(cyclopropanecarbonyl-amino)-benzoic acid,
5-(3-Chloro-4-fluoro-benzyloxy)-2-(cyclopropanecarbonyl-amino)-benzoic acid,
2-(Cyclopropanecarbonyl-amino)-5-(3,4-dichloro-benzyloxy)-benzoic acid,
5-(4-Bromo-3-chloro-benzyloxy)-2-(cyclopropanecarbonyl-amino)-benzoic acid,
5-(3-Bromo-4-trifluoromethyl-benzyloxy)-2-(cyclopropanecarbonyl-amino)-benzoic acid,
5-(3-Bromo-4-fluoro-benzyloxy)-2-(cyclopropanecarbonyl-amino)-benzoic acid,
5-(3-Bromo-4-chloro-benzyloxy)-2-(cyclopropanecarbonyl-amino)-benzoic acid,
2-(Cyclopropanecarbonyl-amino)-5-(3,4-dibromo-benzyloxy)-benzoic acid,
5-(2,4-Dichloro-phenoxymethyl)-2-propionylamino-benzoic acid,
5-(2-Chloro-4-fluoro-phenoxymethyl)-2-propionylamino-benzoic acid,
5-(2-Chloro-4-trifluoromethyl-phenoxymethyl)-2-propionylamino-benzoic acid,
5-(2-Chloro-4-trifluoromethoxy-phenoxymethyl)-2-propionylamino-benzoic acid,
5-(2-Bromo-4-fluoro-phenoxymethyl)-2-propionylamino-benzoic acid,
5-(2-Bromo-4-chloro-phenoxymethyl)-2-propionylamino-benzoic acid,
5-(2-Bromo-4-trifluoromethyl-phenoxymethyl)-2-propionylamino-benzoic acid,
5-(4-Bromo-2-trifluoromethyl-phenoxymethyl)-2-propionylamino-benzoic acid,
5-(2,4-Bis-trifluoromethyl-phenoxymethyl)-2-propionylamino-benzoic acid,
5-(4-Fluoro-2-trifluoromethyl-phenoxymethyl)-2-propionylamino-benzoic acid,
2-(Cyclopropanecarbonyl-amino)-5-(4-fluoro-2-trifluoromethyl-phenoxymethyl)-benzoic acid,
5-(2-Chloro-4-fluoro-phenoxymethyl)-2-(cyclopropanecarbonyl-amino)-benzoic acid,
5-(2-Chloro-4-trifluoromethyl-phenoxymethyl)-2-(cyclopropanecarbonyl-amino)-benzoic acid,
5-(2-Chloro-4-trifluoromethoxy-phenoxymethyl)-2-(cyclopropanecarbonyl-amino)-benzoic acid,
2-(Cyclopropanecarbonyl-amino)-5-(2,4-dichloro-phenoxymethyl)-benzoic acid,
5-(4-Fluoro-3-trifluoromethyl-phenoxymethyl)-2-propionylamino-benzoic acid,
5-(4-Chloro-3-trifluoromethyl-phenoxymethyl)-2-propionylamino-benzoic acid,
5-(3-Chloro-4-fluoro-phenoxymethyl)-2-propionylamino-benzoic acid,
5-(3-Bromo-4-trifluoromethoxy-phenoxymethyl)-2-propionylamino-benzoic acid,
5-(4-Bromo-3-chloro-phenoxymethyl)-2-propionylamino-benzoic acid,
5-(3-Chloro-4-trifluoromethoxy-phenoxymethyl)-2-propionylamino-benzoic acid,
5-(3-Chloro-4-fluoro-phenoxymethyl)-2-(cyclopropanecarbonyl-amino)-benzoic acid,
2-(Cyclopropanecarbonyl-amino)-5-(4-fluoro-3-trifluoromethyl-phenoxymethyl)-benzoic acid,
5-(4-Chloro-2-trifluoromethyl-phenoxymethyl)-2-propionylamino-benzoic acid,
5-(2-Fluoro-4-trifluoromethyl-phenoxymethyl)-2-propionylamino-benzoic acid,
5-(2,4-Difluoro-phenoxymethyl)-2-propionylamino-benzoic acid,
5-(4-Chloro-2-fluoro-phenoxymethyl)-2-propionylamino-benzoic acid,
5-(4-Bromo-2-fluoro-phenoxymethyl)-2-propionylamino-benzoic acid,
5-(4-Bromo-2-chloro-phenoxymethyl)-2-propionylamino-benzoic acid, 5-(2,4-Dibromo-phenoxymethyl)-2-propionylamino-benzoic acid,
5-(3,4-Bis-trifluoromethyl-phenoxymethyl)-2-propionylamino-benzoic acid,
5-(4-Bromo-3-trifluoromethyl-phenoxymethyl)-2-propionylamino-benzoic acid,
5-(3-Fluoro-4-trifluoromethyl-phenoxymethyl)-2-propionylamino-benzoic acid,
5-(3,4-Difluoro-phenoxymethyl)-2-propionylamino-benzoic acid,
5-(4-Chloro-3-fluoro-phenoxymethyl)-2-propionylamino-benzoic acid,
5-(4-Bromo-3-fluoro-phenoxymethyl)-2-propionylamino-benzoic acid,
5-(3-Chloro-4-trifluoromethyl-phenoxymethyl)-2-propionylamino-benzoic acid,
5-(3,4-Dichloro-phenoxymethyl)-2-propionylamino-benzoic acid,
5-(3-Bromo-4-trifluoromethyl-phenoxymethyl)-2-propionylamino-benzoic acid,
5-(3-Bromo-4-fluoro-phenoxymethyl)-2-propionylamino-benzoic acid,
5-(3-Bromo-4-chloro-phenoxymethyl)-2-propionylamino-benzoic acid,
5-(3,4-Dibromo-phenoxymethyl)-2-propionylamino-benzoic acid,
5-(2,4-Bis-trifluoromethyl-phenoxymethyl)-2-(cyclopropanecarbonyl-amino)-benzoic acid,
5-(4-Chloro-2-trifluoromethyl-phenoxymethyl)-2-(cyclopropanecarbonyl-amino)-benzoic acid,
5-(4-Bromo-2-trifluoromethyl-phenoxymethyl)-2-(cyclopropanecarbonyl-amino)-benzoic acid,
2-(Cyclopropanecarbonyl-amino)-5-(2-fluoro-4-trifluoromethyl-phenoxymethyl)-benzoic acid,
2-(Cyclopropanecarbonyl-amino)-5-(2,4-difluoro-phenoxymethyl)-benzoic acid,
5-(4-Chloro-2-fluoro-phenoxymethyl)-2-(cyclopropanecarbonyl-amino)-benzoic acid,
5-(4-Bromo-2-fluoro-phenoxymethyl)-2-(cyclopropanecarbonyl-amino)-benzoic acid,
5-(4-Bromo-2-chloro-phenoxymethyl)-2-(cyclopropanecarbonyl-amino)-benzoic acid,
5-(2-Bromo-4-trifluoromethyl-phenoxymethyl)-2-(cyclopropanecarbonyl-amino)-benzoic acid,
5-(2-Bromo-4-fluoro-phenoxymethyl)-2-(cyclopropanecarbonyl-amino)-benzoic acid,
5-(2-Bromo-4-chloro-phenoxymethyl)-2-(cyclopropanecarbonyl-amino)-benzoic acid,
2-(Cyclopropanecarbonyl-amino)-5-(2,4-dibromo-phenoxymethyl)-benzoic acid,
5-(2-Chloro-4-trifluoromethoxy-phenoxymethyl)-2-(cyclopropanecarbonyl-amino)-benzoic acid,
5-(3,4-Bis-trifluoromethyl-phenoxymethyl)-2-(cyclopropanecarbonyl-amino)-benzoic acid,
5-(4-Chloro-3-trifluoromethyl-phenoxymethyl)-2-(cyclopropanecarbonyl-amino)-benzoic acid,
5-(4-Bromo-3-trifluoromethyl-phenoxymethyl)-2-(cyclopropanecarbonyl-amino)-benzoic acid,
2-(Cyclopropanecarbonyl-amino)-5-(3-fluoro-4-trifluoromethyl-phenoxymethyl)-benzoic acid,
2-(Cyclopropanecarbonyl-amino)-5-(3,4-difluoro-phenoxymethyl)-benzoic acid,
5-(4-Chloro-3-fluoro-phenoxymethyl)-2-(cyclopropanecarbonyl-amino)-benzoic acid,
5-(4-Bromo-3-fluoro-phenoxymethyl)-2-(cyclopropanecarbonyl-amino)-benzoic acid,
5-(3-Chloro-4-trifluoromethyl-phenoxymethyl)-2-(cyclopropanecarbonyl-amino)-benzoic acid,
2-(Cyclopropanecarbonyl-amino)-5-(3,4-dichloro-phenoxymethyl)-benzoic acid,
5-(4-Bromo-3-chloro-phenoxymethyl)-2-(cyclopropanecarbonyl-amino)-benzoic acid,
5-(3-Bromo-4-trifluoromethyl-phenoxymethyl)-2-(cyclopropanecarbonyl-amino)-benzoic acid,
5-(3-Bromo-4-fluoro-phenoxymethyl)-2-(cyclopropanecarbonyl-amino)-benzoic acid,
5-(3-Bromo-4-chloro-phenoxymethyl)-2-(cyclopropanecarbonyl-amino)-benzoic acid,
2-(Cyclopropanecarbonyl-amino)-5-(3,4-dibromo-phenoxymethyl)-benzoic acid,
5-[(E)-2-(2,4-Dichloro-phenyl)-vinyl]-2-propionylamino-benzoic acid,
5-[(E)-2-(4-Fluoro-2-trifluoromethyl-phenyl)-vinyl]-2-propionylamino-benzoic acid,
5-[(E)-2-(2,4-Bis-trifluoromethyl-phenyl)-vinyl]-2-propionylamino-benzoic acid,
5-[(E)-2-(2-Chloro-4-fluoro-phenyl)-vinyl]-2-propionylamino-benzoic acid,
5-[(E)-2-(2,4-Difluoro-phenyl)-vinyl]-2-propionylamino-benzoic acid,
5-[(E)-2-(4-Chloro-2-trifluoromethyl-phenyl)-vinyl]-2-propionylamino-benzoic acid,
5-[(E)-2-(2-Fluoro-4-trifluoromethyl-phenyl)-vinyl]-2-propionylamino-benzoic acid,
2-(Cyclopropanecarbonyl-amino)-5-[(E)-2-(4-fluoro-2-trifluoromethyl-phenyl)-vinyl]-benzoic acid,
5-[(E)-2-(4-Chloro-2-trifluoromethyl-phenyl)-vinyl]-2-(cyclopropanecarbonyl-amino)-benzoic acid,
5-[(E)-2-(4-Chloro-3-trifluoromethyl-phenyl)-vinyl]-2-propionylamino-benzoic acid,
5-[(E)-2-(4-Fluoro-3-trifluoromethyl-phenyl)-vinyl]-2-propionylamino-benzoic acid,
5-[(E)-2-(3-Chloro-4-fluoro-phenyl)-vinyl]-2-propionylamino-benzoic acid,
5-[(E)-2-(3-Fluoro-4-trifluoromethyl-phenyl)-vinyl]-2-propionylamino-benzoic acid,
5-[(E)-2-(3-Chloro-4-trifluoromethoxy-phenyl)-vinyl]-2-propionylamino-benzoic acid,
5-[(E)-2-(3,4-Dichloro-phenyl)-vinyl]-2-propionylamino-benzoic acid,
5-[(E)-2-(4-Chloro-2-fluoro-phenyl)-vinyl]-2-propionylamino-benzoic acid,
5-[(E)-2-(2-Chloro-4-trifluoromethyl-phenyl)-vinyl]-2-propionylamino-benzoic acid,
5-[(E)-2-(3,4-Bis-trifluoromethyl-phenyl)-vinyl]-2-propionylamino-benzoic acid,
5-[(E)-2-(3,4-Difluoro-phenyl)-vinyl]-2-propionylamino-benzoic acid,
5-[(E)-2-(4-Chloro-3-fluoro-phenyl)-vinyl]-2-propionylamino-benzoic acid,
5-[(E)-2-(2,4-Bis-trifluoromethyl-phenyl)-vinyl]-2-(cyclopropanecarbonyl-amino)-benzoic acid,
2-(Cyclopropanecarbonyl-amino)-5-[(E)-2-(2-fluoro-4-trifluoromethyl-phenyl)-vinyl]-benzoic acid,
2-(Cyclopropanecarbonyl-amino)-5-[(E)-2-(2,4-difluoro-phenyl)-vinyl]-benzoic acid,
5-[(E)-2-(4-Chloro-2-fluoro-phenyl)-vinyl]-2-(cyclopropanecarbonyl-amino)-benzoic acid,
5-[(E)-2-(2-Chloro-4-trifluoromethyl-phenyl)-vinyl]-2-(cyclopropanecarbonyl-amino)-benzoic acid,
5-[(E)-2-(2-Chloro-4-fluoro-phenyl)-vinyl]-2-(cyclopropanecarbonyl-amino)-benzoic acid, 2-(Cyclopropanecarbonyl-amino)-5-[(E)-2-(2,4-dichloro-phenyl)-vinyl]-benzoic acid,
5-[(E)-2-(3,4-Bis-trifluoromethyl-phenyl)-vinyl]-2-(cyclopropanecarbonyl-amino)-benzoic acid,
2-(Cyclopropanecarbonyl-amino)-5-[(E)-2-(4-fluoro-3-trifluoromethyl-phenyl)-vinyl]-benzoic acid,
5-[(E)-2-(4-Chloro-3-trifluoromethyl-phenyl)-vinyl]-2-(cyclopropanecarbonyl-amino)-benzoic acid,
2-(Cyclopropanecarbonyl-amino)-5-[(E)-2-(3-fluoro-4-trifluoromethyl-phenyl)-vinyl]-benzoic acid,
2-(Cyclopropanecarbonyl-amino)-5-[(E)-2-(3,4-difluoro-phenyl)-vinyl]-benzoic acid,
5-[(E)-2-(4-Chloro-3-fluoro-phenyl)-vinyl]-2-(cyclopropanecarbonyl-amino)-benzoic acid,
5-[(E)-2-(3-Chloro-4-trifluoromethyl-phenyl)-vinyl]-2-(cyclopropanecarbonyl-amino)-benzoic acid,
5-[(E)-2-(3-Chloro-4-fluoro-phenyl)-vinyl]-2-(cyclopropanecarbonyl-amino)-benzoic acid,
2-(Cyclopropanecarbonyl-amino)-5-[(E)-2-(3,4-dichloro-phenyl)-vinyl]-benzoic acid,
and pharmaceutically acceptable salts thereof.

42. The pharmaceutical composition according to claim 23, wherein the compound is selected from the group consisting of
5-(2,4-Dichloro-benzyloxy)-2-propionylamino-benzoic acid,
5-(4-Bromo-2-trifluoromethyl-benzyloxy)-2-(cyclopropanecarbonyl-amino)-benzoic acid,
5-(4-Fluoro-2-trifluoromethyl-benzyloxy)-2-propionylamino-benzoic acid,
5-(2,4-Bis-trifluoromethyl-benzyloxy)-2-propionylamino-benzoic acid,
5-(4-Chloro-2-trifluoromethyl-benzyloxy)-2-propionylamino-benzoic acid,
5-(2-Chloro-4-fluoro-benzyloxy)-2-propionylamino-benzoic acid,
2-(Cyclopropanecarbonyl-amino)-5-(4-fluoro-2-trifluoromethyl-benzyloxy)-benzoic acid,
5-(2-Bromo-4-fluoro-benzyloxy)-2-propionylamino-benzoic acid,
5-(2-Fluoro-4-trifluoromethyl-benzyloxy)-2-propionylamino-benzoic acid,
5-(2-Bromo-4-trifluoromethyl-benzyloxy)-2-propionylamino-benzoic acid,
5-(4-Chloro-3-trifluoromethyl-benzyloxy)-2-propionylamino-benzoic acid,
5-(3,4-Dibromo-benzyloxy)-2-propionylamino-benzoic acid,
5-(4-Bromo-3-chloro-benzyloxy)-2-propionylamino-benzoic acid,
5-(4-Bromo-2-trifluoromethyl-benzyloxy)-2-propionylamino-benzoic acid,
5-(2,4-Difluoro-benzyloxy)-2-propionylamino-benzoic acid,
5-(4-Chloro-2-fluoro-benzyloxy)-2-propionylamino-benzoic acid,
5-(4-Bromo-2-fluoro-benzyloxy)-2-propionylamino-benzoic acid,
5-(4-Fluoro-3-trifluoromethyl-benzyloxy)-2-propionylamino-benzoic acid,
5-(3-Fluoro-4-trifluoromethyl-benzyloxy)-2-propionylamino-benzoic acid,
5-(3-Chloro-4-fluoro-benzyloxy)-2-propionylamino-benzoic acid,
5-(3,4-Dichloro-benzyloxy)-2-propionylamino-benzoic acid,
5-(3-Bromo-4-chloro-benzyloxy)-2-propionylamino-benzoic acid,
5-(3-Chloro-4-trifluoromethoxy-benzyloxy)-2-propionylamino-benzoic acid,
5-(2,4-Bis-trifluoromethyl-benzyloxy)-2-(cyclopropanecarbonyl-amino)-benzoic acid,
5-(4-Chloro-2-trifluoromethyl-benzyloxy)-2-(cyclopropanecarbonyl-amino)-benzoic acid,
2-(Cyclopropanecarbonyl-amino)-5-(2-fluoro-4-trifluoromethyl-benzyloxy)-benzoic acid,
2-(Cyclopropanecarbonyl-amino)-5-(2,4-difluoro-benzyloxy)-benzoic acid,
5-(4-Chloro-2-fluoro-benzyloxy)-2-(cyclopropanecarbonyl-amino)-benzoic acid,
5-(4-Bromo-2-fluoro-benzyloxy)-2-(cyclopropanecarbonyl-amino)-benzoic acid,
5-(2-Chloro-4-fluoro-benzyloxy)-2-(cyclopropanecarbonyl-amino)-benzoic acid,
2-(Cyclopropanecarbonyl-amino)-5-(2,4-dichloro-benzyloxy)-benzoic acid,
5-(2-Bromo-4-trifluoromethyl-benzyloxy)-2-(cyclopropanecarbonyl-amino)-benzoic acid,
5-(2-Bromo-4-fluoro-benzyloxy)-2-(cyclopropanecarbonyl-amino)-benzoic acid,
5-(2,4-Dichloro-phenoxymethyl)-2-propionylamino-benzoic acid,
5-(2-Chloro-4-fluoro-phenoxymethyl)-2-propionylamino-benzoic acid,
5-(2-Chloro-4-trifluoromethyl-phenoxymethyl)-2-propionylamino-benzoic acid,
5-(2-Chloro-4-trifluoromethoxy-phenoxymethyl)-2-propionylamino-benzoic acid,
5-(2-Bromo-4-fluoro-phenoxymethyl)-2-propionylamino-benzoic acid,
5-(2-Bromo-4-chloro-phenoxymethyl)-2-propionylamino-benzoic acid,
5-(2-Bromo-4-trifluoromethyl-phenoxymethyl)-2-propionylamino-benzoic acid,
5-(4-Bromo-2-trifluoromethyl-phenoxymethyl)-2-propionylamino-benzoic acid,
5-(2,4-Bis-trifluoromethyl-phenoxymethyl)-2-propionylamino-benzoic acid,
5-(4-Fluoro-2-trifluoromethyl-phenoxymethyl)-2-propionylamino-benzoic acid,
2-(Cyclopropanecarbonyl-amino)-5-(4-fluoro-2-trifluoromethyl-phenoxymethyl)-benzoic acid,
5-(2-Chloro-4-fluoro-phenoxymethyl)-2-(cyclopropanecarbonyl-amino)-benzoic acid,
5-(2-Chloro-4-trifluoromethyl-phenoxymethyl)-2-(cyclopropanecarbonyl-amino)-benzoic acid,
5-(2-Chloro-4-trifluoromethoxy-phenoxymethyl)-2-(cyclopropanecarbonyl-amino)-benzoic acid,
2-(Cyclopropanecarbonyl-amino)-5-(2,4-dichloro-phenoxymethyl)-benzoic acid,
5-(4-Fluoro-3-trifluoromethyl-phenoxymethyl)-2-propionylamino-benzoic acid,
5-(4-Chloro-3-trifluoromethyl-phenoxymethyl)-2-propionylamino-benzoic acid,
5-(3-Chloro-4-fluoro-phenoxymethyl)-2-propionylamino-benzoic acid,
5-(3-Bromo-4-trifluoromethoxy-phenoxymethyl)-2-propionylamino-benzoic acid,
5-(4-Bromo-3-chloro-phenoxymethyl)-2-propionylamino-benzoic acid,
5-(3-Chloro-4-trifluoromethoxy-phenoxymethyl)-2-propionylamino-benzoic acid, 5-(3-Chloro-4-fluoro-phenoxymethyl)-2-(cyclopropanecarbonyl-amino)-benzoic acid,
2-(Cyclopropanecarbonyl-amino)-5-(4-fluoro-3-trifluoromethyl-phenoxymethyl)-benzoic acid,
5-(2,4-Difluoro-phenoxymethyl)-2-propionylamino-benzoic acid,
5-(4-Chloro-2-fluoro-phenoxymethyl)-2-propionylamino-benzoic acid,
5-(4-Bromo-2-fluoro-phenoxymethyl)-2-propionylamino-benzoic acid,
5-(4-Bromo-2-chloro-phenoxymethyl)-2-propionylamino-benzoic acid,
5-(2,4-Dibromo-phenoxymethyl)-2-propionylamino-benzoic acid,
5-(2,4-Bis-trifluoromethyl-phenoxymethyl)-2-(cyclopropanecarbonyl-amino)-benzoic acid,
5-(4-Bromo-2-trifluoromethyl-phenoxymethyl)-2-(cyclopropanecarbonyl-amino)-benzoic acid,
2-(Cyclopropanecarbonyl-amino)-5-(2,4-difluoro-phenoxymethyl)-benzoic acid,
5-(4-Chloro-2-fluoro-phenoxymethyl)-2-(cyclopropanecarbonyl-amino)-benzoic acid,
5-(4-Bromo-2-fluoro-phenoxymethyl)-2-(cyclopropanecarbonyl-amino)-benzoic acid,
5-(4-Bromo-2-chloro-phenoxymethyl)-2-(cyclopropanecarbonyl-amino)-benzoic acid,
5-(2-Bromo-4-trifluoromethyl-phenoxymethyl)-2-(cyclopropanecarbonyl-amino)-benzoic acid,
5-(2-Bromo-4-fluoro-phenoxymethyl)-2-(cyclopropanecarbonyl-amino)-benzoic acid,
5-(2-Bromo-4-chloro-phenoxymethyl)-2-(cyclopropanecarbonyl-amino)-benzoic acid,
2-(Cyclopropanecarbonyl-amino)-5-(2,4-dibromo-phenoxymethyl)-benzoic acid,
5-[(E)-2-(2,4-Dichloro-phenyl)-vinyl]-2-propionylamino-benzoic acid,
5-[(E)-2-(4-Fluoro-2-trifluoromethyl-phenyl)-vinyl]-2-propionylamino-benzoic acid,
5-[(E)-2-(2,4-Bis-trifluoromethyl-phenyl)-vinyl]-2-propionylamino-benzoic acid,
5-[(E)-2-(2-Chloro-4-fluoro-phenyl)-vinyl]-2-propionylamino-benzoic acid,
5-[(E)-2-(2,4-Difluoro-phenyl)-vinyl]-2-propionylamino-benzoic acid,
5-[(E)-2-(4-Chloro-2-trifluoromethyl-phenyl)-vinyl]-2-propionylamino-benzoic acid,
5-[(E)-2-(2-Fluoro-4-trifluoromethyl-phenyl)-vinyl]-2-propionylamino-benzoic acid,
2-(Cyclopropanecarbonyl-amino)-5-[(E)-2-(4-fluoro-2-trifluoromethyl-phenyl)-vinyl]-benzoic acid,
5-[(E)-2-(4-Chloro-2-trifluoromethyl-phenyl)-vinyl]-2-(cyclopropanecarbonyl-amino)-benzoic acid,
5-[(E)-2-(4-Chloro-3-trifluoromethyl-phenyl)-vinyl]-2-propionylamino-benzoic acid,
5-[(E)-2-(4-Fluoro-3-trifluoromethyl-phenyl)-vinyl]-2-propionylamino-benzoic acid,
5-[(E)-2-(3-Chloro-4-fluoro-phenyl)-vinyl]-2-propionylamino-benzoic acid,
5-[(E)-2-(3-Fluoro-4-trifluoromethyl-phenyl)-vinyl]-2-propionylamino-benzoic acid,
5-[(E)-2-(3-Chloro-4-trifluoromethoxy-phenyl)-vinyl]-2-propionylamino-benzoic acid,
5-[(E)-2-(3,4-Dichloro-phenyl)-vinyl]-2-propionylamino-benzoic acid,
5-[(E)-2-(4-Chloro-2-fluoro-phenyl)-vinyl]-2-propionylamino-benzoic acid,
5-[(E)-2-(2,4-Bis-trifluoromethyl-phenyl-vinyl]-2-(cyclopropanecarbonyl-amino)-benzoic acid,
2-(Cyclopropanecarbonyl-amino)-5-[(E)-2-(2-fluoro-4-trifluoromethyl-phenyl)-vinyl]-benzoic acid,
2-(Cyclopropanecarbonyl-amino)-5-[(E)-2-(2,4-difluoro-phenyl)-vinyl]-benzoic acid,
5-[(E)-2-(4-Chloro-2-fluoro-phenyl)-vinyl]-2-(cyclopropanecarbonyl-amino)-benzoic acid,
5-[(E)-2-(2-Chloro-4-trifluoromethyl-phenyl)-vinyl]-2-(cyclopropanecarbonyl-amino)-benzoic acid,
5-[(E)-2-(2-Chloro-4-fluoro-phenyl)-vinyl]-2-(cyclopropanecarbonyl-amino)-benzoic acid,
2-(Cyclopropanecarbonyl-amino)-5-[(E)-2-(2,4-dichloro-phenyl)-vinyl]-benzoic acid, and pharmaceutically acceptable salts thereof.

43. The pharmaceutical composition according to claim 23, wherein the compound is selected from the group consisting of
5-(4-Bromo-2-trifluoromethyl-benzyloxy)-2-(cyclopropanecarbonyl-amino)-benzoic acid,
5-(4-Chloro-2-trifluoromethyl-benzyloxy)-2-propionylamino-benzoic acid,
5-(2-Bromo-4-trifluoromethyl-benzyloxy)-2-propionylamino-benzoic acid,
5-(2,4-Dichloro-phenoxymethyl)-2-propionylamino-benzoic acid,
5-(2-Chloro-4-fluoro-phenoxymethyl)-2-propionylamino-benzoic acid,
5-(2-Chloro-4-trifluoromethyl-phenoxymethyl)-2-propionylamino-benzoic acid,
5-(2-Chloro-4-trifluoromethoxy-phenoxymethyl)-2-propionylamino-benzoic acid,
5-(2-Bromo-4-fluoro-phenoxymethyl)-2-propionylamino-benzoic acid,
5-(2-Bromo-4-chloro-phenoxymethyl)-2-propionylamino-benzoic acid,
5-(2-Bromo-4-trifluoromethyl-phenoxymethyl)-2-propionylamino-benzoic acid,
5-(4-Bromo-2-trifluoromethyl-phenoxymethyl)-2-propionylamino-benzoic acid,
5-(2,4-Bis-trifluoromethyl-phenoxymethyl)-2-propionylamino-benzoic acid,
5-(4-Fluoro-2-trifluoromethyl-phenoxymethyl)-2-propionylamino-benzoic acid,
5-(4-Fluoro-3-trifluoromethyl-phenoxymethyl)-2-propionylamino-benzoic acid,
5-(4-Chloro-3-trifluoromethyl-phenoxymethyl)-2-propionylamino-benzoic acid,
5-(3-Chloro-4-fluoro-phenoxymethyl)-2-propionylamino-benzoic acid,
5-(3-Bromo-4-trifluoromethoxy-phenoxymethyl)-2-propionylamino-benzoic acid,
5-(4-Bromo-3-chloro-phenoxymethyl)-2-propionylamino-benzoic acid,
5-(3-Chloro-4-trifluoromethoxy-phenoxymethyl)-2-propionylamino-benzoic acid,
5-[(E)-2-(2,4-Dichloro-phenyl)-vinyl]-2-propionylamino-benzoic acid,
5-[(E)-2-(4-Fluoro-2-trifluoromethyl-phenyl)-vinyl]-2-propionylamino-benzoic acid,
5-[(E)-2-(2,4-Bis-trifluoromethyl-phenyl)-vinyl]-2-propionylamino-benzoic acid,
5-[(E)-2-(2-Chloro-4-fluoro-phenyl)-vinyl]-2-propionylamino-benzoic acid,
5-[(E)-2-(2,4-Difluoro-phenyl)-vinyl]-2-propionylamino-benzoic acid, 5-[(E)-2-(4-Chloro-2-trifluoromethyl-phenyl)-vinyl]-2-propionylamino-benzoic acid,
5-[(E)-2-(4-Chloro-3-trifluoromethyl-phenyl)-vinyl]-2-propionylamino-benzoic acid,
5-[(E)-2-(4-Fluoro-3-trifluoromethyl-phenyl)-vinyl]-2-propionylamino-benzoic acid,
5-[(E)-2-(3-Chloro-4-fluoro-phenyl)-vinyl]-2-propionylamino-benzoic acid,
5-[(E)-2-(3-Fluoro-4-trifluoromethyl-phenyl)-vinyl]-2-propionylamino-benzoic acid,
5-[(E)-2-(3-Chloro-4-trifluoromethoxy-phenyl)-vinyl]-2-propionylamino-benzoic acid,
5-[(E)-2-(3,4-Dichloro-phenyl)-vinyl]-2-propionylamino-benzoic acid, and pharmaceutically acceptable salts thereof.

44. The pharmaceutical composition according to claim 23, wherein the compound is selected from the group consisting of
5-(2-Chloro-4-fluoro-phenoxymethyl)-2-propionylamino-benzoic acid,
5-(2-Chloro-4-trifluoromethoxy-phenoxymethyl)-2-propionylamino-benzoic acid,
5-(2-Bromo-4-chloro-phenoxymethyl)-2-propionylamino-benzoic acid,
5-[(E)-2-(2,4-Bis-trifluoromethyl-phenyl)-vinyl]-2-propionylamino-benzoic acid,
5-[(E)-2-(2-Chloro-4-fluoro-phenyl)-vinyl]-2-propionylamino-benzoic acid,
5-[(E)-2-(2,4-Dichloro-phenyl)-vinyl]-2-propionylamino-benzoic acid,
5-[(E)-2-(4-Chloro-2-trifluoromethyl-phenyl)-vinyl]-2-(cyclopropanecarbonyl-amino)-benzoic acid, and pharmaceutically acceptable salts thereof.

45. The pharmaceutical composition according to claim 23, wherein the active ingredient is present in an amount providing a daily dosage of from about 0.005 mg/kg to about 10 mg/kg body weight.

46. The pharmaceutical composition according to claim 45, wherein the active ingredient is present in an amount providing a daily dosage of from about 0.025 mg/kg to about 2 mg/kg body weight.

47. The pharmaceutical composition according to claim 23, having a form selected from the group consisting of a solution, suspension, emulsion, tablet, capsule, or powder for oral administration, a sterile solution for parental administration, a suppository for rectal administration, and a topical formulation.

48. A method of treating a disorder or condition responsive to inhibition of dihydroorotate dehydrogenase (DHODH) in a patient, the method comprising administering, to a patient in need thereof, a therapeutically effective amount of a compound according to claim 1.

49. The method according to claim 48, wherein X is $CH_2O$ wherein the oxygen is bound to ring B.

50. The method according to claim 49, wherein Y is hydrogen or a pharmaceutically acceptable inorganic cation.

51. The method according to claim 49, wherein $R_2$ is $CF_3$ or $OCF_3$.

52. The method according to claim 49, wherein $R_2$ is $CF_3$ or $OCF_3$ and Y is hydrogen or a pharmaceutically acceptable inorganic cation.

53. The method according to claim 52, wherein Y is selected from the group consisting of $Li^+$, $Na^+$, $K^+$, $Mg^{2+}$, $Ca^{2+}$ and $Zn^{2+}$.

54. The method according to claim 48, wherein $R_2$ is $CF_3$ or $OCF_3$.

55. The method according to claim 48, wherein X is $OCH_2$ wherein the oxygen is bound to ring A.

56. The method according to claim 48, wherein X is CH=CH.

57. The method according to claim 48, wherein Y is a pharmaceutically acceptable inorganic cation.

58. The method according to claim 57, wherein Y is a divalent cation.

59. The method according to claim 58, further comprising a negative monovalent counterion.

60. The method according to claim 59, wherein the negative monovalent counterion is a halogen ion or a bicarbonate ion.

61. The method according to claim 57, wherein Y is selected from the group consisting of $Li^+$, $Na^+$, $K^+$, $Mg^{2+}$, $Ca^{2+}$ and $Zn^{2+}$.

62. The method according to claim 57, wherein $R_2$ is $CF_3$ or $OCF_3$.

63. The method according to claim 48, wherein the compound is selected from the group consisting of
5-(2,4-Dichloro-benzyloxy)-2-propionylamino-benzoic acid,
5-(4-Bromo-2-trifluoromethyl-benzyloxy)-2-(cyclopropanecarbonyl-amino)-benzoic acid,
5-(4-Fluoro-2-trifluoromethyl-benzyloxy)-2-propionylamino-benzoic acid,
5-(2,4-Bis-trifluoromethyl-benzyloxy)-2-propionylamino-benzoic acid,
5-(4-Chloro-2-trifluoromethyl-benzyloxy)-2-propionylamino-benzoic acid,
5-(2-Chloro-4-fluoro-benzyloxy)-2-propionylamino-benzoic acid,
2-(Cyclopropanecarbonyl-amino)-5-(4-fluoro-2-trifluoromethyl-benzyloxy)-benzoic acid,
5-(2-Bromo-4-fluoro-benzyloxy)-2-propionylamino-benzoic acid,
5-(2-Fluoro-4-trifluoromethyl-benzyloxy)-2-propionylamino-benzoic acid,
5-(2-Bromo-4-trifluoromethyl-benzyloxy)-2-propionylamino-benzoic acid,
5-(4-Chloro-3-trifluoromethyl-benzyloxy)-2-propionylamino-benzoic acid,
5-(3,4-Dibromo-benzyloxy)-2-propionylamino-benzoic acid,
5-(4-Bromo-3-chloro-benzyloxy)-2-propionylamino-benzoic acid,
5-(4-Bromo-2-trifluoromethyl-benzyloxy)-2-propionylamino-benzoic acid,
5-(2,4-Difluoro-benzyloxy)-2-propionylamino-benzoic acid,
5-(4-Chloro-2-fluoro-benzyloxy)-2-propionylamino-benzoic acid,
5-(4-Bromo-2-fluoro-benzyloxy)-2-propionylamino-benzoic acid,
5-(2-Chloro-4-trifluoromethyl-benzyloxy)-2-propionylamino-benzoic acid,
5-(4-Bromo-2-chloro-benzyloxy)-2-propionylamino-benzoic acid,
5-(2-Bromo-4-chloro-benzyloxy)-2-propionylamino-benzoic acid,
5-(2,4-Dibromo-benzyloxy)-2-propionylamino-benzoic acid,
5-(3,4-Bis-trifluoromethyl-benzyloxy)-2-propionylamino-benzoic acid,
5-(4-Fluoro-3-trifluoromethyl-benzyloxy)-2-propionylamino-benzoic acid, 5-(4-Bromo-3-trifluoromethyl-benzyloxy)-2-propionylamino-benzoic acid,
5-(3-Fluoro-4-trifluoromethyl-benzyloxy)-2-propionylamino-benzoic acid,
5-(3,4-Difluoro-benzyloxy)-2-propionylamino-benzoic acid,
5-(4-Chloro-3-fluoro-benzyloxy)-2-propionylamino-benzoic acid,
5-(4-Bromo-3-fluoro-benzyloxy)-2-propionylamino-benzoic acid,
5-(3-Chloro-4-trifluoromethyl-benzyloxy)-2-propionylamino-benzoic acid,
5-(3-Chloro-4-fluoro-benzyloxy)-2-propionylamino-benzoic acid,
5-(3,4-Dichloro-benzyloxy)-2-propionylamino-benzoic acid,
5-(3-Bromo-4-trifluoromethyl-benzyloxy)-2-propionylamino-benzoic acid,
5-(3-Bromo-4-fluoro-benzyloxy)-2-propionylamino-benzoic acid,
5-(3-Bromo-4-chloro-benzyloxy)-2-propionylamino-benzoic acid,
5-(3-Chloro-4-trifluoromethoxy-benzyloxy)-2-propionylamino-benzoic acid,
5-(2,4-Bis-trifluoromethyl-benzyloxy)-2-(cyclopropanecarbonyl-amino)-benzoic acid,
5-(4-Chloro-2-trifluoromethyl-benzyloxy)-2-(cyclopropanecarbonyl-amino)-benzoic acid,
2-(Cyclopropanecarbonyl-amino)-5-(2-fluoro-4-trifluoromethyl-benzyloxy)-benzoic acid,
2-(Cyclopropanecarbonyl-amino)-5-(2,4-difluoro-benzyloxy)-benzoic acid,
5-(4-Chloro-2-fluoro-benzyloxy)-2-(cyclopropanecarbonyl-amino)-benzoic acid,
5-(4-Bromo-2-fluoro-benzyloxy)-2-(cyclopropanecarbonyl-amino)-benzoic acid,
5-(2-Chloro-4-trifluoromethyl-benzyloxy)-2-(cyclopropanecarbonyl-amino)-benzoic acid,
5-(2-Chloro-4-fluoro-benzyloxy)-2-(cyclopropanecarbonyl-amino)-benzoic acid,
2-(Cyclopropanecarbonyl-amino)-5-(2,4-dichloro-benzyloxy)-benzoic acid,
5-(4-Bromo-2-chloro-benzyloxy)-2-(cyclopropanecarbonyl-amino)-benzoic acid,
5-(2-Bromo-4-trifluoromethyl-benzyloxy)-2-(cyclopropanecarbonyl-amino)-benzoic acid,
5-(2-Bromo-4-fluoro-benzyloxy)-2-(cyclopropanecarbonyl-amino)-benzoic acid,
5-(2-Bromo-4-chloro-benzyloxy)-2-(cyclopropanecarbonyl-amino)-benzoic acid,
2-(Cyclopropanecarbonyl-amino)-5-(2,4-dibromo-benzyloxy)-benzoic acid,
5-(3,4-Bis-trifluoromethyl-benzyloxy)-2-(cyclopropanecarbonyl-amino)-benzoic acid,
2-(Cyclopropanecarbonyl-amino)-5-(4-fluoro-3-trifluoromethyl-benzyloxy)-benzoic acid,
5-(4-Chloro-3-trifluoromethyl-benzyloxy)-2-(cyclopropanecarbonyl-amino)-benzoic acid,
5-(4-Bromo-3-trifluoromethyl-benzyloxy)-2-(cyclopropanecarbonyl-amino)-benzoic acid,
2-(Cyclopropanecarbonyl-amino)-5-(3-fluoro-4-trifluoromethyl-benzyloxy)-benzoic acid,
2-(Cyclopropanecarbonyl-amino)-5-(3,4-difluoro-benzyloxy)-benzoic acid,
5-(4-Chloro-3-fluoro-benzyloxy)-2-(cyclopropanecarbonyl-amino)-benzoic acid,
5-(4-Bromo-3-fluoro-benzyloxy)-2-(cyclopropanecarbonyl-amino)-benzoic acid,
5-(3-Chloro-4-trifluoromethyl-benzyloxy)-2-(cyclopropanecarbonyl-amino)-benzoic acid,
5-(3-Chloro-4-fluoro-benzyloxy)-2-(cyclopropanecarbonyl-amino)-benzoic acid,
2-(Cyclopropanecarbonyl-amino)-5-(3,4-dichloro-benzyloxy)-benzoic acid,
5-(4-Bromo-3-chloro-benzyloxy)-2-(cyclopropanecarbonyl-amino)-benzoic acid,
5-(3-Bromo-4-trifluoromethyl-benzyloxy)-2-(cyclopropanecarbonyl-amino)-benzoic acid,
5-(3-Bromo-4-fluoro-benzyloxy)-2-(cyclopropanecarbonyl-amino)-benzoic acid,
5-(3-Bromo-4-chloro-benzyloxy)-2-(cyclopropanecarbonyl-amino)-benzoic acid,
2-(Cyclopropanecarbonyl-amino)-5-(3,4-dibromo-benzyloxy)-benzoic acid,
5-(2,4-Dichloro-phenoxymethyl)-2-propionylamino-benzoic acid,
5-(2-Chloro-4-fluoro-phenoxymethyl)-2-propionylamino-benzoic acid,
5-(2-Chloro-4-trifluoromethyl-phenoxymethyl)-2-propionylamino-benzoic acid,
5-(2-Chloro-4-trifluoromethoxy-phenoxymethyl)-2-propionylamino-benzoic acid,
5-(2-Bromo-4-fluoro-phenoxymethyl)-2-propionylamino-benzoic acid,
5-(2-Bromo-4-chloro-phenoxymethyl)-2-propionylamino-benzoic acid,
5-(2-Bromo-4-trifluoromethyl-phenoxymethyl)-2-propionylamino-benzoic acid,
5-(4-Bromo-2-trifluoromethyl-phenoxymethyl)-2-propionylamino-benzoic acid,
5-(2,4-Bis-trifluoromethyl-phenoxymethyl)-2-propionylamino-benzoic acid,
5-(4-Fluoro-2-trifluoromethyl-phenoxymethyl)-2-propionylamino-benzoic acid,
2-(Cyclopropanecarbonyl-amino)-5-(4-fluoro-2-trifluoromethyl-phenoxymethyl)-benzoic acid,
5-(2-Chloro-4-fluoro-phenoxymethyl)-2-(cyclopropanecarbonyl-amino)-benzoic acid,
5-(2-Chloro-4-trifluoromethyl-phenoxymethyl)-2-(cyclopropanecarbonyl-amino)-benzoic acid,
5-(2-Chloro-4-trifluoromethoxy-phenoxymethyl)-2-(cyclopropanecarbonyl-amino)-benzoic acid,
2-(Cyclopropanecarbonyl-amino)-5-(2,4-dichloro-phenoxymethyl)-benzoic acid,
5-(4-Fluoro-3-trifluoromethyl-phenoxymethyl)-2-propionylamino-benzoic acid,
5-(4-Chloro-3-trifluoromethyl-phenoxymethyl)-2-propionylamino-benzoic acid,
5-(3-Chloro-4-fluoro-phenoxymethyl)-2-propionylamino-benzoic acid,
5-(3-Bromo-4-trifluoromethoxy-phenoxymethyl)-2-propionylamino-benzoic acid,
5-(4-Bromo-3-chloro-phenoxymethyl)-2-propionylamino-benzoic acid,
5-(3-Chloro-4-trifluoromethoxy-phenoxymethyl)-2-propionylamino-benzoic acid,
5-(3-Chloro-4-fluoro-phenoxymethyl)-2-(cyclopropanecarbonyl-amino)-benzoic acid,
2-(Cyclopropanecarbonyl-amino)-5-(4-fluoro-3-trifluoromethyl-phenoxymethyl)-benzoic acid,
5-(4-Chloro-2-trifluoromethyl-phenoxymethyl)-2-propionylamino-benzoic acid, 5-(2-Fluoro-4-trifluoromethyl-phenoxymethyl)-2-propionylamino-benzoic acid,
5-(2,4-Difluoro-phenoxymethyl)-2-propionylamino-benzoic acid,
5-(4-Chloro-2-fluoro-phenoxymethyl)-2-propionylamino-benzoic acid,
5-(4-Bromo-2-fluoro-phenoxymethyl)-2-propionylamino-benzoic acid,
5-(4-Bromo-2-chloro-phenoxymethyl)-2-propionylamino-benzoic acid,
5-(2,4-Dibromo-phenoxymethyl)-2-propionylamino-benzoic acid,
5-(3,4-Bis-trifluoromethyl-phenoxymethyl)-2-propionylamino-benzoic acid,
5-(4-Bromo-3-trifluoromethyl-phenoxymethyl)-2-propionylamino-benzoic acid,
5-(3-Fluoro-4-trifluoromethyl-phenoxymethyl)-2-propionylamino-benzoic acid,
5-(3,4-Difluoro-phenoxymethyl)-2-propionylamino-benzoic acid,
5-(4-Chloro-3-fluoro-phenoxymethyl)-2-propionylamino-benzoic acid,
5-(4-Bromo-3-fluoro-phenoxymethyl)-2-propionylamino-benzoic acid,
5-(3-Chloro-4-trifluoromethyl-phenoxymethyl)-2-propionylamino-benzoic acid,
5-(3,4-Dichloro-phenoxymethyl)-2-propionylamino-benzoic acid,
5-(3-Bromo-4-trifluoromethyl-phenoxymethyl)-2-propionylamino-benzoic acid,
5-(3-Bromo-4-fluoro-phenoxymethyl)-2-propionylamino-benzoic acid,
5-(3-Bromo-4-chloro-phenoxymethyl)-2-propionylamino-benzoic acid,
5-(3,4-Dibromo-phenoxymethyl)-2-propionylamino-benzoic acid,
5-(2,4-Bis-trifluoromethyl-phenoxymethyl)-2-(cyclopropanecarbonyl-amino)-benzoic acid,
5-(4-Chloro-2-trifluoromethyl-phenoxymethyl)-2-(cyclopropanecarbonyl-amino)-benzoic acid,
5-(4-Bromo-2-trifluoromethyl-phenoxymethyl)-2-(cyclopropanecarbonyl-amino)-benzoic acid,
2-(Cyclopropanecarbonyl-amino)-5-(2-fluoro-4-trifluoromethyl-phenoxymethyl)-benzoic acid,
2-(Cyclopropanecarbonyl-amino)-5-(2,4-difluoro-phenoxymethyl)-benzoic acid,
5-(4-Chloro-2-fluoro-phenoxymethyl)-2-(cyclopropanecarbonyl-amino)-benzoic acid,
5-(4-Bromo-2-fluoro-phenoxymethyl)-2-(cyclopropanecarbonyl-amino)-benzoic acid,
5-(4-Bromo-2-chloro-phenoxymethyl)-2-(cyclopropanecarbonyl-amino)-benzoic acid,
5-(2-Bromo-4-trifluoromethyl-phenoxymethyl)-2-(cyclopropanecarbonyl-amino)-benzoic acid,
5-(2-Bromo-4-fluoro-phenoxymethyl)-2-(cyclopropanecarbonyl-amino)-benzoic acid,
5-(2-Bromo-4-chloro-phenoxymethyl)-2-(cyclopropanecarbonyl-amino)-benzoic acid,
2-(Cyclopropanecarbonyl-amino)-5-(2,4-dibromo-phenoxymethyl)-benzoic acid,
5-(2-Chloro-4-trifluoromethoxy-phenoxymethyl)-2-(cyclopropanecarbonyl-amino)-benzoic acid,
5-(3,4-Bis-trifluoromethyl-phenoxymethyl)-2-(cyclopropanecarbonyl-amino)-benzoic acid,
5-(4-Chloro-3-trifluoromethyl-phenoxymethyl)-2-(cyclopropanecarbonyl-amino)-benzoic acid,
5-(4-Bromo-3-trifluoromethyl-phenoxymethyl)-2-(cyclopropanecarbonyl-amino)-benzoic acid,
2-(Cyclopropanecarbonyl-amino)-5-(3-fluoro-4-trifluoromethyl-phenoxymethyl)-benzoic acid,
2-(Cyclopropanecarbonyl-amino)-5-(3,4-difluoro-phenoxymethyl)-benzoic acid,
5-(4-Chloro-3-fluoro-phenoxymethyl)-2-(cyclopropanecarbonyl-amino)-benzoic acid,
5-(4-Bromo-3-fluoro-phenoxymethyl)-2-(cyclopropanecarbonyl-amino)-benzoic acid,
5-(3-Chloro-4-trifluoromethyl-phenoxymethyl)-2-(cyclopropanecarbonyl-amino)-benzoic acid,
2-(Cyclopropanecarbonyl-amino)-5-(3,4-dichloro-phenoxymethyl)-benzoic acid,
5-(4-Bromo-3-chloro-phenoxymethyl)-2-(cyclopropanecarbonyl-amino)-benzoic acid,
5-(3-Bromo-4-trifluoromethyl-phenoxymethyl)-2-(cyclopropanecarbonyl-amino)-benzoic acid,
5-(3-Bromo-4-fluoro-phenoxymethyl)-2-(cyclopropanecarbonyl-amino)-benzoic acid,
5-(3-Bromo-4-chloro-phenoxymethyl)-2-(cyclopropanecarbonyl-amino)-benzoic acid,
2-(Cyclopropanecarbonyl-amino)-5-(3,4-dibromo-phenoxymethyl)-benzoic acid,
5-[(E)-2-(2,4-Dichloro-phenyl)-vinyl]-2-propionylamino-benzoic acid,
5-[(E)-2-(4-Fluoro-2-trifluoromethyl-phenyl)-vinyl]-2-propionylamino-benzoic acid,
5-[(E)-2-(2,4-Bis-trifluoromethyl-phenyl)-vinyl]-2-propionylamino-benzoic acid,
5-[(E)-2-(2-Chloro-4-fluoro-phenyl)-vinyl]-2-propionylamino-benzoic acid,
5-[(E)-2-(2,4-Difluoro-phenyl)-vinyl]-2-propionylamino-benzoic acid,
5-[(E)-2-(4-Chloro-2-trifluoromethyl-phenyl)-vinyl]-2-propionylamino-benzoic acid,
5-[(E)-2-(2-Fluoro-4-trifluoromethyl-phenyl)-vinyl]-2-propionylamino-benzoic acid,
2-(Cyclopropanecarbonyl-amino)-5-[(E)-2-(4-fluoro-2-trifluoromethyl-phenyl)-vinyl]-benzoic acid,
5-[(E)-2-(4-Chloro-2-trifluoromethyl-phenyl)-vinyl]-2-(cyclopropanecarbonyl-amino)-benzoic acid,
5-[(E)-2-(4-Chloro-3-trifluoromethyl-phenyl)-vinyl]-2-propionylamino-benzoic acid,
5-[(E)-2-(4-Fluoro-3-trifluoromethyl-phenyl)-vinyl]-2-propionylamino-benzoic acid,
5-[(E)-2-(3-Chloro-4-fluoro-phenyl)-vinyl]-2-propionylamino-benzoic acid,
5-[(E)-2-(3-Fluoro-4-trifluoromethyl-phenyl)-vinyl]-2-propionylamino-benzoic acid,
5-[(E)-2-(3-Chloro-4-trifluoromethoxy-phenyl)-vinyl]-2-propionylamino-benzoic acid,
5-[(E)-2-(3,4-Dichloro-phenyl)-vinyl]-2-propionylamino-benzoic acid,
5-[(E)-2-(4-Chloro-2-fluoro-phenyl)-vinyl]-2-propionylamino-benzoic acid,
5-[(E)-2-(2-Chloro-4-trifluoromethyl-phenyl)-vinyl]-2-propionylamino-benzoic acid,
5-[(E)-2-(3,4-Bis-trifluoromethyl-phenyl)-vinyl]-2-propionylamino-benzoic acid,
5-[(E)-2-(3,4-Difluoro-phenyl)-vinyl]-2-propionylamino-benzoic acid,
5-[(E)-2-(4-Chloro-3-fluoro-phenyl)-vinyl]-2-propionylamino-benzoic acid,
5-[(E)-2-(2,4-Bis-trifluoromethyl-phenyl)-vinyl]-2-(cyclopropanecarbonyl-amino)-benzoic acid, 2-(Cyclopropanecarbonyl-amino)-5-[(E)-2-(2-fluoro-4-trifluoromethyl-phenyl)-vinyl]-benzoic acid,
2-(Cyclopropanecarbonyl-amino)-5-[(E)-2-(2,4-difluoro-phenyl)-vinyl]-benzoic acid,
5-[(E)-2-(4-Chloro-2-fluoro-phenyl)-vinyl]-2-(cyclopropanecarbonyl-amino)-benzoic acid,
5-[(E)-2-(2-Chloro-4-trifluoromethyl-phenyl)-vinyl]-2-(cyclopropanecarbonyl-amino)-benzoic acid,
5-[(E)-2-(2-Chloro-4-fluoro-phenyl)-vinyl]-2-(cyclopropanecarbonyl-amino)-benzoic acid,
2-(Cyclopropanecarbonyl-amino)-5-[(E)-2-(2,4-dichloro-phenyl)-vinyl]-benzoic acid,
5-[(E)-2-(3,4-Bis-trifluoromethyl-phenyl)-vinyl]-2-(cyclopropanecarbonyl-amino)-benzoic acid,
2-(Cyclopropanecarbonyl-amino)-5-[(E)-2-(4-fluoro-3-trifluoromethyl-phenyl)-vinyl]-benzoic acid,
5-[(E)-2-(4-Chloro-3-trifluoromethyl-phenyl)-vinyl]-2-(cyclopropanecarbonyl-amino)-benzoic acid,
2-(Cyclopropanecarbonyl-amino)-5-[(E)-2-(3-fluoro-4-trifluoromethyl-phenyl)-vinyl]-benzoic acid,
2-(Cyclopropanecarbonyl-amino)-5-[(E)-2-(3,4-difluoro-phenyl)-vinyl]-benzoic acid,
5-[(E)-2-(4-Chloro-3-fluoro-phenyl)-vinyl]-2-(cyclopropanecarbonyl-amino)-benzoic acid,
5-[(E)-2-(3-Chloro-4-trifluoromethyl-phenyl)-vinyl]-2-(cyclopropanecarbonyl-amino)-benzoic acid,
5-[(E)-2-(3-Chloro-4-fluoro-phenyl)-vinyl]-2-(cyclopropanecarbonyl-amino)-benzoic acid,
2-(Cyclopropanecarbonyl-amino)-5-[(E)-2-(3,4-dichloro-phenyl)-vinyl]-benzoic acid, and pharmaceutically acceptable salts thereof.

64. The method according to claim 48, wherein the compound is selected from the group consisting of
5-(2,4-Dichloro-benzyloxy)-2-propionylamino-benzoic acid,
5-(4-Bromo-2-trifluoromethyl-benzyloxy)-2-(cyclopropanecarbonyl-amino)-benzoic acid,
5-(4-Fluoro-2-trifluoromethyl-benzyloxy)-2-propionylamino-benzoic acid,
5-(2,4-Bis-trifluoromethyl-benzyloxy)-2-propionylamino-benzoic acid,
5-(4-Chloro-2-trifluoromethyl-benzyloxy)-2-propionylamino-benzoic acid,
5-(2-Chloro-4-fluoro-benzyloxy)-2-propionylamino-benzoic acid,
2-(Cyclopropanecarbonyl-amino)-5-(4-fluoro-2-trifluoromethyl-benzyloxy)-benzoic acid,
5-(2-Bromo-4-fluoro-benzyloxy)-2-propionylamino-benzoic acid,
5-(2-Fluoro-4-trifluoromethyl-benzyloxy)-2-propionylamino-benzoic acid,
5-(2-Bromo-4-trifluoromethyl-benzyloxy)-2-propionylamino-benzoic acid,
5-(4-Chloro-3-trifluoromethyl-benzyloxy)-2-propionylamino-benzoic acid,
5-(3,4-Dibromo-benzyloxy)-2-propionylamino-benzoic acid,
5-(4-Bromo-3-chloro-benzyloxy)-2-propionylamino-benzoic acid,
5-(4-Bromo-2-trifluoromethyl-benzyloxy)-2-propionylamino-benzoic acid,
5-(2,4-Difluoro-benzyloxy)-2-propionylamino-benzoic acid,
5-(4-Chloro-fluoro-benzyloxy)-2-propionylamino-benzoic acid,
5-(4-Bromo-2-fluoro-benzyloxy)-2-propionylamino-benzoic acid,
5-(4-Fluoro-3-trifluoromethyl-benzyloxy)-2-propionylamino-benzoic acid,
5-(3-Fluoro-4-trifluoromethyl-benzyloxy)-2-propionylamino-benzoic acid,
5-(3-Chloro-4-fluoro-benzyloxy)-2-propionylamino-benzoic acid,
5-(3,4-Dichloro-benzyloxy)-2-propionylamino-benzoic acid,
5-(3-Bromo-4-chloro-benzyloxy)-2-propionylamino-benzoic acid,
5-(3-Chloro-4-trifluoromethoxy-benzyloxy)-2-propionylamino-benzoic acid,
5-(2,4-Bis-trifluoromethyl-benzyloxy)-2-(cyclopropanecarbonyl-amino)-benzoic acid,
5-(4-Chloro-2-trifluoromethyl-benzyloxy)-2-(cyclopropanecarbonyl-amino)-benzoic acid,
2-(Cyclopropanecarbonyl-amino)-5-(2-fluoro-4-trifluoromethyl-benzyloxy)-benzoic acid,
2-(Cyclopropanecarbonyl-amino)-5-(2,4-difluoro-benzyloxy)-benzoic acid,
5-(4-Chloro-2-fluoro-benzyloxy)-2-(cyclopropanecarbonyl-amino)-benzoic acid,
5-(4-Bromo-2-fluoro-benzyloxy)-2-(cyclopropanecarbonyl-amino)-benzoic acid,
5-(2-Chloro-4-fluoro-benzyloxy)-2-(cyclopropanecarbonyl-amino)-benzoic acid,
2-(Cyclopropanecarbonyl-amino)-5-(2,4-dichloro-benzyloxy)-benzoic acid,
5-(2-Bromo-4-trifluoromethyl-benzyloxy)-2-(cyclopropanecarbonyl-amino)-benzoic acid,
5-(2-Bromo-4-fluoro-benzyloxy)-2-(cyclopropanecarbonyl-amino)-benzoic acid,
5-(2,4-Dichloro-phenoxymethyl)-2-propionylamino-benzoic acid,
5-(2-Chloro-4-fluoro-phenoxymethyl)-2-propionylamino-benzoic acid,
5-(2-Chloro-4-trifluoromethyl-phenoxymethyl)-2-propionylamino-benzoic acid,
5-(2-Chloro-4-trifluoromethoxy-phenoxymethyl)-2-propionylamino-benzoic acid,
5-(2-Bromo-4-fluoro-phenoxymethyl)-2-propionylamino-benzoic acid,
5-(2-Bromo-4-chloro-phenoxymethyl)-2-propionylamino-benzoic acid,
5-(2-Bromo-4-trifluoromethyl-phenoxymethyl)-2-propionylamino-benzoic acid,
5-(4-Bromo-2-trifluoromethyl-phenoxymethyl)-2-propionylamino-benzoic acid,
5-(2,4-Bis-trifluoromethyl-phenoxymethyl)-2-propionylamino-benzoic acid,
5-(4-Fluoro-2-trifluoromethyl-phenoxymethyl)-2-propionylamino-benzoic acid,
2-(Cyclopropanecarbonyl-amino)-5-(4-fluoro-2-trifluoromethyl-phenoxymethyl)-benzoic acid,
5-(2-Chloro-4-fluoro-phenoxymethyl)-2-(cyclopropanecarbonyl-amino)-benzoic acid,
5-(2-Chloro-4-trifluoromethyl-phenoxymethyl)-2-(cyclopropanecarbonyl-amino)-benzoic acid,
5-(2-Chloro-4-trifluoromethoxy-phenoxymethyl)-2-(cyclopropanecarbonyl-amino)-benzoic acid,
2-(Cyclopropanecarbonyl-amino)-5-(2,4-dichloro-phenoxymethyl)-benzoic acid,
5-(4-Fluoro-3-trifluoromethyl-phenoxymethyl)-2-propionylamino-benzoic acid,
5-(4-Chloro-3-trifluoromethyl-phenoxymethyl)-2-propionylamino-benzoic acid, 5-(3-Chloro-4-fluoro-phenoxymethyl)-2-propionylamino-benzoic acid,
5-(3-Bromo-4-trifluoromethoxy-phenoxymethyl)-2-propionylamino-benzoic acid,
5-(4-Bromo-3-chloro-phenoxymethyl)-2-propionylamino-benzoic acid,
5-(3-Chloro-4-trifluoromethoxy-phenoxymethyl)-2-propionylamino-benzoic acid,
5-(3-Chloro-4-fluoro-phenoxymethyl)-2-(cyclopropanecarbonyl-amino)-benzoic acid,
2-(Cyclopropanecarbonyl-amino)-5-(4-fluoro-3-trifluoromethyl-phenoxymethyl)-benzoic acid,
5-(2,4-Difluoro-phenoxymethyl)-2-propionylamino-benzoic acid,
5-(4-Chloro-2-fluoro-phenoxymethyl)-2-propionylamino-benzoic acid,
5-(4-Bromo-2-fluoro-phenoxymethyl)-2-propionylamino-benzoic acid,
5-(4-Bromo-2-chloro-phenoxymethyl)-2-propionylamino-benzoic acid,
5-(2,4-Dibromo-phenoxymethyl)-2-propionylamino-benzoic acid,
5-(2,4-Bis-trifluoromethyl-phenoxymethyl)-2-(cyclopropanecarbonyl-amino)-benzoic acid,
5-(4-Bromo-2-trifluoromethyl-phenoxymethyl)-2-(cyclopropanecarbonyl-amino)-benzoic acid,
2-(Cyclopropanecarbonyl-amino)-5-(2,4-difluoro-phenoxymethyl)-benzoic acid,
5-(4-Chloro-2-fluoro-phenoxymethyl)-2-(cyclopropanecarbonyl-amino)-benzoic acid,
5-(4-Bromo-2-fluoro-phenoxymethyl)-2-(cyclopropanecarbonyl-amino)-benzoic acid,
5-(4-Bromo-2-chloro-phenoxymethyl)-2-(cyclopropanecarbonyl-amino)-benzoic acid,
5-(2-Bromo-4-trifluoromethyl-phenoxymethyl)-2-(cyclopropanecarbonyl-amino)-benzoic acid,
5-(2-Bromo-4-fluoro-phenoxymethyl)-2-(cyclopropanecarbonyl-amino)-benzoic acid,
5-(2-Bromo-4-chloro-phenoxymethyl)-2-(cyclopropanecarbonyl-amino)-benzoic acid,
2-(Cyclopropanecarbonyl-amino)-5-(2,4-dibromo-phenoxymethyl)-benzoic acid,
5-[(E)-2-(2,4-Dichloro-phenyl)-vinyl]-2-propionylamino-benzoic acid,
5-[(E)-2-(4-Fluoro-2-trifluoromethyl-phenyl)-vinyl]-2-propionylamino-benzoic acid,
5-[(E)-2-(2,4-Bis-trifluoromethyl-phenyl)-vinyl]-2-propionylamino-benzoic acid,
5-[(E)-2-(2-Chloro-4-fluoro-phenyl)-vinyl]-2-propionylamino-benzoic acid,
5-[(E)-2-(2,4-Difluoro-phenyl)-vinyl]-2-propionylamino-benzoic acid,
5-[(E)-2-(4-Chloro-2-trifluoromethyl-phenyl)-vinyl]-2-propionylamino-benzoic acid,
5-[(E)-2-(2-Fluoro-4-trifluoromethyl-phenyl)-vinyl]-2-propionylamino-benzoic acid,
2-(Cyclopropanecarbonyl-amino)-5-[(E)-2-(4-fluoro-2-trifluoromethyl-phenyl)-vinyl]-benzoic acid,
5-[(E)-2-(4-Chloro-2-trifluoromethyl-phenyl)-vinyl]-2-(cyclopropanecarbonyl-amino)-benzoic acid,
5-[(E)-2-(4-Chloro-3-trifluoromethyl-phenyl)-vinyl]-2-propionylamino-benzoic acid,
5-[(E)-2-(4-Fluoro-3-trifluoromethyl-phenyl)-vinyl]-2-propionylamino-benzoic acid,
5-[(E)-2-(3-Chloro-4-fluoro-phenyl)-vinyl]-2-propionylamino-benzoic acid,
5-[(E)-2-(3-Fluoro-4-trifluoromethyl-phenyl)-vinyl]-2-propionylamino-benzoic acid,
5-[(E)-2-(3-Chloro-4-trifluoromethoxy-phenyl)-vinyl]-2-propionylamino-benzoic acid,
5-[(E)-2-(3,4-Dichloro-phenyl)-vinyl]-2-propionylamino-benzoic acid,
5-[(E)-2-(4-Chloro-2-fluoro-phenyl)-vinyl]-2-propionylamino-benzoic acid,
5-[(E)-2-(2,4-Bis-trifluoromethyl-phenyl-vinyl]-2-(cyclopropanecarbonyl-amino)-benzoic acid,
2-(Cyclopropanecarbonyl-amino)-5-[(E)-2-(2-fluoro-4-trifluoromethyl-phenyl)-vinyl]-benzoic acid,
2-(Cyclopropanecarbonyl-amino)-5-[(E)-2-(2,4-difluoro-phenyl)-vinyl]-benzoic acid,
5-[(E)-2-(4-Chloro-2-fluoro-phenyl)-vinyl]-2-(cyclopropanecarbonyl-amino)-benzoic acid,
5-[(E)-2-(2-Chloro-4-trifluoromethyl-phenyl)-vinyl]-2-(cyclopropanecarbonyl-amino)-benzoic acid,
5-[(E)-2-(2-Chloro-4-fluoro-phenyl)-vinyl]-2-(cyclopropanecarbonyl-amino)-benzoic acid,
2-(Cyclopropanecarbonyl-amino)-5-[(E)-2-(2,4-dichloro-phenyl)-vinyl]-benzoic acid, and pharmaceutically acceptable salts thereof.

65. The method according to claim 48, wherein the compound is selected from the group consisting of
5-(4-Bromo-2-trifluoromethyl-benzyloxy)-2-(cyclopropanecarbonyl-amino)-benzoic acid,
5-(4-Chloro-2-trifluoromethyl-benzyloxy)-2-propionylamino-benzoic acid,
5-(2-Bromo-4-trifluoromethyl-benzyloxy)-2-propionylamino-benzoic acid,
5-(2,4-Dichloro-phenoxymethyl)-2-propionylamino-benzoic acid,
5-(2-Chloro-4-fluoro-phenoxymethyl)-2-propionylamino-benzoic acid,
5-(2-Chloro-4-trifluoromethyl-phenoxymethyl)-2-propionylamino-benzoic acid,
5-(2-Chloro-4-trifluoromethoxy-phenoxymethyl)-2-propionylamino-benzoic acid,
5-(2-Bromo-4-fluoro-phenoxymethyl)-2-propionylamino-benzoic acid,
5-(2-Bromo-4-chloro-phenoxymethyl)-2-propionylamino-benzoic acid,
5-(2-Bromo-4-trifluoromethyl-phenoxymethyl)-2-propionylamino-benzoic acid,
5-(4-Bromo-2-trifluoromethyl-phenoxymethyl)-2-propionylamino-benzoic acid,
5-(2,4-Bis-trifluoromethyl-phenoxymethyl)-2-propionylamino-benzoic acid,
5-(4-Fluoro-2-trifluoromethyl-phenoxymethyl)-2-propionylamino-benzoic acid,
5-(4-Fluoro-3-trifluoromethyl-phenoxymethyl)-2-propionylamino-benzoic acid,
5-(4-Chloro-3-trifluoromethyl-phenoxymethyl)-2-propionylamino-benzoic acid,
5-(3-Chloro-4-fluoro-phenoxymethyl)-2-propionylamino-benzoic acid,
5-(3-Bromo-4-trifluoromethoxy-phenoxymethyl)-2-propionylamino-benzoic acid,
5-(4-Bromo-3-chloro-phenoxymethyl)-2-propionylamino-benzoic acid,
5-(3-Chloro-4-trifluoromethoxy-phenoxymethyl)-2-propionylamino-benzoic acid,
5-[(E)-2-(2,4-Dichloro-phenyl)-vinyl]-2-propionylamino-benzoic acid, 5-[(E)-2-(4-Fluoro-2-trifluoromethyl-phenyl)-vinyl]-2-propionylamino-benzoic acid, 5-[(E)-2-(2,4-Bis-trifluoromethyl-phenyl)-vinyl]-2-propionylamino-benzoic acid, 5-[(E)-2-(2-Chloro-4-fluoro-phenyl)-vinyl]-2-propionylamino-benzoic acid, 5-[(E)-2-(2,4-Difluoro-phenyl)-vinyl]-2-propionylamino-benzoic acid, 5-[(E)-2-(4-Chloro-2-trifluoromethyl-phenyl)-vinyl]-2-propionylamino-benzoic acid, 5-[(E)-2-(4-Chloro-3-trifluoromethyl-phenyl)-vinyl]-2-propionylamino-benzoic acid, 5-[(E)-2-(4-Fluoro-3-trifluoromethyl-phenyl)-vinyl]-2-propionylamino-benzoic acid, 5-[(E)-2-(3-Chloro-4-fluoro-phenyl)-vinyl]-2-propionylamino-benzoic acid, 5-[(E)-2-(3-Fluoro-4-trifluoromethyl-phenyl)-vinyl]-2-propionylamino-benzoic acid, 5-[(E)-2-(3-Chloro-4-trifluoromethoxy-phenyl)-vinyl]-2-propionylamino-benzoic acid, 5-[(E)-2-(3,4-Dichloro-phenyl)-vinyl]-2-propionylamino-benzoic acid, and pharmaceutically acceptable salts thereof.

66. The method according to claim 48, wherein the compound is selected from the group consisting of 5-(2-Chloro-4-fluoro-phenoxymethyl)-2-propionylamino-benzoic acid, 5-(2-Chloro-4-trifluoromethoxy-phenoxymethyl)-2-propionylamino-benzoic acid, 5-(2-Bromo-4-chloro-phenoxymethyl)-2-propionylamino-benzoic acid, 5-[(E)-2-(2,4-Bis-trifluoromethyl-phenyl)-vinyl]-2-propionylamino-benzoic acid, 5-[(E)-2-(2-Chloro-4-fluoro-phenyl)-vinyl]-2-propionylamino-benzoic acid, 5-[(E)-2-(2,4-Dichloro-phenyl)-vinyl]-2-propionylamino-benzoic acid, 5-[(E)-2-(4-Chloro-2-trifluoromethyl-phenyl)-vinyl]-2-(cyclopropanecarbonyl-amino)-benzoic acid, and pharmaceutically acceptable salts thereof.

67. The method according to claim 48, wherein the disorder or condition is selected from the group consisting of autoimmune diseases, inflammatory diseases, organ transplant rejection, and malignant neoplasia.

68. The method according to claim 48, wherein the disorder or condition is selected from the group consisting of acute and chronic inflammation, rheumatoid arthritis, multiple sclerosis, type-1 diabetes, inflammatory bowel disease, and psoriasis.

69. The method according to claim 48, wherein the compound exhibits an in vitro metabolic stability towards oxidation by cytochrome P450 characterized by a half-life ($t_{1/2}$) of longer than about 70 minutes.

70. The method according to claim 69, wherein the compound is characterized by a half-life ($t_{1/2}$) of longer than about 100 minutes.

71. The method according to claim 70, wherein the compound is characterized by a half-life ($t_{1/2}$) of longer than about 200 minutes.

72. A method of preparing a compound according to claim 1, wherein X in formula (I) is $OCH_2$, by

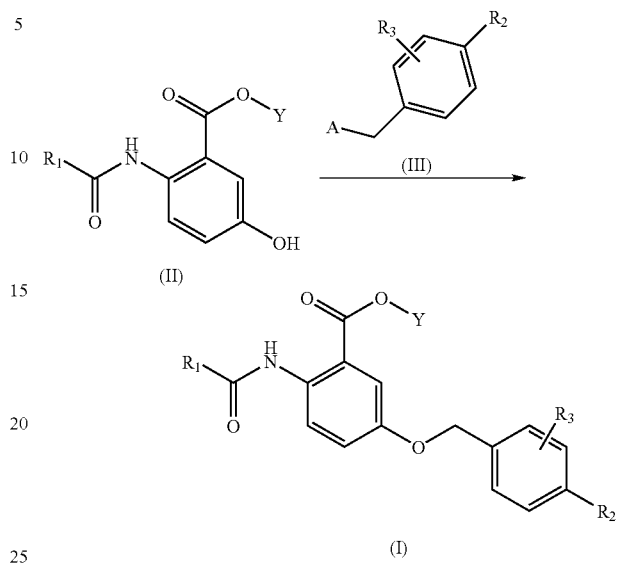

reacting a compound of formula (II) with a benzylic compound of formula (III), wherein A is a leaving group; or wherein X in formula (I) is $CH_2O$, by

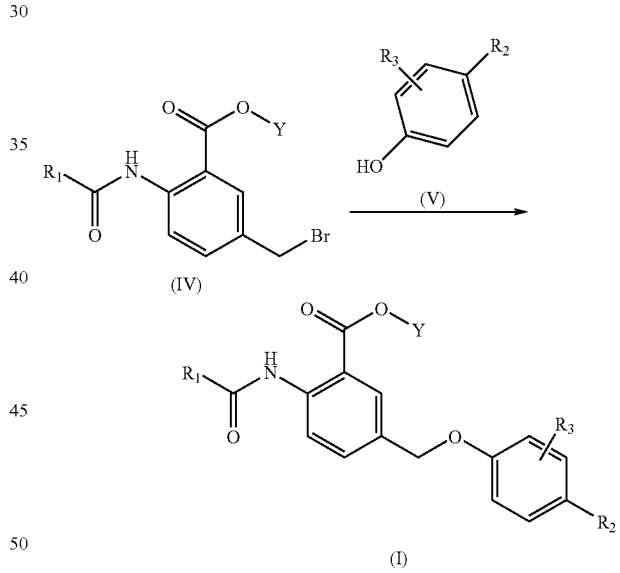

reacting a compound of formula (IV) with a phenol compound of formula (V); or wherein X in formula (I) is $CH=CH$, by

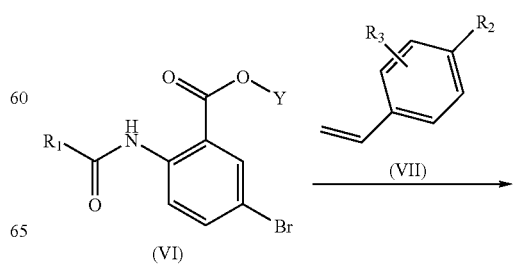

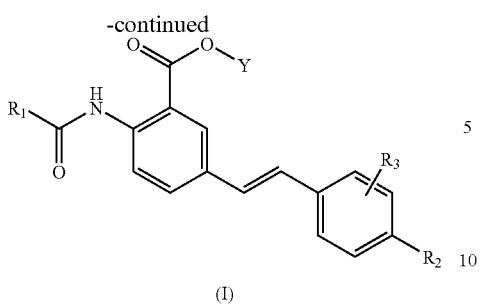

(I)

reacting a compound of formula (VI) with a styrene compound of formula (VII).

73. The method according to claim 72, wherein Y in formulae (II), (IV) and (VI) is a C1-C6 alkyl group, the method optionally comprising hydrolyzing the ester moiety C(O)OY to a carboxylic acid moiety and optionally reacting the carboxylic acid moiety with a suitable base so as to transform the carboxylic acid moiety into a carboxylic acid salt of a pharmaceutically acceptable cation.

74. The method according to claim 72, wherein said reacting steps occur in a polar aprotic solvent in the presence of an alkali metal carbonate.

75. The method according to claim 72, wherein the reaction of the compound of formula (VI) with the styrene compound of formula (VII) occurs in the presence of a palladium catalyst.

76. The method according to claim 72, wherein the compound of formula (IV) is made by

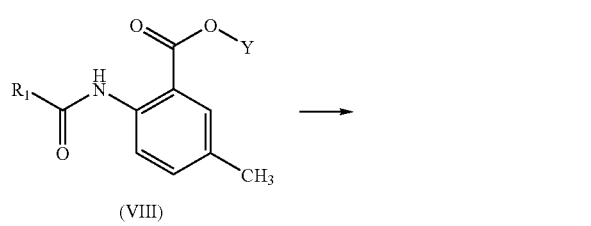

reacting a compound of formula (VIII) with 1,3-dibromo-5,5-dimethyl hydantoin.

77. The method according to claim 76, wherein the compound of formula (VIII) is made by

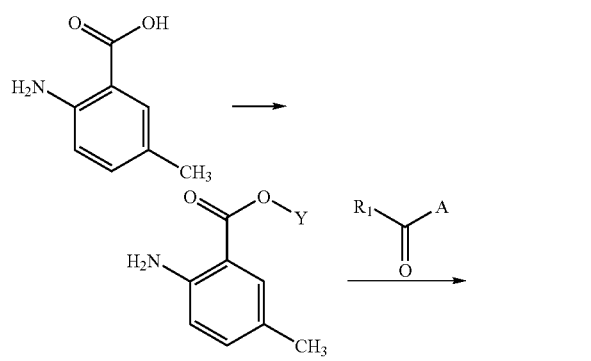

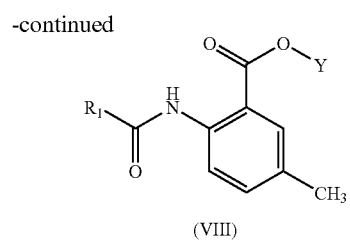

(VIII)

reacting a 5-substituted anthranilic acid with an anhydrous alcohol to provide an anthranilic ester, followed by treatment of the anthranilic ester with an acylating reagent to form the compound of formula (VIII).

78. The method according to claim 72, wherein the compound of formula (II) or formula (VI), generically represented as formula IX, is made by

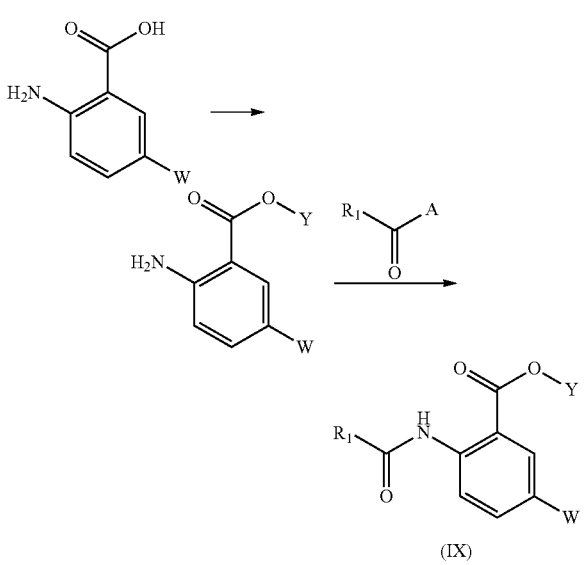

(IX)

reacting a 5-substituted anthranilic acid with an anhydrous alcohol to provide an anthranilic ester, followed by treatment of the anthranilic ester with an acylating reagent to form the compound of formula (IX), wherein W is OH or Br.

79. The method according to claim 72, wherein A is selected from the group consisting of bromide, chloride, mesyloxy, and tosyloxy.

80. The method according to claim 72, wherein the compound of formula (V) is made by

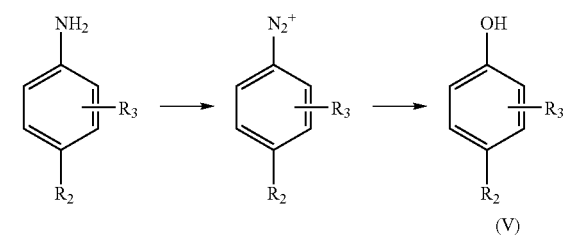

(V)

diazotation of an aniline reagent followed by boiling in sulfuric acid.

* * * * *

UNITED STATES PATENT AND TRADEMARK OFFICE
CERTIFICATE OF CORRECTION

PATENT NO.         : 8,263,658 B2                                                              Page 1 of 1
APPLICATION NO.    : 12/535358
DATED              : September 11, 2012
INVENTOR(S)        : Andersson et al.

It is certified that error appears in the above-identified patent and that said Letters Patent is hereby corrected as shown below:

On the title page, item 30, under the Foreign Application Priority Data section, please amend the priority application as follows:

Feb. 6, 2007 (SE) .......................0700281-9

In the Claims

In Column 35, beginning with line 42 and ending with line 44, please amend Claim 28 as follows:

28. The pharmaceutical composition according to claim 27, wherein Y is selected from the Group consisting of $Li^+$, $Na^+$, $K^+$, $Mg^{2+}$, [[$C^{2+}$]] $\underline{Ca^{2+}}$ and $Zn^{2+}$.

Signed and Sealed this
Twenty-fourth Day of December, 2013

Margaret A. Focarino
*Commissioner for Patents of the United States Patent and Trademark Office*